(12) United States Patent
Weinstein

(10) Patent No.: US 12,741,156 B1
(45) Date of Patent: Sep. 22, 2026

(54) RED LIGHT THERAPY DEVICES

(71) Applicant: Lee Weinstein, Milton, MA (US)

(72) Inventor: Lee Weinstein, Milton, MA (US)

(*) Notice: Subject to any disclaimer, the term of this patent is extended or adjusted under 35 U.S.C. 154(b) by 816 days.

(21) Appl. No.: 17/903,418

(22) Filed: Sep. 6, 2022

Related U.S. Application Data

(60) Provisional application No. 63/335,162, filed on Apr. 26, 2022, provisional application No. 63/245,907, filed on Sep. 19, 2021.

(51) Int. Cl.
*A61N 5/06* (2006.01)

(52) U.S. Cl.
CPC ........ *A61N 5/06* (2013.01); *A61N 2005/0644* (2013.01); *A61N 2005/0645* (2013.01); *A61N 2005/0652* (2013.01); *A61N 2005/0659* (2013.01); *A61N 2005/0663* (2013.01)

(58) Field of Classification Search
CPC ...... A61B 18/20–18/28; A61N 5/06–2005/073
USPC .................................... 606/2–19; 607/88–94
See application file for complete search history.

(56) References Cited

U.S. PATENT DOCUMENTS 5,616,140 A * 4/1997 Prescott ............... A61N 5/0616 607/91
2020/0132282 A1* 4/2020 Harmon ............... F16M 11/041

FOREIGN PATENT DOCUMENTS

EP 2637743 B1 * 1/2018 ........... A61N 5/0613

* cited by examiner

*Primary Examiner* — Benjamin J Klein
*Assistant Examiner* — Vynn V Huh

(57) ABSTRACT

Red light therapy devices are disclosed which is substantially more powerful and treats a provided in-contact treatment of a substantially larger area of the human body compared with red light therapy devices previously known in the art. The design is ergonomically versatile, allowing relaxed comfortable treatment of hand, wrist, arm, leg knee, ankle, foot, neck, face, and back. A safety cap for a hand-held red light therapy unit is disclosed. A safety improvement for a hand-held red light therapy unit is disclosed which eases alignment and reduces chance of short-circuit. A bed adapter for stand-up red light therapy panels is disclosed. Flexible light guides for red light therapy treatment are disclosed. An adaptor for adapting a red light therapy head to a clinical treatment stand is disclosed. An open-bottom 3-D-printer-mounted hotbox for increasing the quality of fused deposition modeling 3-D printed parts for red light therapy devices is disclosed.

1 Claim, 36 Drawing Sheets

RED LIGHT THERAPY DEVICES

CROSS-REFERENCE TO RELATED APPLICATIONS

This patent application claims priority to U.S. Provisional Patent Application No. 63/335,162, filed Apr. 26, 2022, and U.S. Provisional Patent Application No. 63/245,907, filed Sep. 19, 2021.

FIELD OF THE INVENTION

The field of the invention relates to LED medical devices, laser medical devices, and more specifically to red and near infrared LED light therapy devices.

BACKGROUND OF THE INVENTION

The application of a therapeutically effective range of intensities of red light and/or near infrared light has been shown to have many beneficial health effects, as documented in books such as "The Ultimate Guide To Red Light Therapy: How to Use Red and Near-Infrared Light Therapy for Anti-Aging, Fat Loss, Muscle Gain, Performance, and Brain Optimization", by Ari Whitten, "Red Light Therapy: Miracle Medicine (The Future of Medicine: The 3 Greatest Therapies Targeting Mitochondrial Dysfunction)", by Mark Sloan, "Low-Level Light Therapy: Photobiomodulation", by Michael R. Hamblin, Cleber Ferraresi, Ying-Ying Haung, Lucas Freitas de Freitas, and James D. Carroll, which are herein incorporated by reference. Beneficial health effects include faster healing of wounds, reduction of inflammation, reduction of pain in joints and tendons, and increased collagen production in skin.

Therapeutic light wavelengths include red light with a wavelength near 660 nanometers, and near-infrared light with a wavelength near 850 nanometers. Within this document, all therapeutic red and infrared light will be referred to as "red light".

Red light therapy products on the market currently include numerous table-top form factors including arrays of light-emitting diodes (LEDs) mounted in or on rigid enclosures intended to project light, where a portion of a user's body can be positioned in front of the array for red light therapy. Currently available products also include clam-shell-style red light therapy beds on which a person can recline, and get red light exposure from below and/or above. Currently available red light therapy products also include hand-held red light units intended to treat joint pain, and hand-held units intended to increase collagen production in skin.

One drawback of tabletop red light therapy arrays, wall-mounted red light therapy arrays, and some red light therapy beds is that much of the light produced is wasted, meaning that it is not absorbed within cells of the body, but rather reflects off the skin and is absorbed by nearby surfaces such as walls, furniture, etc.. Wasted light results in several problems: first, the reduced amount of light entering the tissue means a longer treatment time for tissue which receives a therapeutic dose. Second, penetration depth is reduced for any given tissue treatment light level, thus the depth at which the penetrating light intensity falls to a sub-therapeutic level is decreased. Third, the wasted light may be visually annoying or distracting, or may cause eye strain for persons nearby.

One drawback of low-irradiance hand-held units is that it takes prolonged effort holding the unit in position to achieve the desired therapeutic effect. A drawback of high irradiance hand-held units (units with irradiance in the range of 100 mW/cm2) is that such units can get quite warm during use, and if prolonged use is needed, the user must periodically allow time for the unit to cool before treatment can be continued. A further drawback of hand-held high-irradiance consumer red light therapy units is that although their irradiance does provide sufficient penetration of red light into tissue to treat joints to be therapeutic for many joint problems, such units provide treatment over an area that is only a fraction of the area one might want to treat when treating a large joint such as a knee or a shoulder. A further limitation of many red light therapy units is that they are ergonomically difficult to use to treat areas such as feet, ankles, and back.

A further limitation of high-intensity hand-held red light therapy units on the market is that if placed in a pocket or packed in a hand bag or suitcase, contact between the power switch of the unit and surrounding objects creates the risk of the unit being turned on accidentally, which could result in overheating and possibly injury. It is an object of the present invention to make current hand-held red light therapy devices more safe.

It is an object of the present invention to provide a red light therapy unit with high irradiance (in the range of 100 mW/cm2) that does not become uncomfortably warm during prolonged use. It is a further object of the present invention to provide a red light therapy unit sufficient to treat a large joint such as a knee, without having to move the unit around many times. It is a further object of the present invention to provide a red light therapy unit from which the majority of light output is absorbed in human tissue, and wasted light intensity is significantly reduced so as not to produce eye strain or undue distraction for persons nearby. It is a further object of the present invention to provide a red light therapy unit that is ergonomically easy to use to treat a variety of treatment areas including hands, feet, wrists, arms, legs, knees, hips, shoulders, ankles, and back. It is a further object of the present invention to provide new means for manufacturing red light therapy units and associated equipment.

SUMMARY OF THE INVENTION

The present invention provides a high irradiance red light therapy unit configured in a way that allows it to be used to treat a broader variety of body parts than products previously known in the art, with more comfort and ease of use, and less treatment time needed. The preferred embodiment of the present invention shown in FIG. 2 allows for convenient and comfortable table-top treatment of hand or wrist or elbow, on-floor treatment of feet, and strap-on treatment of arms, shoulders, hips, legs, knees, ankles, and back.

A utility-socket-powered, fan-cooled LED array is contained within a rectangular box housing which is provided with attachments for an elastic strap (or two elastic straps) which can be used to strap the unit to a user's arm, leg, knee, hip, ankle, shoulder, or back. Light from the LED array exits through an externally convex lens, which is positioned to pass light through one surface of the housing so as to provide a curved resting place for treatment of a hand or wrist during tabletop use, and to provide a comfortable resting place for a foot when the unit is placed on the floor.

In a preferred embodiment, the housing also incorporates a timer which can be used to power the unit on for a fixed time, and then power it off. In a preferred embodiment, the housing also incorporates an audio signaling device which signals when treatment time has elapsed, and a thermal sensor that shuts the unit down if a user somehow blocks the air flow through the unit. A preferred embodiment may also provide for remote control, to make treatment time adjustments easy even if the unit is, for example, strapped in place to treat a user's lower back.

In a preferred embodiment, a detachable annular cushion may be attached surrounding the lens to provide a comfortable body contact interface during treatments where the unit is, for example, strapped to a knee, ankle, hip, back, leg, arm, shoulder, etc. or where a convex body part such as an elbow is rested against the annular cushion.

In a preferred embodiment, the annular cushion provides an additional benefit of reflecting the majority of scattered light back to the treatment area. Thus, in a preferred embodiment, the annular cushion is internally reflective of the range of wavelengths being used for treatment, providing either specular reflection of scattered light or non-specular reflection of scattered light, such that the majority of such light is absorbed in tissue under treatment, rather than wasted. The annular cushion may also be referred to herein as a cushioning annulus, or a cushioning light guide, or a flexible light guide.

In another aspect, the present invention includes a foldable detachable stand which enables a user to use the same red light therapy device for non-contact facial red light therapy.

In another aspect, the present invention provides a specially shaped slide-on travel cover for currently available hand-held red light therapy units, which provides the dual benefits of preventing the red light therapy unit from being accidentally turned on, while also protecting the optics of the red light therapy unit from being scratched or broken.

In another aspect, the present invention provides improvements which allow small red light therapy panels to be used in a way that provides improved uniformity of illumination, less scattered light, deeper penetration, and the potential for hands-free operation. The present invention also provided a flexible-bellows light guide, and a strap-anchor-equipped attachable frame for small red light therapy panels.

In another aspect, the present invention provides means to adapt currently available hand-held red light therapy units to provide safe treatment for eyes to improve vision.

In another aspect, the present invention provides means for reducing the operating temperature of a red light therapy head, adapting it for clinical use on a stand with an articulated arm, and further providing a flexible, treatment-efficacy-improving light guide which reduces uselessly scattered light.

In another aspect, the present invention provides means for adapting a stand-up red light therapy panel to provide red light therapy in bed with improved convenience, treatment efficacy, and comfort.

In another aspect, the present invention provides improved means for manufacturing flexible light guides via fused deposition modeling, through improved means for evaporating absorbed and adsorbed water from filament prior to extrusion.

BRIEF DESCRIPTION OF THE DRAWINGS

FIG. 49 depicts a spring-retractable roll-up flexible light guide for use on each side of the red light therapy adapter shown in FIG. 32.

FIG. 50 depicts a tubular metal embodiment of a red light therapy adapter for adapting a red light therapy lamp to provide red light therapy in bed.

DETAILED DESCRIPTIONS OF SOME PREFERRED EMBODIMENTS

Figure 1:
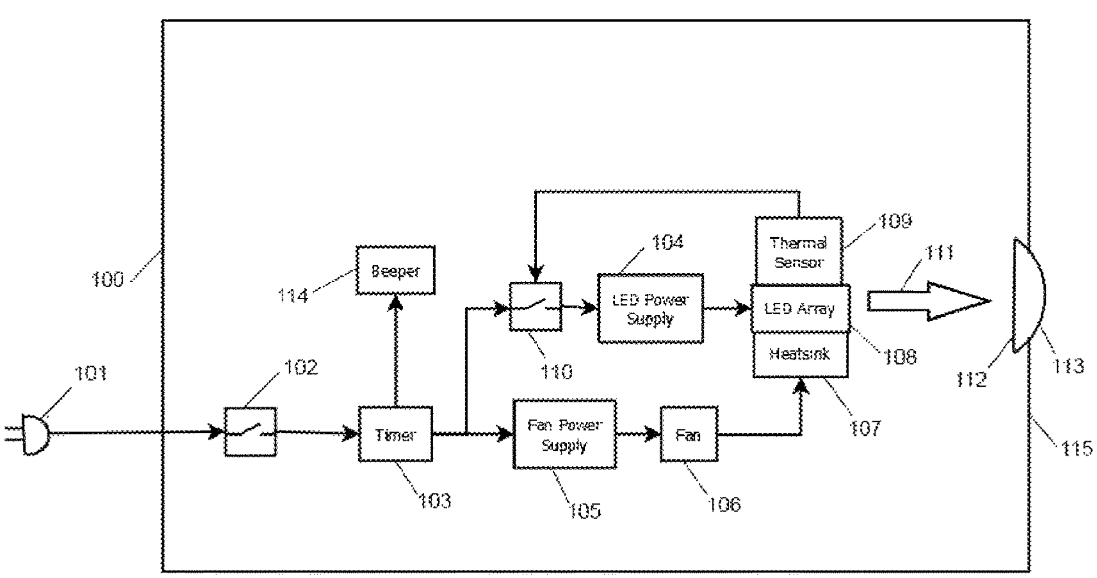
FIG. 1 is a block diagram of a preferred embodiment of the present invention.
Figure 2:
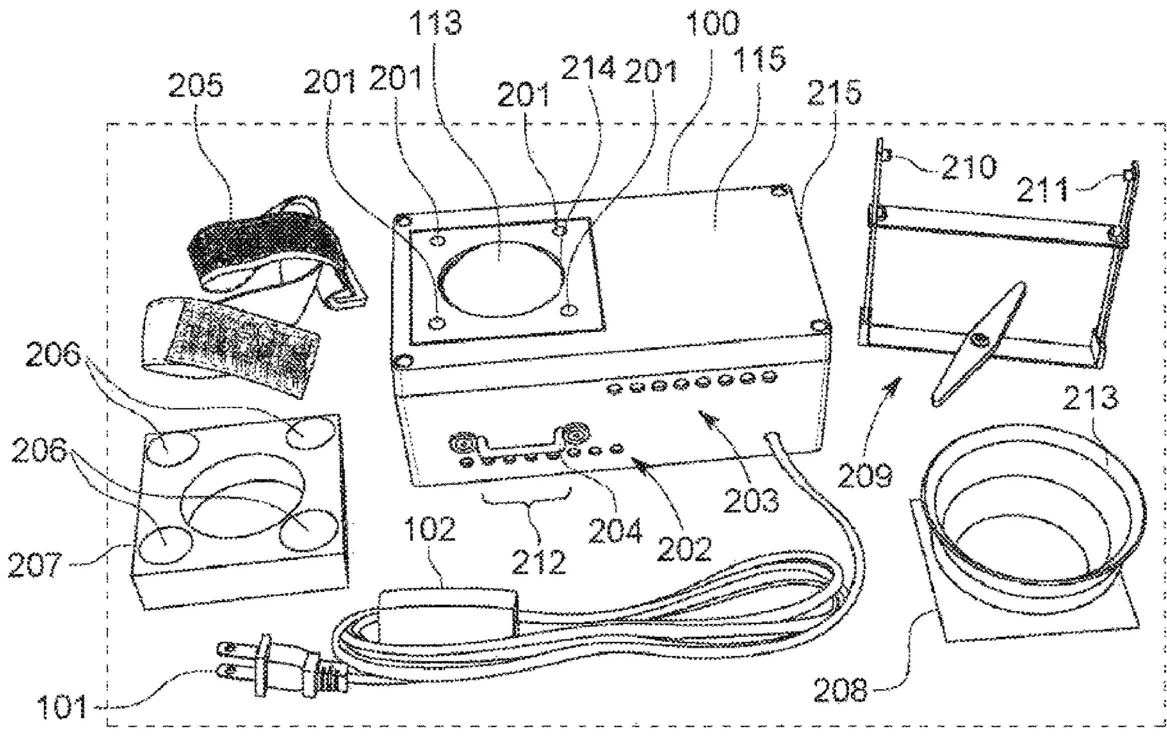
FIG. 2 depicts a perspective view of a preferred embodiment of the present invention, including example closed cell foam cushioning light guide, example bellows cushioning light guide, elastic Velcro strap, and folding stand.
Figure 3:
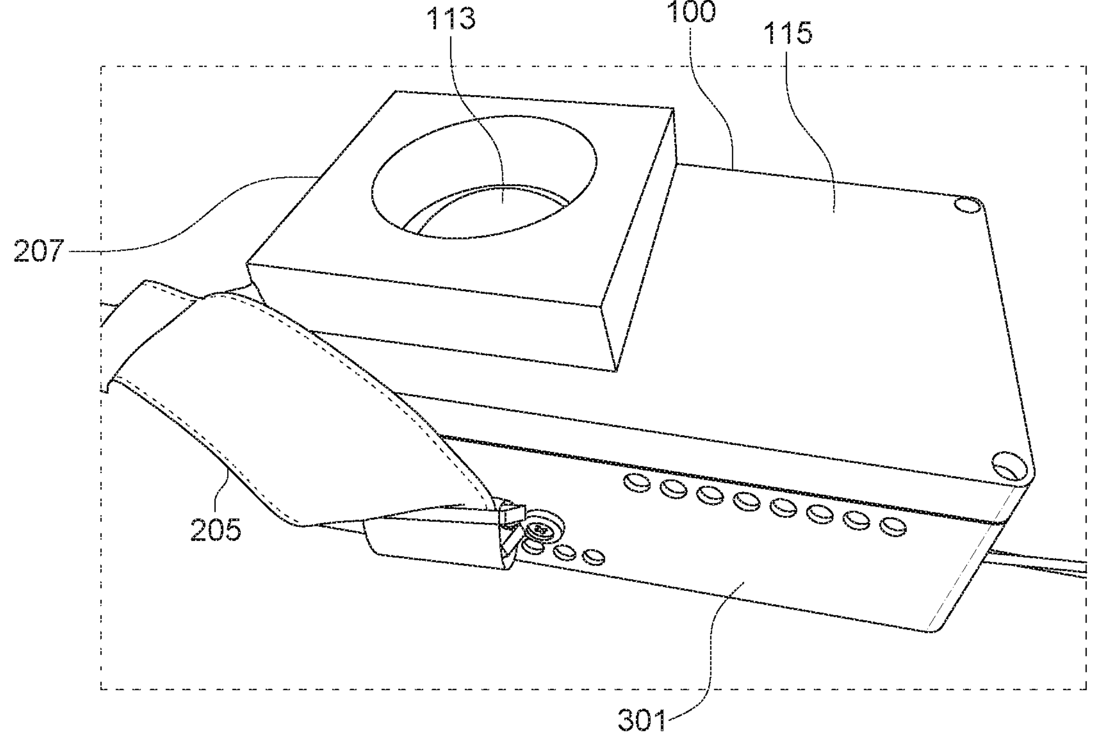
FIG. 3 depicts a preferred embodiment of the present invention configured for tabletop use, with a cushioning annulus installed encircling the lens.

FIG. 1 is a block diagram of a preferred embodiment of the present invention, and FIG. 2 is a perspective view of a preferred embodiment of the present invention, including example closed cell foam cushioning light guide 207, example bellows cushioning light guide 208, elastic Velcro strap 205, and folding stand 209. LED array 108 is mounted within housing 100, and shines red light photons 111 through lens 112 to provide red light therapy to a selected body part of a user. Power is provided from utility plug 101, through manually operated power switch 102. In some embodiments, power switch 102 is external to housing 100, and in other embodiments, switch 102 may be internal to housing 100.

In some embodiments, timer 103 allows a user to set a desired treatment time, and acts as a second power switch in series with power switch 102, while beeper 114 may signal when treatment time has elapsed. In such an embodiment, treatment would start after power switch 102 was turned on, and timer 103 was set and started. In a simpler embodiment, timer 103 and beeper 104 may be absent, and switch 102 may provide power directly to fan power supply 105 and LED power supply 104.

Some embodiments may include over-temperature switch 110, which turns off power to LED array 108 in an overheat condition. In some embodiments, over-temperature switch 110 is implemented as a normally closed thermostatic switch, mounted in thermal communication with heatsink 107. In an embodiment where heatsink temperature is sensed electronically, an electronic heat sensor may be mounted in thermal communication with LED array 108, and may send an electronic signal to open overheat switch 110, which may be implemented as a normally open relay which is closed only when "normal" temperature is sensed. In such an embodiment, thermal sensor 109 is powered by fan power supply 105.

In an embodiment providing timed treatments, audio beeper 114 signals when time has elapsed. This may be useful, for example, if the area of the body being treated is the lower back, where the user cannot see the present invention during treatment. In some embodiments, timer 103 may comprise a remote-controlled switch which is controlled through a Bluetooth connection to a user's smart phone, and the timing function of timer 103 and the audio alert function of beeper 114 may be implemented through software and hardware of the user's smart phone.

In a preferred embodiment, fan or blower 106 draws in air through intake vent holes 202, propels the air through fins of heatsink 107, and out exhaust ventilation holes 203. In a preferred embodiment, intake ventilation holes 202 are provided on at least 3 sides of enclosure 100, so that if clothing fabric or the like accidentally blocks some of intake ventilation holes 202 during use, other of intake ventilation holes will remain unblocked so that sufficient cooling is provided. Likewise, in a preferred embodiment, exhaust ventilation holes 203 are provided on at least 3 sides of enclosure 100, so that if clothing fabric or the like accidentally blocks some of exhaust ventilation holes 203 during use, other of exhaust ventilation holes will remain unblocked so that sufficient cooling is provided.

Figures 5, 6:
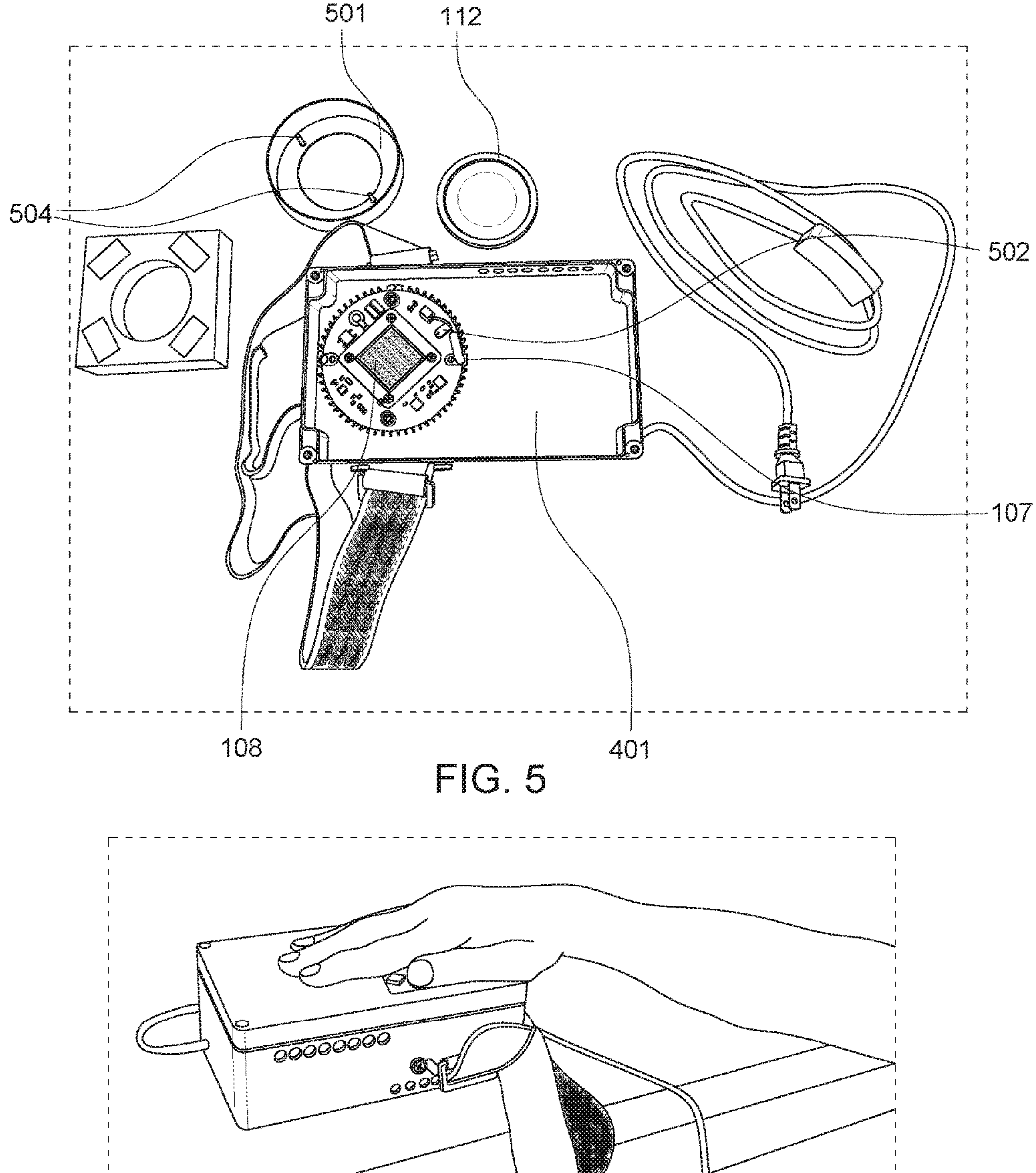
FIG. 5 is a partly disassembled view of a preferred embodiment of the present invention showing how the air duct divider divides the housing into input and output air ducts, and showing the LED power supply and LED array.
FIG. 6 depicts a preferred embodiment of the present invention in use providing red light therapy for a user's palm.
Figure 7:
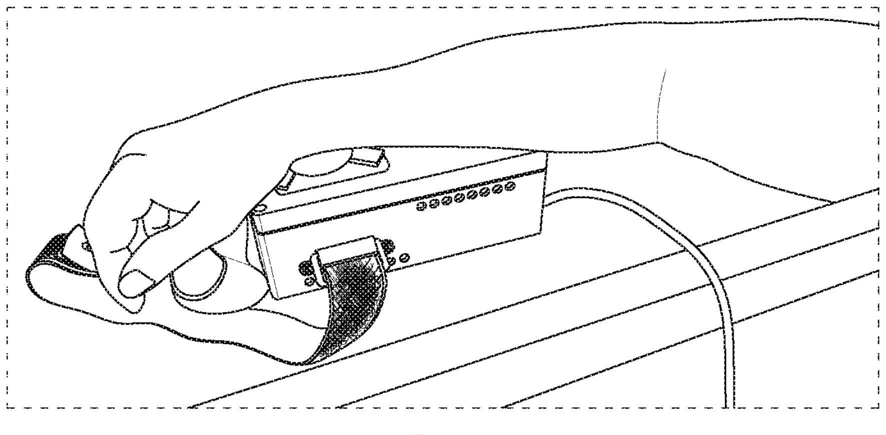
FIG. 7 depicts a preferred embodiment of the present invention positioned for red light therapy treatment of a user's carpal tunnel area and wrist.
Figure 9:
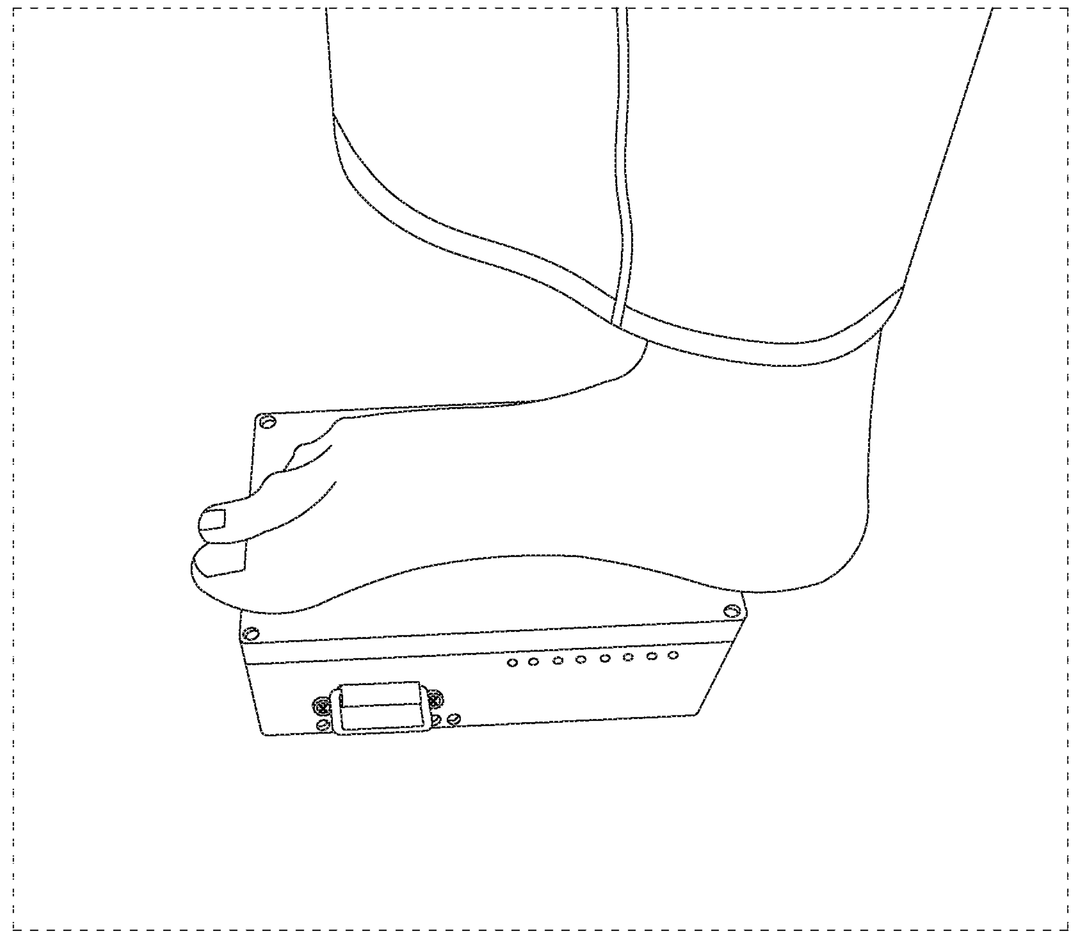
FIG. 9 depicts a preferred embodiment of the present invention in use providing red light therapy for a user's toes, and ball of a user's foot.
Figure 22:
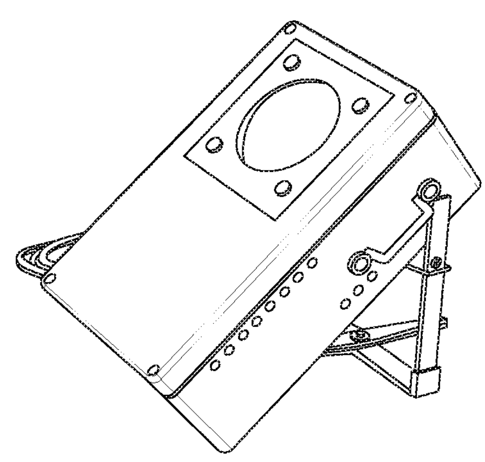
FIG. 22 depicts a preferred embodiment of the present invention assembled with attachable stand, configured to provide facial red light therapy treatment.
Figure 23:
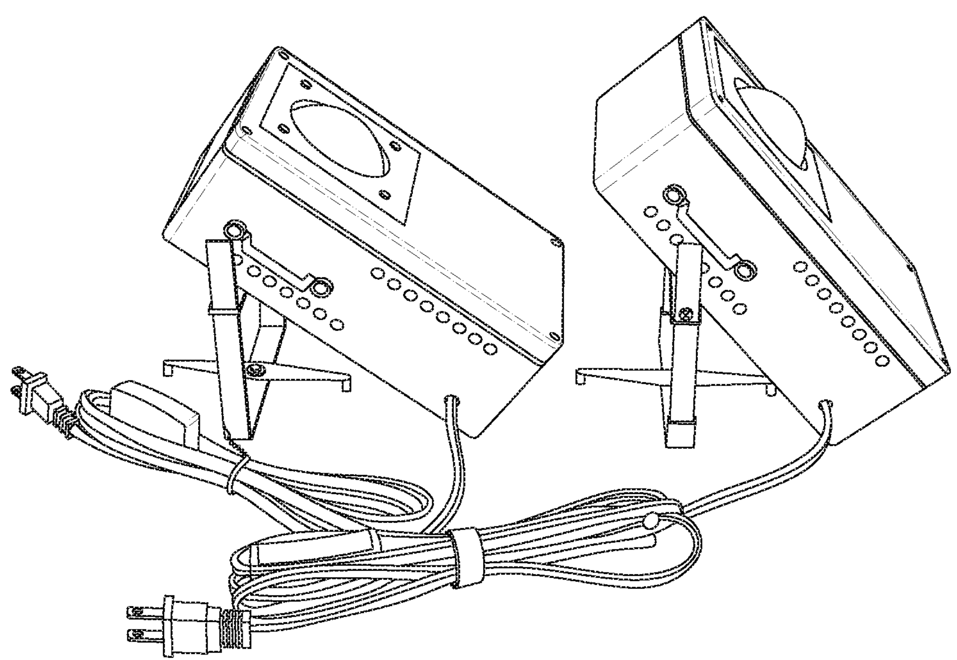
FIG. 23 depicts the range of angles for which a preferred embodiment of the present invention may be configured for providing facial red light therapy.

Numerous external mechanical features of the present invention shown in FIG. 2 provide advantages over prior art red light therapy devices. First, convex outer surface 113 of lens 112 is sized and shaped to provide a comfortable resting place for the palm of the hand, or all the fingers of a hand, allowing the entire palm or all fingers to receive uniform intensity red light therapy at once, comfortably, as shown in FIG. 6. Second, top surface 115 provides an easy place to rest a forearm while treating a wrist or carpal tunnel area, where the wrist or carpal tunnel area rests on lens surface 113, as shown in FIG. 7. Likewise, surface 115 provides a place to rest the heal of a foot while resting the toes or ball of the foot on lens surface 113 for red light therapy treatment, as shown in FIG. 9. Foldable stand 209 allows housing 100 to be angled on a tabletop for treatment as shown in FIG. 22. Foldable stand 209 is removably attachable to housing 100 by inserting engagement nubs 210 & 211 into vent holes 212 on opposite sides of housing 100. The angle of housing 100 relative to a tabletop may be adjusted by choosing which of vent holes 212 engagement nub 210 is inserted into, and likewise which hole on the opposite side of housing 100 engagement nub 211 is inserted into, as shown in FIG. 23, which illustrates the range of angles for which a preferred embodiment may be configured for providing facial red light therapy.

For red light therapy treatments where the intended treatment area is larger than the hole through closed cell foam light guide 207, light guide 207 may be replaced with a flexible bellows-style cushioning light guide such as cushioning light guide 208. In a preferred embodiment, body-contacting rim 213 of bellows light guide 208 is angled away from the center axis of light guide 208, to increase comfort during treatment. Flexible light guide 208 may also be used pro provide containment of a body part being treated, while simultaneously acting as a light guide, for example when providing red light therapy to a man's testicles to increase testosterone.

In a preferred embodiment, a body-contacting flexible light guide such as light guide 208 is manufactured by spiral-vase-printing light guide 208 on a fused deposition modeling (FDM) 3-D printer, using the hot box aspect of the present invention shown in FIGS. 42-48 to evaporate water contained in TPU filament used to 3-D print flexible light guide 213.

Claim language describing flexible light guide 208 might be: a flexible light guide for increasing treatment efficacy of red light therapy for increasing testosterone production in bale testicles, comprising: a circularly symmetric flexible polymer bellows structure with a light input end and a light output end, configured to adapt a red light source to male testicles; wherein said bellows structure either slides frictionally over a cylindrical red light therapy head, or wherein said bellows structure attaches to a planar surface via an integral flexible polymer section removably affixable to a planar surface surrounding a red light therapy optical output aperture.

Figure 8:
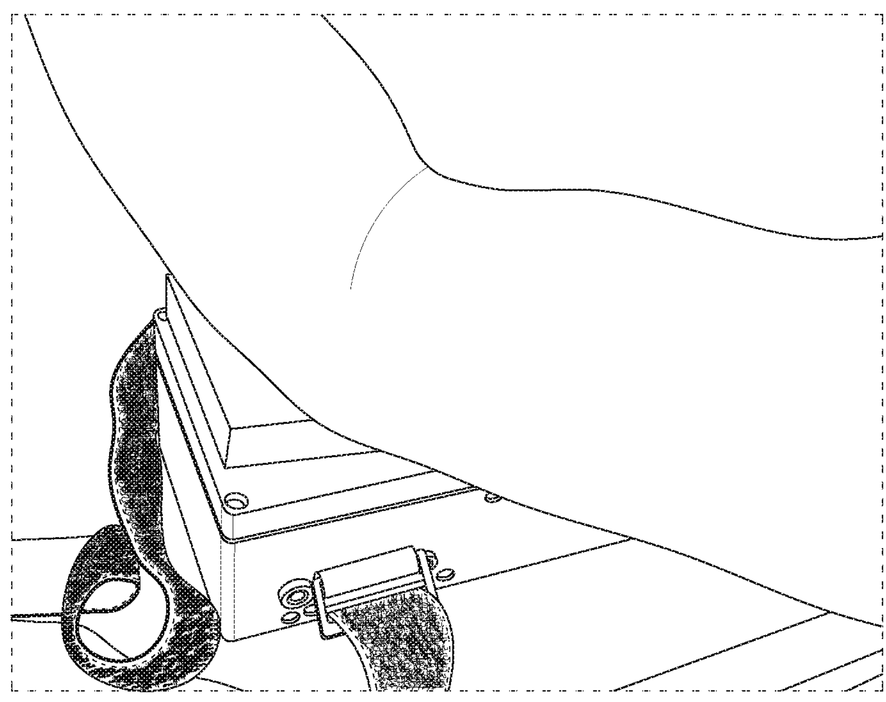
FIG. 8 depicts a preferred embodiment of the present invention configured for providing red light therapy for a user's elbow.
Figure 10:
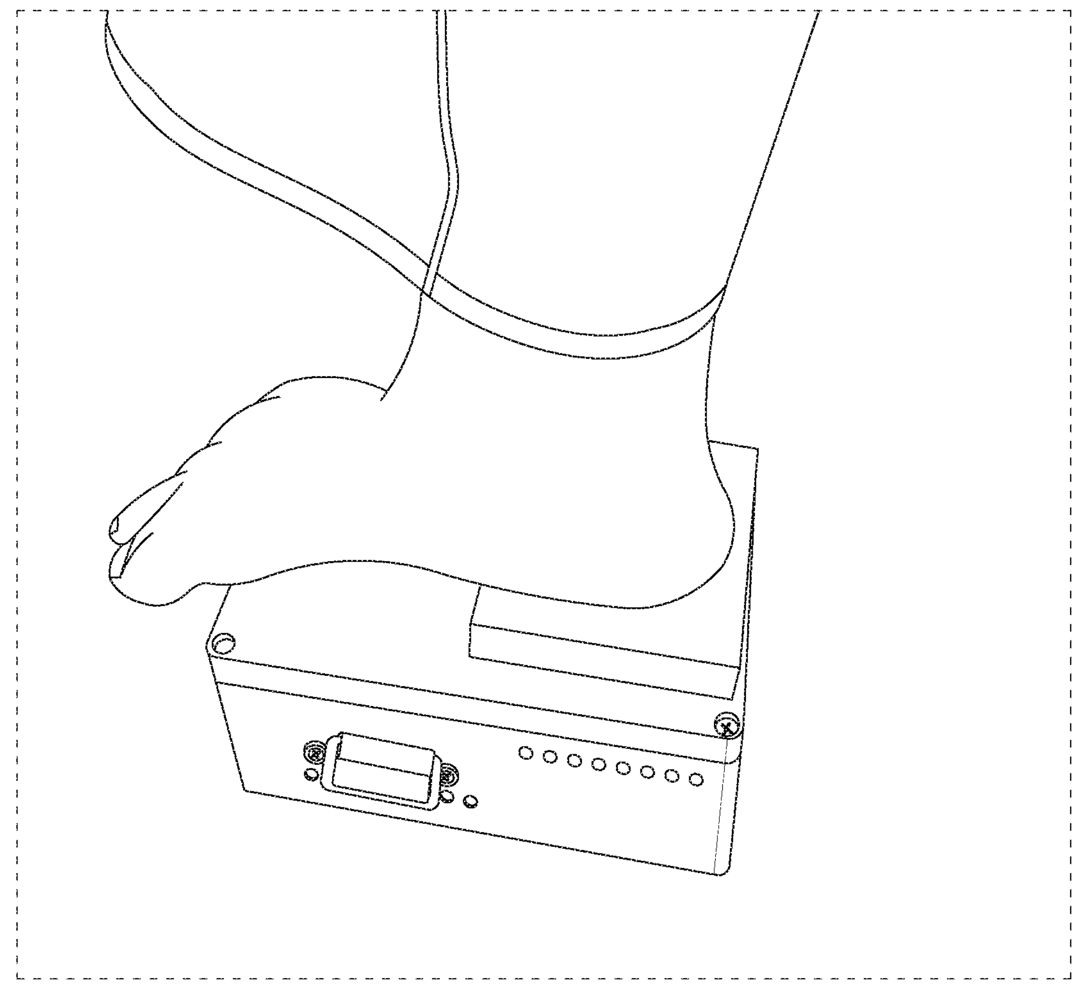
FIG. 10 depicts a preferred embodiment of the present invention configured for providing red light therapy to the heal of a user's foot.
Figure 18:
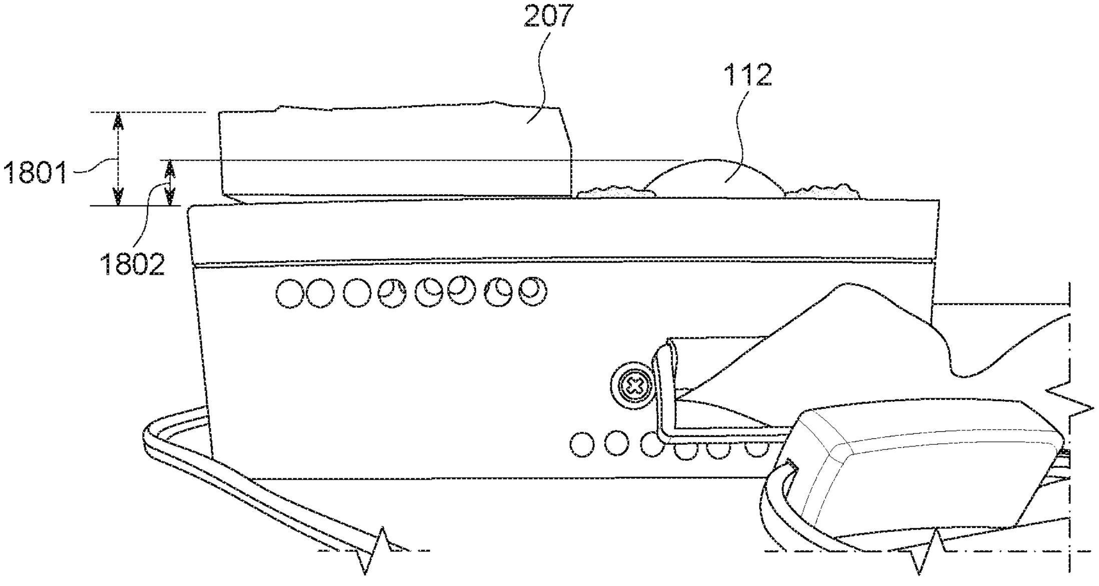
FIG. 18 is a side view of a preferred embodiment of the present invention.

In a preferred embodiment, annular cushion/light guide 207 is made from die cut closed-cell polyethylene foam, and has a thickness 1801 (see FIG. 18) greater than the distance 1802 (see FIG. 18) which lens 112 protrudes through surface 115, perpendicular to surface 115. Annular cushion 207 includes Velcro hook attachments 206, which mate with Velcro loop attachments 201, allowing annular cushion/light guide 207 to be removably attached circumferentially around lens surface 113, providing a comfortable resting place for table-top red light therapy treatment of an elbow, as shown in FIG. 8, and providing a comfortable resting place for the heal of a foot to receive red light therapy when the present invention is positioned on the floor as shown in FIG. 10. In alternate embodiments, alternate means for removable attachment may be employed, such as snaps, magnets, one or more zippers, removable adhesive, or other means of removable attachment, and the term "removably attachable annular cushion" shall be construed to mean an annular cushion including at least one such means of removable attachment.

Figure 17:
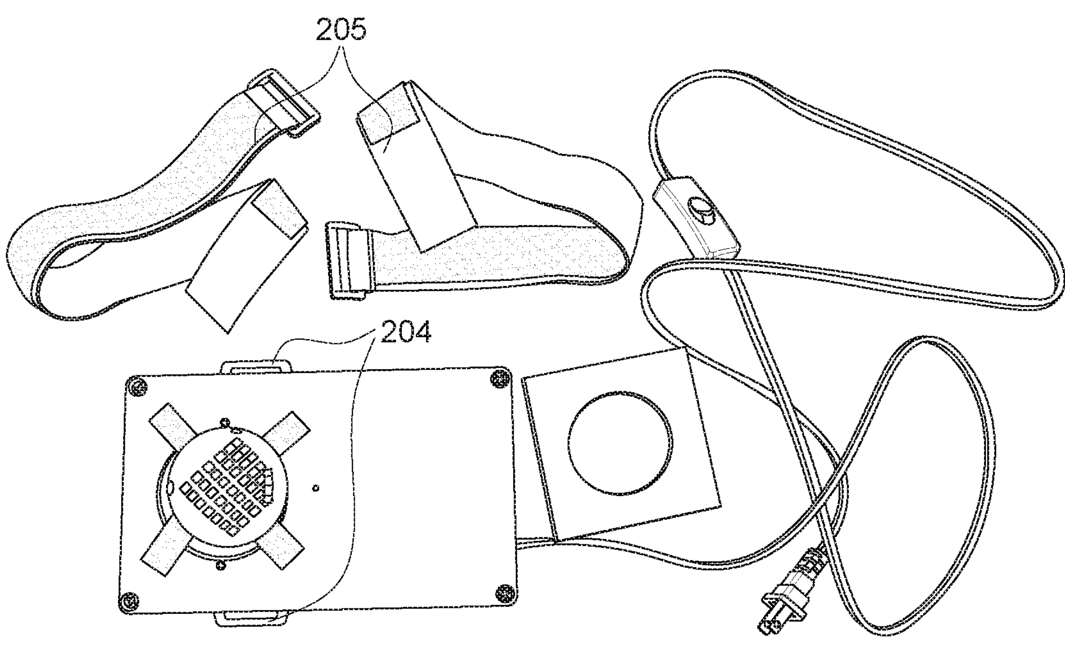
FIG. 17 is a top view of a preferred embodiment of the present invention with straps detached and both strap attachment anchors visible.

In a preferred embodiment, strap attachment anchors 204 (see FIGS. 2 and 17) facilitate attachment of one or two Velcro straps 205. Strap anchors 204 are configured to facilitate strapping the present invention to the body so that the user may engage in other activities during red light therapy, without the need to hold the present invention in a desired position manually, and without the need to pay attention to the area undergoing red light therapy. If two straps are used, each is attached to one of strap anchors 204, and the two straps are overlapped and Velcro-attached to one another after wrapping around the user's torso or other body part targeted for red light therapy.

In a preferred embodiment, annular cushion 207 not only facilitates comfort when the present invention is positioned or secured in contact with the body, but also facilitates reflecting scattered light back to the treatment sight, such that the majority of red light emitted from lens 112 is absorbed in body tissue. This increases the effective strength and effective depth of the treatment, decreases required treatment time, reduces wasted light, and decreases the potential for a user to be distracted from other activities by the presence of bright scattered light in the treatment area.

Figure 11:
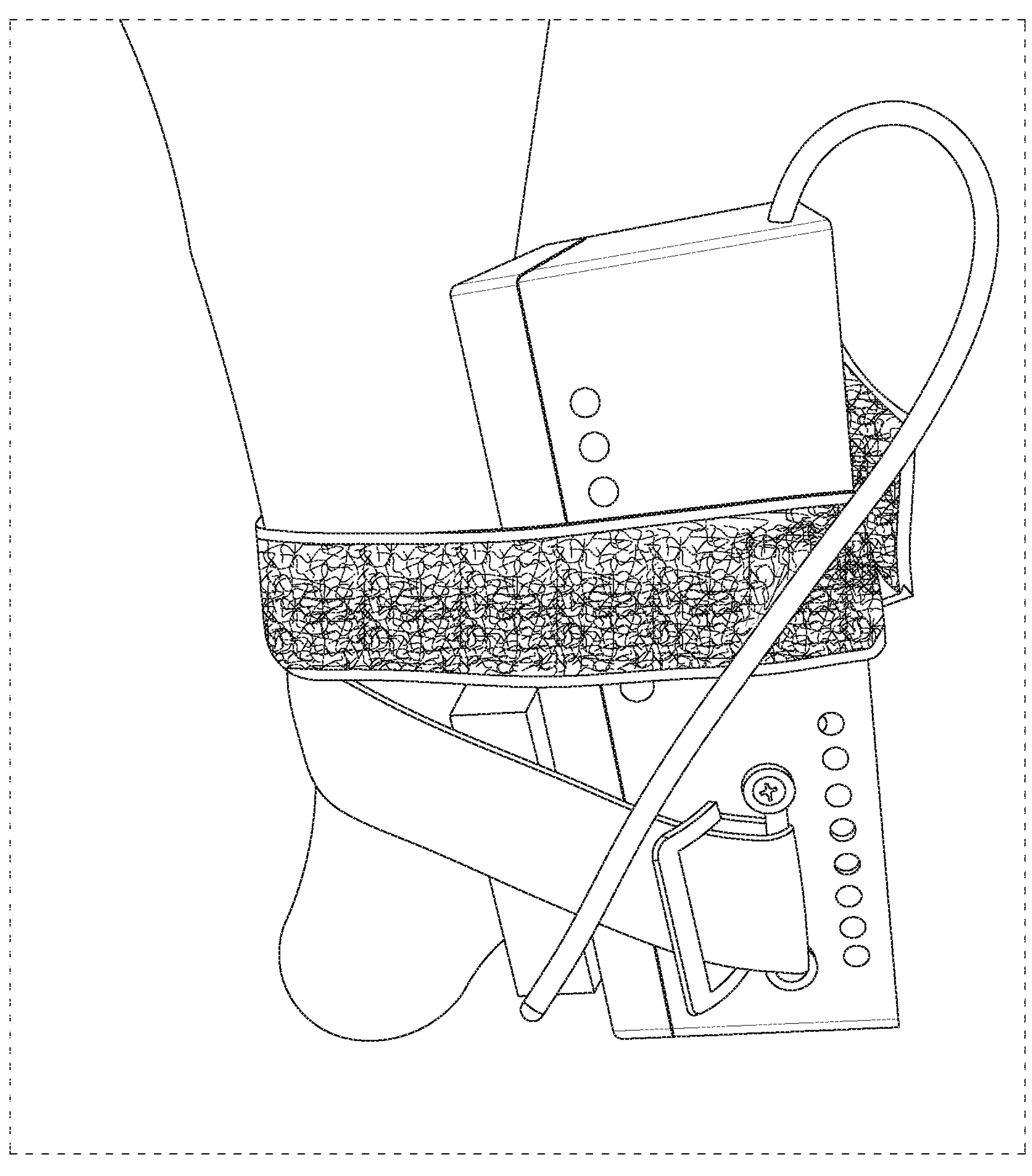
FIG. 11 depicts a preferred embodiment of the present invention configured for providing red light therapy to a user's ankle.
Figure 12:
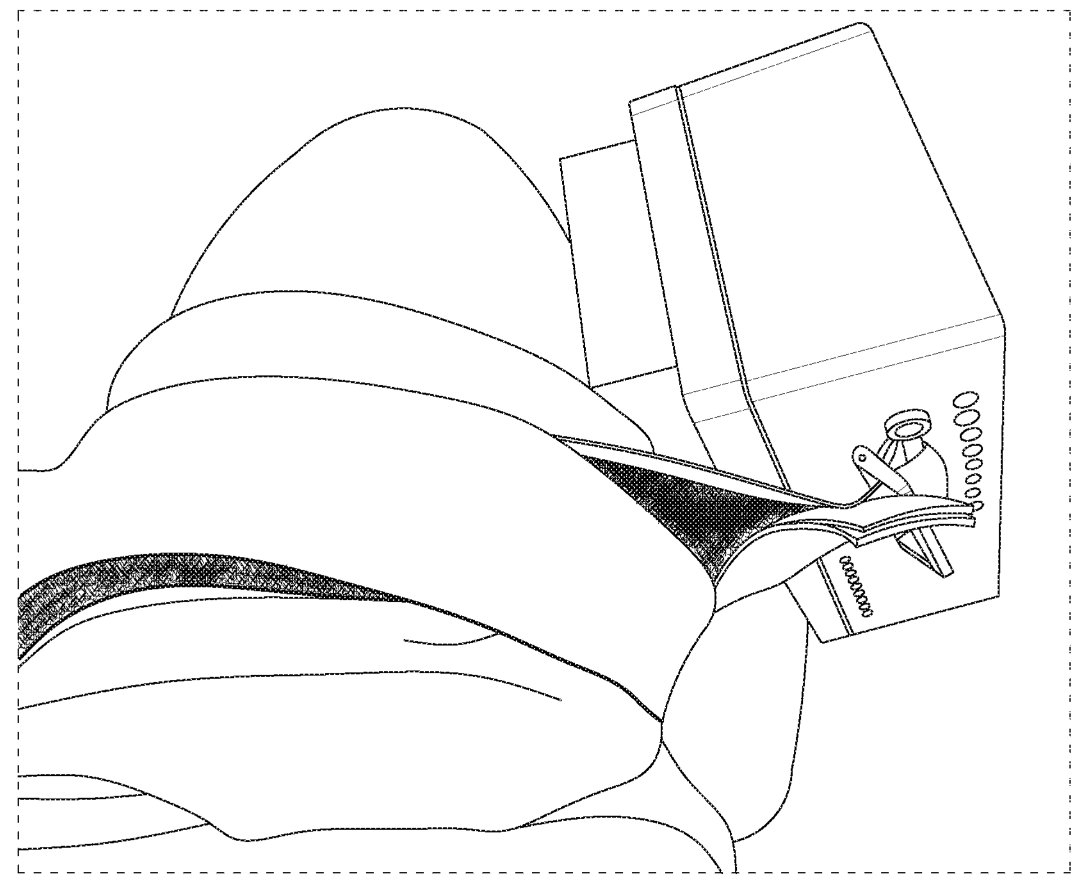
FIG. 12 depicts a preferred embodiment of the present invention configured for providing red light therapy to a user's knee.
Figure 13:
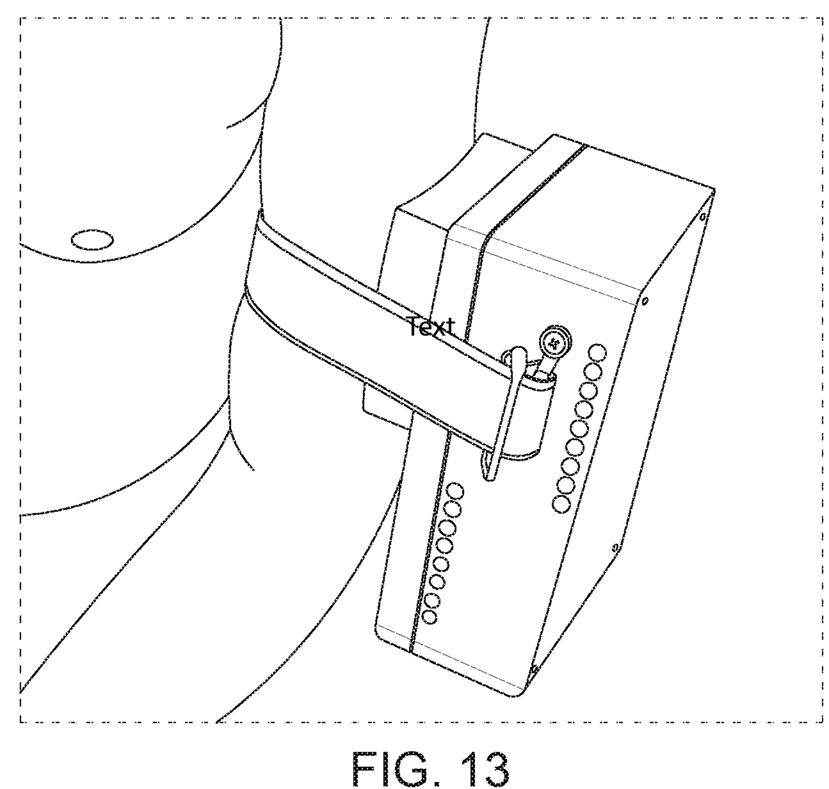
FIG. 13 depicts a preferred embodiment of the present invention configured for providing red light therapy to a user's arm.
Figure 14:
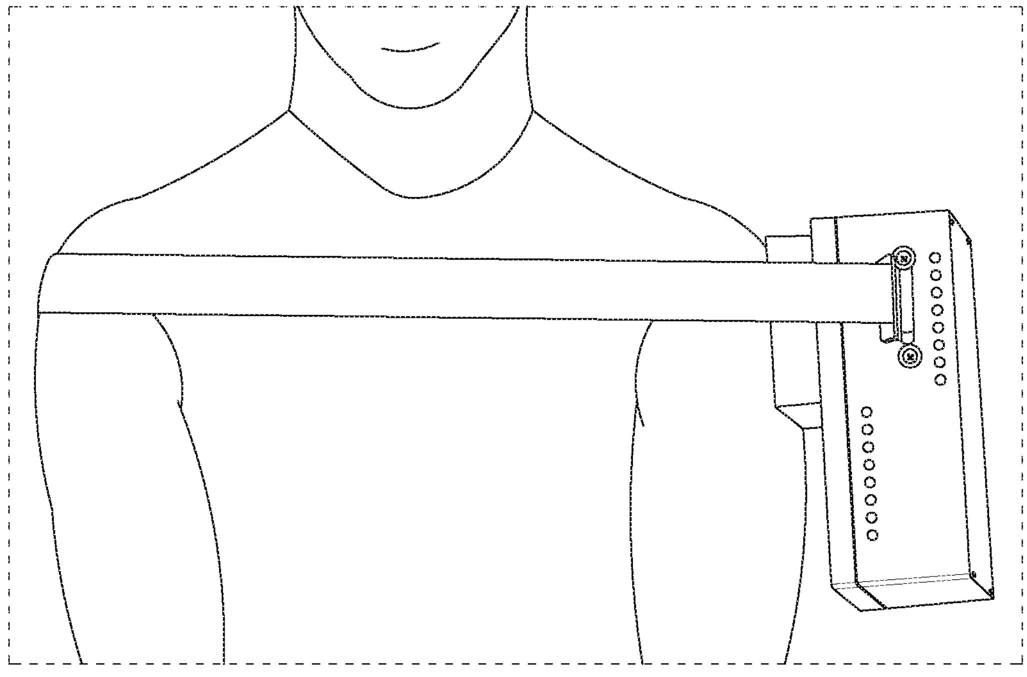
FIG. 14 depicts a preferred embodiment of the present invention configured for providing red light therapy to a user's shoulder.
Figure 15:
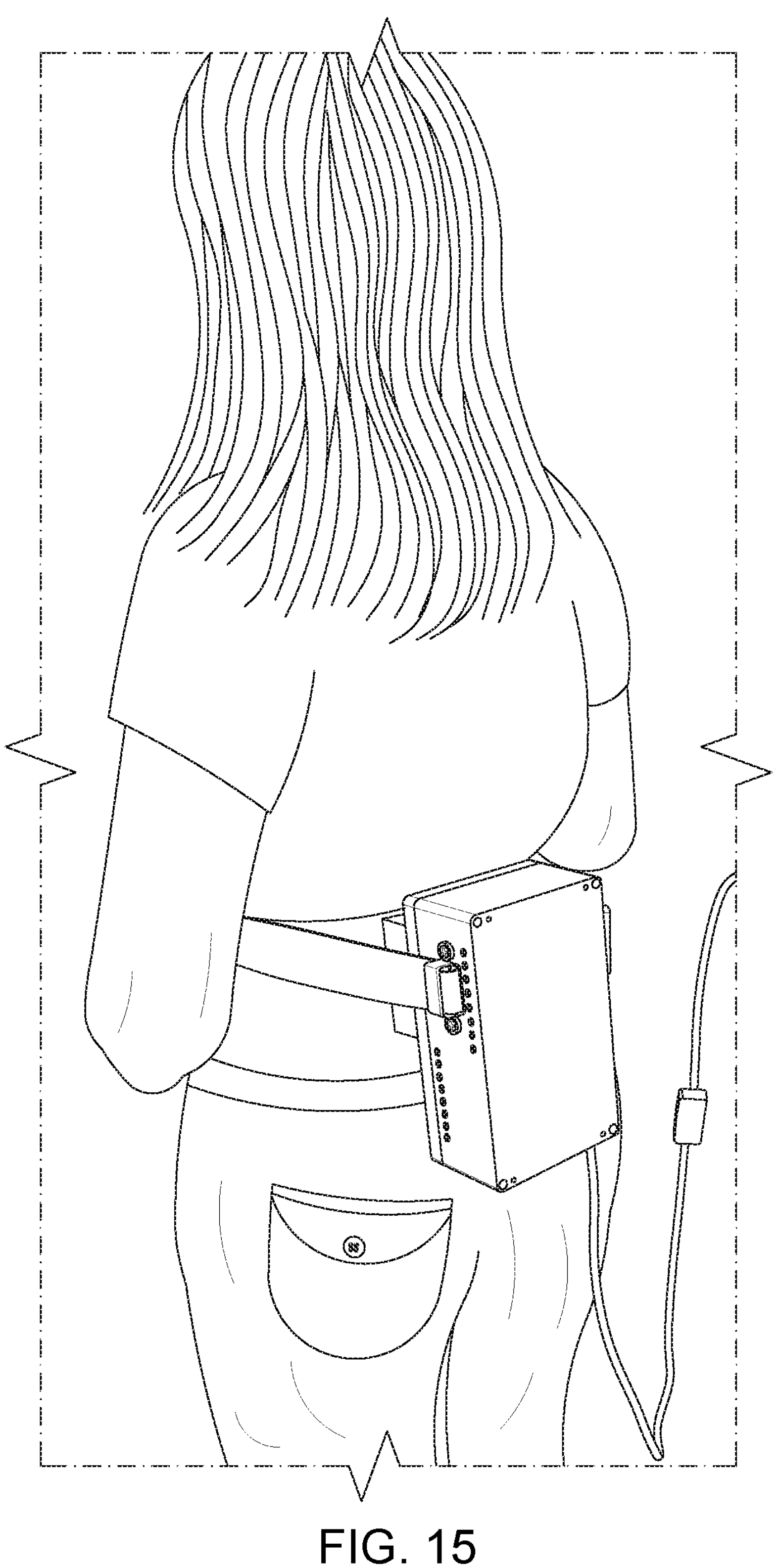
FIG. 15 depicts a preferred embodiment of the present invention configured for providing red light therapy to a user's lower back.
Figure 16:
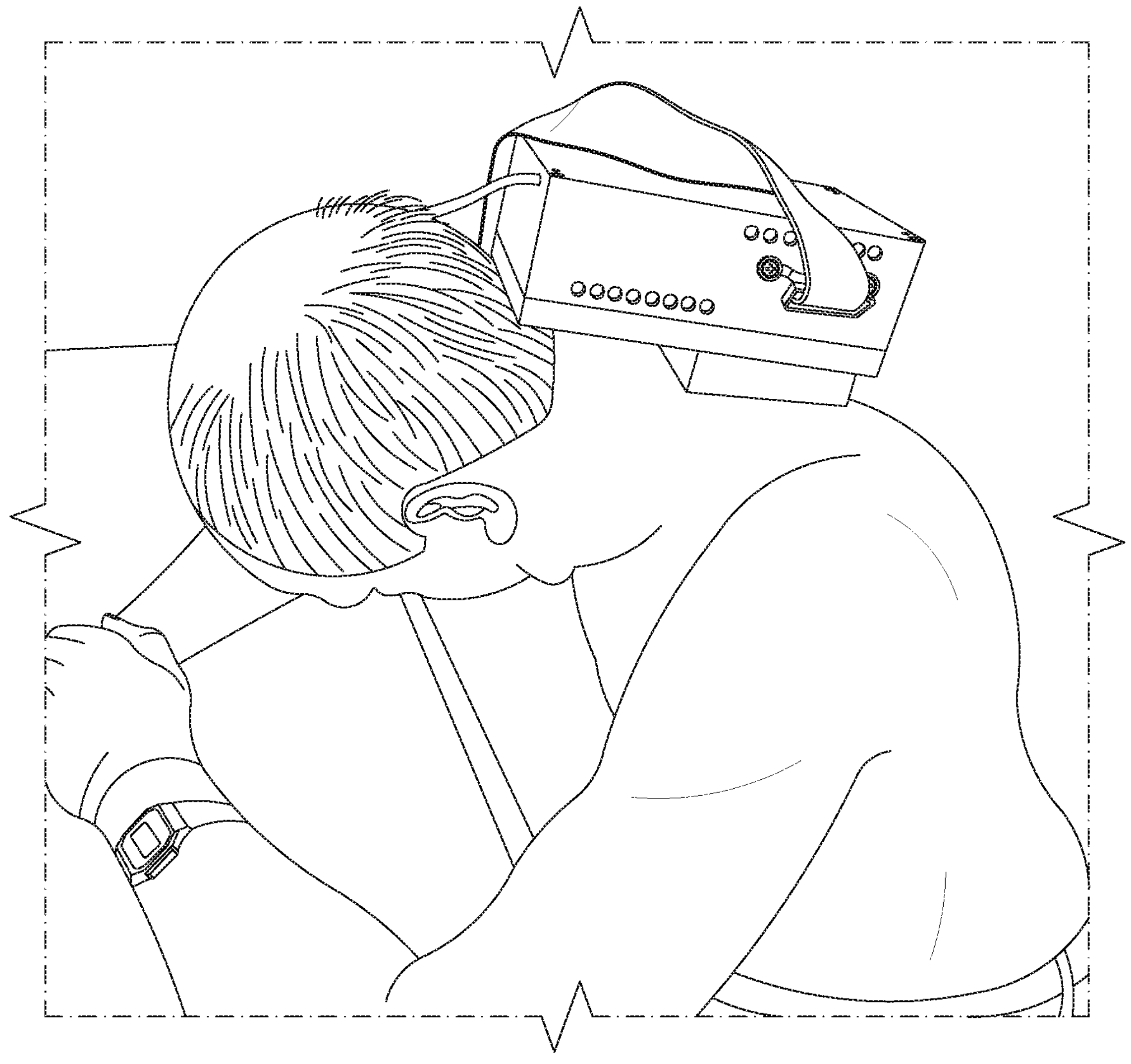
FIG. 16 depicts a preferred embodiment of the present invention configured for providing red light therapy to a user's neck.

Strap anchors 204 and Velcro straps 205 enable the present invention to be strapped to the body for treatment of an ankle (see FIG. 11), knee (see FIG. 12), arm (see FIG. 13), shoulder (see FIG. 14), or back (see FIG. 15). In a preferred embodiment, each strap 205 is elastic, and the majority of the length of each strap 205 is covered on one surface with Velcro loop fastener material, while a patch of Velcro hook material is attached at the end of the strap farthest from anchor 204. When attaching housing 100 to a small-diameter limb such as an arm, one strap may be used, engaging each of anchor points 204 at opposite ends of the strap. When attaching housing 100 to a larger-diameter portion of the body such as the torso, both straps may be used, and overlapped to join with at least the Velcro hooks of one strap engaging the Velcro loops of the other strap.

Figure 19:
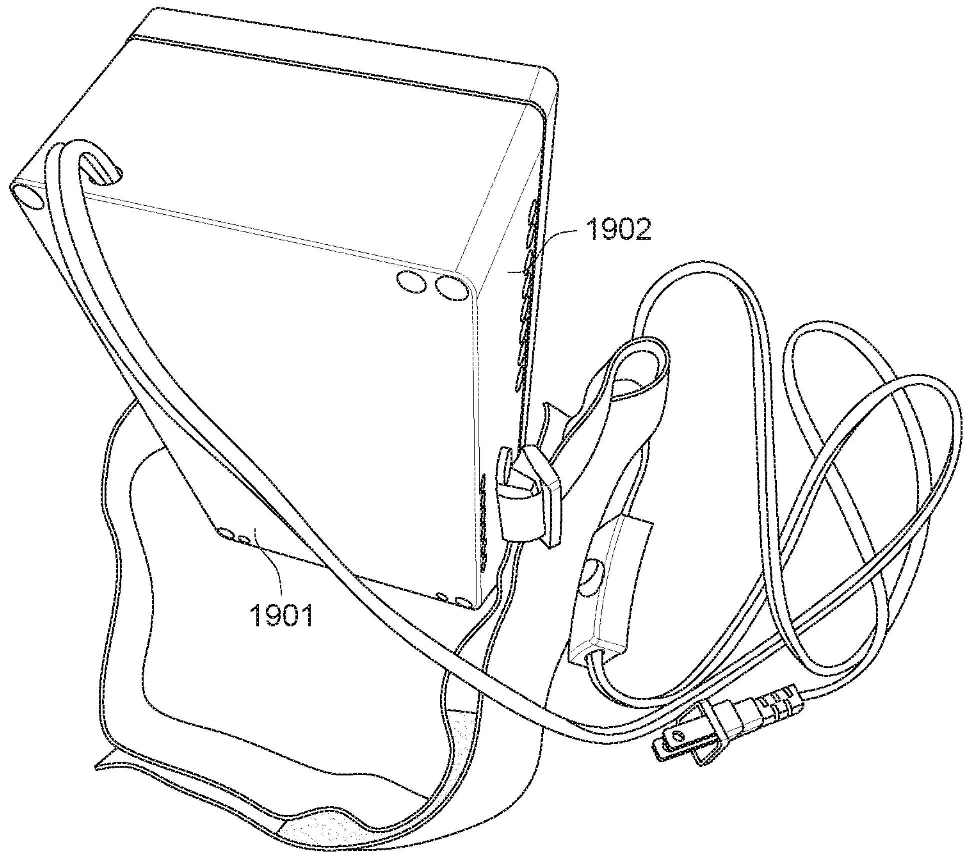
FIG. 19 is a bottom perspective view of a preferred embodiment of the present invention.

In a preferred embodiment, two strap anchors 204 are provided, one affixed to or a molded part of side surface 1101 (see FIG. 11), and one affixed to side surface 1902 (see FIG. 19). In a preferred embodiment, strap anchors 204 are disposed symmetrically about a plane containing the optical axis of lens 112. In the a preferred embodiment, anchors 204 are mounted on enclosure sides 301 and 1902. In preferred embodiments, strap anchors 204 may be attached to housing 100, or may be a molded feature integral to housing 100.

In a preferred embodiment, optical opening 214 allows a convex portion of lens 113 to protrude through top surface 115. LEDs in LED array 108 are designed with optical output patterns and spaced apart at distances such that, given the distance between LED array 108 and top surface 115, light passing through opening 214 is uniform to such a degree that no matter what two places on the outer surface of lens 113 one measures light flux through two half-inch-diameter circles, the light flux measured in such two circles will never differ by more than a factor of two. We herein define a contiguous optical aperture with such light uniformity to be a "good-uniformity optical aperture".

Preferentially, LEDs in LED array 108 are designed with optical output patterns and spaced apart at distances such that, given the distance between LED array 108 and top surface 115, light passing through opening 214 is uniform to such a degree that no matter what two places on the outer surface of lens 113 one measures light flux through two quarter-inch-diameter circles, the light flux measured in such two circles will never differ by more than a factor of two. We herein define a contiguous optical aperture with such light uniformity to be an "optimum-uniformity optical aperture".

To increase clarity, it should be noted that the boundary of optically transparent opening 214, and the boundary of lens 112, and the boundary of LED array 108, and the boundary of a good-uniformity optical aperture created by a particular spatial arrangement of those components are different things. Likewise, for such a given particular spatial arrangement, the boundary of an optimum-uniformity optical aperture created is a different boundary than the boundary of the good-uniformity optical aperture created. The good-uniformity and optimal-uniformity optical apertures are contiguous areas (coincident with the surface of the combination of enclosure 100 and, if present, lens or transparent window 113) whose boundary is defined by the uniformity constraints put on the light that passes through those apertures, whereas optically transparent opening 214 is a boundary between a material that is optically transparent, such as clear plastic or glass, or air) and a material that is not transparent (such as opaque plastic or metal).

In a preferred embodiment, the centroid of optical opening 214 is positioned within top surface 115 such that the longest distance from the centroid to any point on top surface perimeter 215 is at least four inches, providing a stabilizing effect when strapping housing 115 to a portion of a human body.

In an preferred embodiment alternate to that shown in FIGS. 1 and 2, lens 113 is formed by a flat transparent window within perimeter 214, and a good-uniformity optical aperture is formed by the purely by the placement of LEDs in LED array 108, by the individual optics of the LEDs in LED array 108, and by the relative placement of LED array 108 with respect to the transparent window defined by optical opening 214. In such a preferred embodiment, the preferred area of the good-uniformity optical aperture formed is greater than three square inches.

Figure 4:
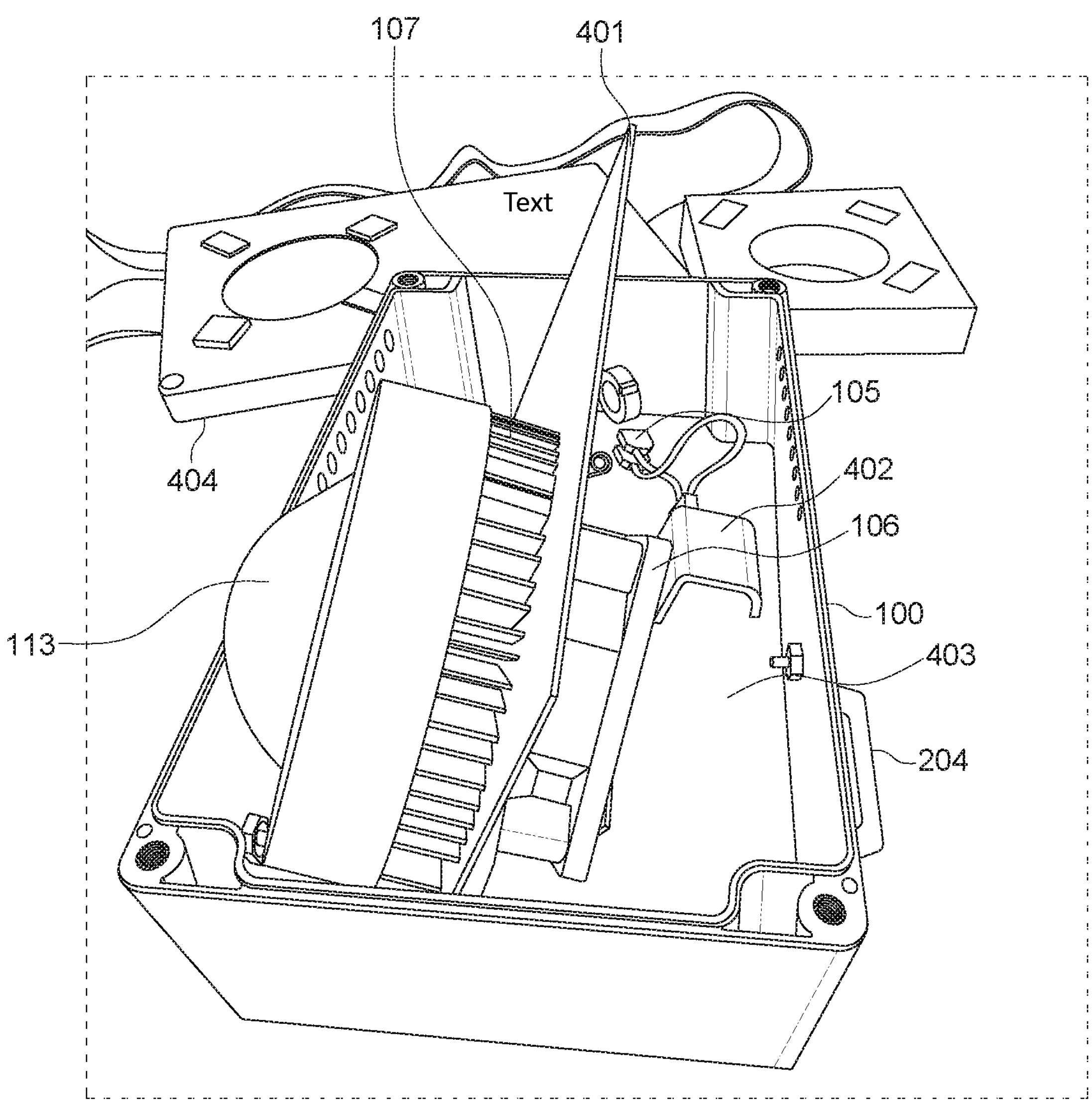
FIG. 4 is a partly disassembled view of a preferred embodiment of the present invention, showing assembly of the fan, air duct divider, heat sink, and lens.

FIGS. 4 and 5 show partially disassembled views of a preferred embodiment of the present invention. Heatsink 107 is sandwiched between fan 106 and metal core printed circuit board (MCPCB) 502, on which an array of surface-mount LEDs 108 is mounted. In an alternate embodiment, LED chips may be bonded directly to a metallic substrate, forming a chip-on-board (COB) array. Components of LED power supply 104 are mounted directly on MCPCB 502. In a preferred embodiment, both fan power supply 105 and LED power supply 104 are non-isolated line-voltage-input switching power supplies, as multiple levels of electrical isolation are provided by the MCPCB insulation, and the insulating housing 100.

In a preferred embodiment, when housing 100 is assembled, air-ducting baffle 401 separates the internal space of housing 100 into an air intake duct, and an air exhaust duct. Mechanical standoffs 402 hold the intake side of fan 106 a fixed distance off bottom inner surface 403. Lens clamping member 501 is attached by screws 504 to threaded attachments 503 on heatsink 107, centering lens 112 over MCPCB 502 and heatsink 107. The layered assembly comprising, in order, lens-clamping annulus 501, lens 112, MCPCB 502, heatsink107, ducting-forming baffle 401, fan 106, and standoffs 402, is clamped in compression after assembly between inner bottom surface 403 and lid 404.

FIG. 19 is a bottom perspective view of a preferred embodiment of the present invention, showing bottom surface 1901, which may be conveniently and stably positioned on a tabletop for treatments such as shown in FIGS. 6, 7, and 8, and may be conveniently and stably positioned on the floor for treatments such as shown in FIGS. 9 and 10.

Figure 20:
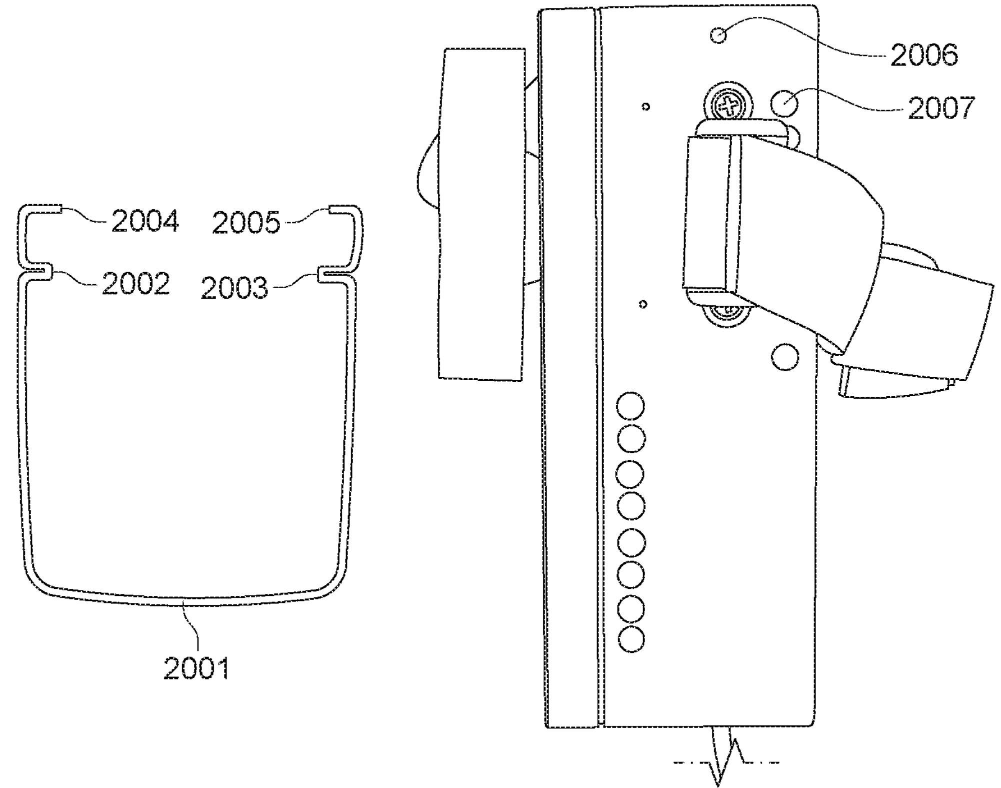
FIG. 20 depicts a preferred embodiment of the present invention including a detachable wire stand which may be used to facilitate red light therapy treatment of a user's face.
Figure 21:
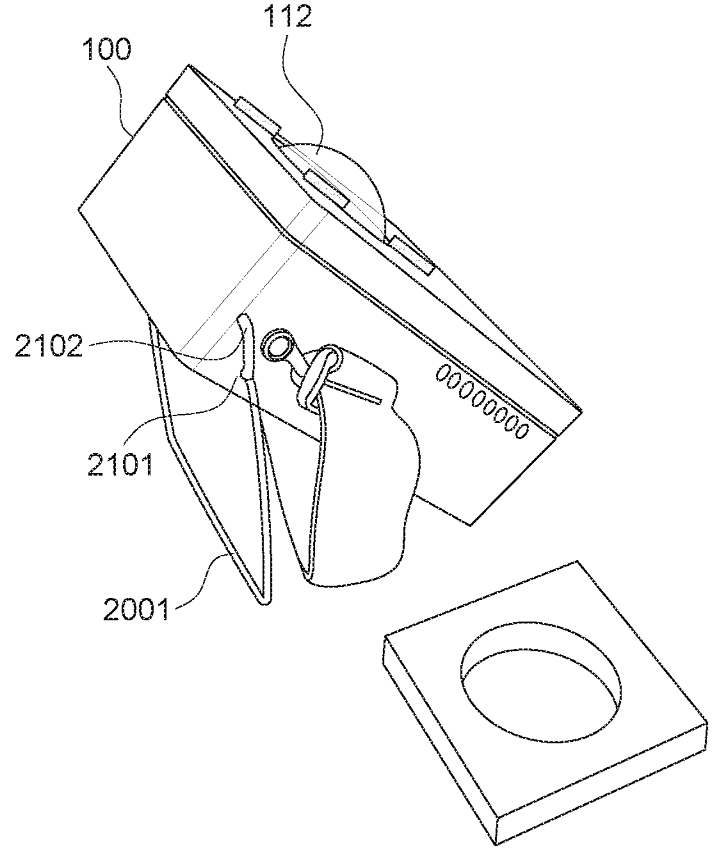
FIG. 21 shows a preferred embodiment of the present invention configured to provide red light therapy to a user's face.

FIGS. 20 and 21 depict a detachable bent-wire stand aspect of a preferred embodiment of the present invention. Detachable bent-wire stand 2001 includes protrusions 2002, 2003, 2004, and 2005 which mate with features on housing 100 to configure the present invention for convenient non-contact red light therapy treatment of a user's face. To attach bent-wire stand 2001 to housing 100, the user inserts protrusions 2002 and 2004 into holes 2007 and 2006 in housing 100, and inserts protrusions 2003 and 2005 into holes 2101 and 2102, configuring the present invention for tabletop non-contact red light therapy as shown in FIG. 21. To undergo maximum-strength facial red light therapy, a user positions the present invention on a tabletop as shown in FIG. 21, and the user sits with face positioned along the optical axis of lens 112, at a distance such that the edges of the cone of red light projected from lens 112 coincide with the edges of the user's face.

In alternate embodiments, U-shaped detachable stand 2001 may be formed of a bent flat bar of metal, or an injection-molded piece of plastic, or the like. In alternate embodiments, stand attachment features 2002, 2003, 2004, and 2005 may be replaced by other means for detachable fastening, such as snaps, Velcro, magnets, zippers, or some combination thereof. The primary reason for attachment points 2006 and 2102 is to prevent stand 2001 from rotating about attachment points 2007 and 2101. Thus if in an alternate embodiment, attachment at attachment points 2007 and 2101 is accomplished in a manner that prevents stand 2001 from rotating about attachment points 2001 and 2101 (for instance by making protrusions 2002 and 2003 star-shaped, and making attachment features 2007 and 2101 mating star-shaped holes), then attachment features 2004, 2005, 2006, and 2102 are not needed.

In the above described embodiments, convex surface 113 of lens 112 provides a curved surface on which a user may comfortably rest a hand, fingers, foot, or toes, while body tissue receives uniform illumination during red light therapy treatment. The preferred radius of curvature for such curved resting surface is between 30 mm and 100 mm. An embodiment with less uniform optical output and similar curved surface might, for instance, be a similarly shaped curved resting surface comprising multiple optical ports. each projecting light from an individual LED. In each case, the curved surface allows light from LEDs contained within the housing to pass through to provide red light therapy to the body part placed against or near the curved surface.

Embodiments described above have assumed a utility power source, but similar embodiments might employ batteries as a power source, though that might increase weight and cost, and the batteries would impose a limit on the amount of time the unit could provide red light therapy prior to needing to have the batteries recharged or replaced.

Figure 24:
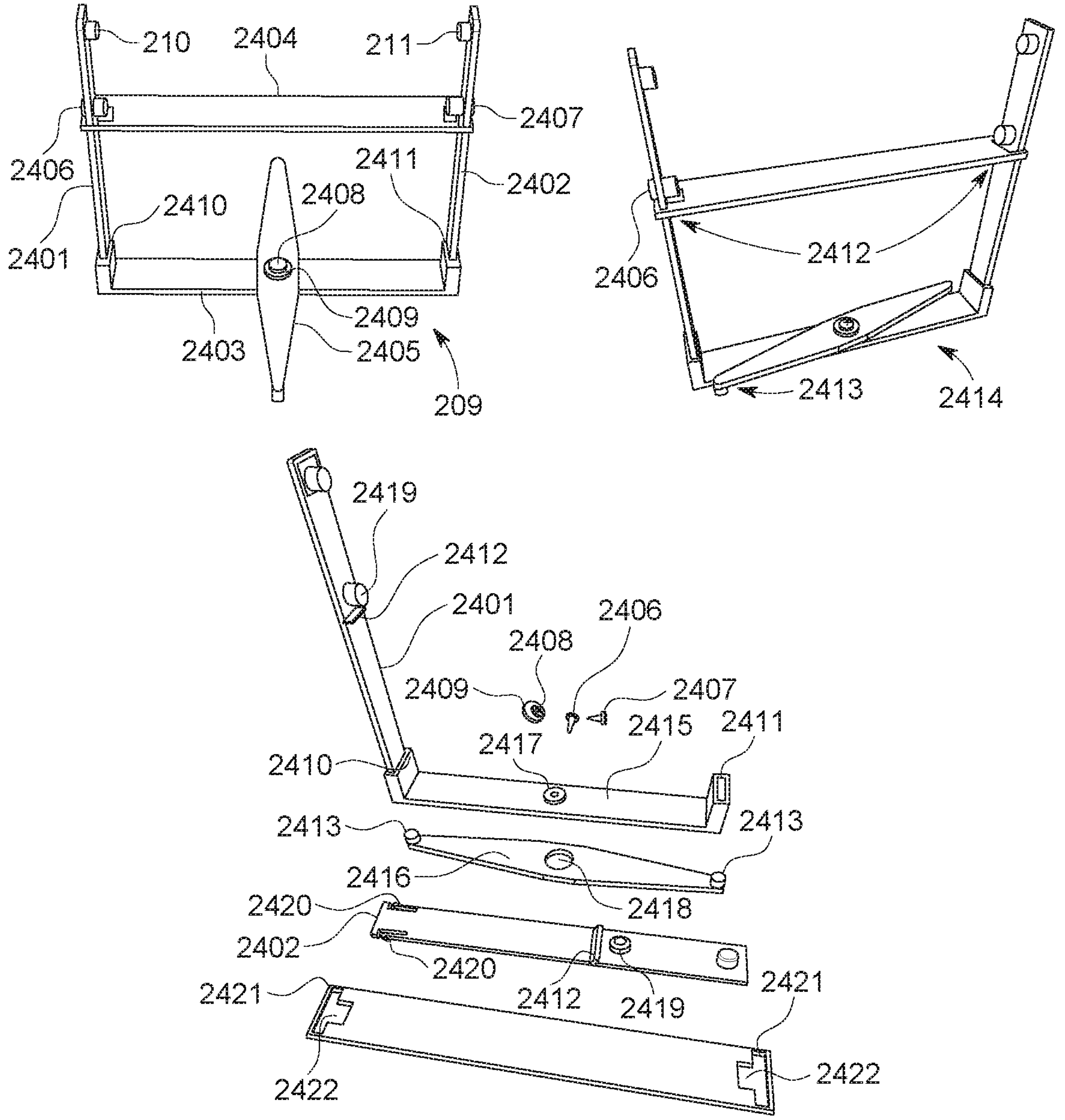
FIG. 24 depicts an unfolded view, a folded view, and a partly disassembled view of a foldable stand according to one aspect of a preferred embodiment of the present invention.

FIG. 24 depicts an unfolded view, a folded view, and a partly disassembled view of a foldable stand according to one aspect of a preferred embodiment of the present invention. The stand is made up of five plastic parts, which may be injection molded or 3-D printed. In use, vertical support members 2401 & 2402 support part of the weight of red light therapy unit housing 100 on engagement nubs 210 & 211. Stand 209 is attached to housing 100 by bending arms 2401 and 2402 away from each other at engagement nubs 210 and 211 to allow engagement nub 210 to be inserted into one of vent holes 212 (see FIG. 2), and likewise engagement nub 211 gets inserted into a vent hole on the opposite side of housing 100. Cross member 2404 serves to prevent engagement nubs 210 & 211 from accidentally slipping out of the holes they have been engaged in.

Stand 209 is assembled by first mating surface 2416 of rotating crossbar 2405 with surface 2415 of base member 2403, such that rotation axis nub 2417 is inserted into hole 2418. The height of rotation axis nub 2417 is slightly less than the thickness of rotating cross bar 2405, such that when screw 2408 is threaded into the hole in the center of rotation axis nub 2417, screw 2408 forms threads within rotation axis nub 2417, and screw 2408 is then tightened so that washer 2409 presses rotating cross bar 2405 against base member 2403 to provide friction such that rotating cross bar 2405 can be rotated to the desired position and remain in that position (such as for use or storage). Stabilization nubs 2413 protrude from planar surface 2416 a distance equal to the thickness of base member 2415, so that once rotating cross bar 2416 is assembled with base 2415, the ends of stabilization nubs 2413 are co-planar with the bottom of base 2415. In folded configuration 2414, stabilization nubs 2413 rest against the sides of base member 2403.

The next step in assembly comprises inserting the lower ends of vertical members 2401 & 2402 into sockets 2410 and 2411, located at opposite ends of base member 2403. In some embodiments latch detents 2420 may engage detents within sockets 2410 and 2411. In other embodiments assembly may include gluing the lower ends of vertical members 2401 and 2402 into sockets 2410 & 2411.

Once vertical members 2401 & 2402 have been assembled with base member 2403, the top ends of vertical members 2401 and 2402 are slid into slots 2421 in cross bar 2404, and engagement nubs 210 and 211 and screw engagement nubs 2419 slide through clearance slots 2422, and cross bar 2404 comes to rest on stops 2412. Finally, screws 2406 & 2407 are threaded into the holes centered in thread-forming nubs 2419, from the sides of vertical members 2401 & 2402 opposite nubs 2419. Screws 2406 and 2407 do not clamp anything, but once screws 2406 & 2407 are in place, their heads prevent cross bar 2404 from sliding back in the direction from which it was slid onto vertical members 2401 & 2402.

A foldable stand as shown in FIGS. 22-24 can be described in claim language as: A foldable stand for a red light therapy unit comprising a right vertical member and a left vertical member, each with a top end and a bottom end, joined by a lower horizontal member and an upper horizontal member, where said lower horizontal member has a top and a bottom surface, and joins the bottom ends of said support members, and further comprising a rotatable cross-bar with two ends, said cross-bar pivotably attached to said lower horizontal member, such that said rotatable cross-bar may be pivoted perpendicular to said lower horizontal member, wherein said rotatable cross-bar comprises contact surface areas at each end, wherein said contact surface areas are co-planar with the bottom surface of said lower horizontal member; (dependent) wherein said vertical members each further comprise an engagement nub at the top end, wherein the engagement nubs of said vertical members are oriented toward one another; (dependent on first) wherein said upper horizontal member has a left end and a right end, and each of said left and right ends comprise slots which the upper ends of said vertical members slide through to attach said vertical members to said upper horizontal member, and each vertical member further comprises a feature which stops the sliding travel of said upper horizontal member down said vertical members at a predetermined distance between the top and bottom of each said vertical member; (dependent on third) wherein each said vertical member further comprises a screw-accepting boss, wherein said screw-accepting bosses slide through said slots in said upper horizontal member, and wherein after said bosses slide through said slots, non-clamping screws may be threaded into said bosses, such said screws are threaded into said bosses, said upper horizontal member can no longer slide off said vertical members.

Figure 25:
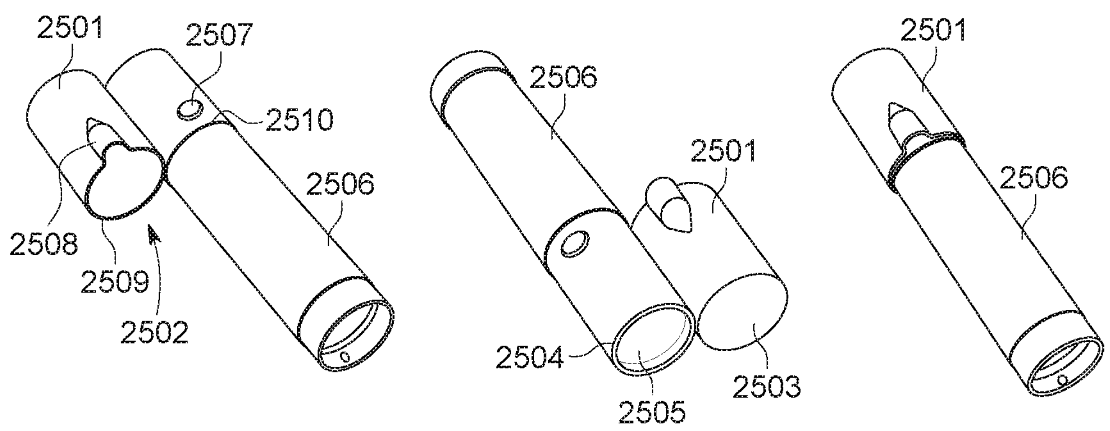
FIG. 25 depicts a protective cap for a hand-held red light therapy unit, according to a preferred embodiment of the present invention.

FIG. 25 depicts a protective cap for a hand-held red light therapy unit, according to a preferred embodiment of the present invention. Protective cap 2501 has an open end 2502 and a closed end 2503. In use, cap 2501 is slid onto hand-held red light therapy unit 2506 by sliding open end 2502 over optics end 2504 of red light therapy unit 2506. such that closed end 2503 covers and protects lens 2505 of red light therapy unit 2506. Protrusion 2508 (also herein referred to as an offset hollow section) slides over switch button/actuator 2507 and prevents switch button 2507 from being depressed while cap 2501 is in place. Protrusion 2507 is shaped such that cap 2501 can be slid onto red light therapy unit 2506 aligned such that protrusion 2506 slides into place covering button 2507, without touching button 2507, and once cap 2501 is installed, attempting to twist cap 2501 around the axis of red light therapy unit 2506 will cause an inner surface of protrusion 2508 to put force on button 2507 perpendicular to the operational axis of button 2507, and will thus not actuate button 2507.

In a preferred embodiment, cap 2501, once installed, is held in place by friction between the interior cylindrical section surface of cap 2501 and the exterior cylindrical section surface of red light therapy unit 2506. In a 3-D printed preferred embodiment, such friction is provided by surface irregularities of cap 2501 inherent in the 3-D printing process. In an alternate embodiment, rather than being circular, the cross-section of cap 2501 represented by surface 2503 is slightly elliptical, such that the minor axis of the slightly elliptical cross section of cap 2501 is slightly smaller than the diameter of red light therapy unit 2506, and the major axis is slightly bigger than the diameter of red light therapy unit 2506. In an alternate preferred embodiment, a mechanical detent on the inside of edge 2509 mates with groove feature 2510 of red light therapy unit 2506, securing cap 2501 to red light therapy unit 2506.

Figure 26:
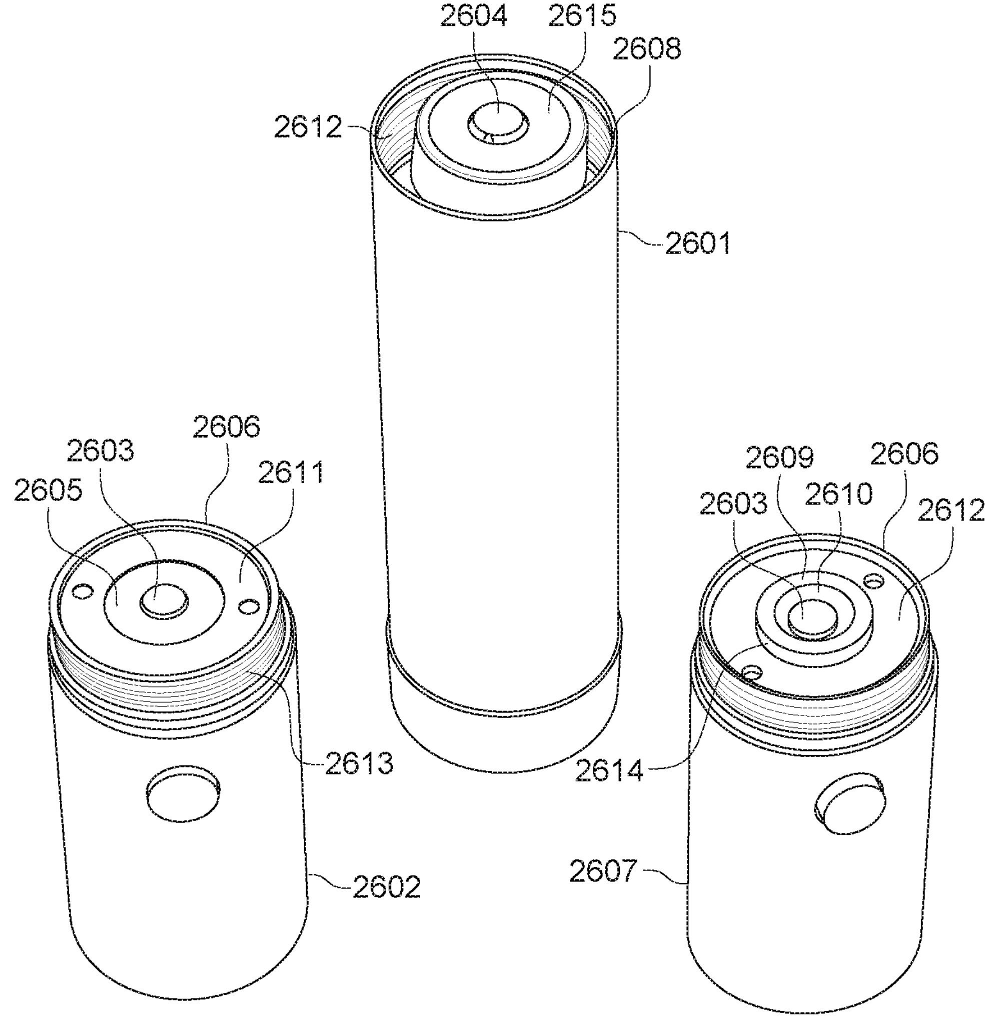
FIG. 26 depicts improvements to a hand-held red light therapy unit according to an aspect of the present invention.

FIG. 26 depicts improvements to a hand-held red light therapy unit according to an aspect of a preferred embodiment of the present invention. A hand-held red light therapy unit known in the art is shown in FIG. 26, and is made up of battery-containing housing 2601, and light engine 2602, which couples to housing 2601 via complementary internal threads 2612 and external threads 2613. Such hand-held red light therapy units are most often used by senior citizens to relieve joint pain. Many seniors find assembling such units challenging, because during assembly, battery positive button-tip 2604 may slide off positive contact 2603 and get caught between threaded ring 2611 and positive contact 2603, pressed against insulating ring 2605, preventing proper alignment of housing 2601 and light engine 2602. Further compounding this problem, as a dexterity-challenged senior citizen attempts proper alignment of light engine 2602 and battery housing 2601, electrically conductive edge 2606 may inadvertently electrically connect battery positive electrode 2604 and housing 2608, which is electrically connected to the battery negative electrode. Thus such accidental electrical connection of battery electrode 2604 and edge 2608 will momentarily short the battery. Lithium ion batteries, when shorted, can produce extreme heat which may destroy the battery and possibly cause burns or other injuries.

A preferred embodiment of the present invention provides an improved light engine 2607 for a hand-held red light therapy unit, including an improved insulator ring 2614 that provides two additional functions over prior art insulator ring 2605. Improved insulator ring 2614 includes protruding surface 2609, which protrudes further from surface 2612 than edge 2606, thus reducing the chance that electrically conductive edge 2608 could short battery 2615 during assembly of housing 2601 with light engine 2602. Furthermore funneling surface 2610 prevents battery positive electrode 2604 from slipping off contact 2603 during assembly of housing 2601 with light engine 2602, facilitating both easier and safer assembly by senior citizens who may be dexterity-challenged.

The improved insulating ring aspect of the present invention shown in FIG. 26 may be described in claim language as: An axially symmetric electrically insulating ring within a battery-powered hand-held red light therapy unit wherein said light therapy unit is made up of a cylindrical head housing section with an axis, that thread-mates with a cylindrical battery-containing housing section with the same axis, wherein said head section contains electronics clamped in place by an annular threaded ring with an inside diameter, said insulating ring comprising: a hollow cylindrical section with an outside diameter slightly less than the inside diameter of said threaded ring; said cylindrical insulating section having a length, and a protruding end wherein after assembly, said length is sufficient that said protruding end extends beyond said head housing in a direction along said axis; said insulating ring configured to be clamped in place by said threaded ring; said insulating section having an inside diameter configured to contain an electrical contact; said cylindrical insulating section having funneling indentation in said protruding end, said funneling indentation acting to funnel a protruding battery electrode into contact with said electrical contact upon assembly of said cylindrical head housing with said battery-containing housing section.

Figure 27:
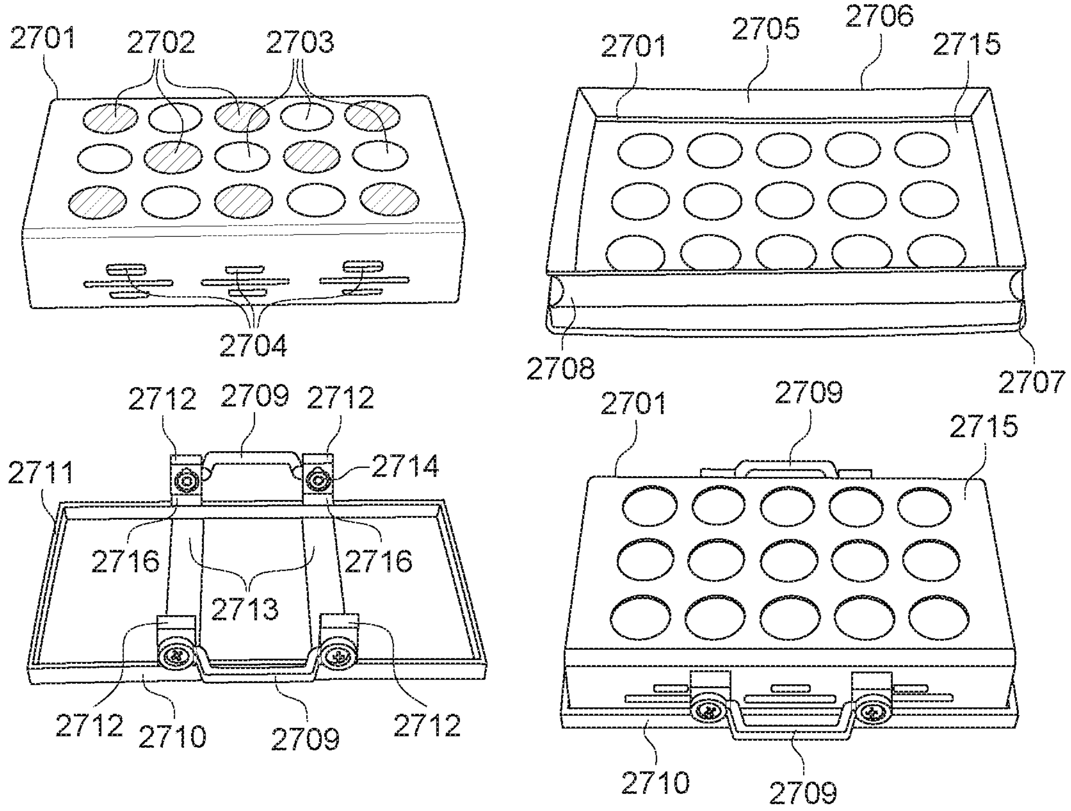
FIG. 27 depicts improvements to a small battery-powered red light therapy panel, according to preferred embodiments of the present invention.

FIG. 27 depicts improvements to a small battery-powered red light therapy panel, according to preferred embodiments of the present invention. A 15-LED red light therapy panel 2701 known in the art is shown in FIG. 27. The panel contains a rechargeable battery, timer, 8 660 nmLEDs which shine through lenses 2702, and 7 850 nm near infrared LEDs that shine through lenses 2703. Vent slots 2704 aid in cooling. Such a panel has numerous drawbacks. First, because the distance between the LED lenses is not short compared to the treatment penetration depth, if the panel is used in contact with skin, treatment is uneven. Second, if treatment is done some distance from the panel where illumination is more even, there is a significant loss in treatment strength due to scattered light. Third, it is cumbersome for a user to hold a panel unit at a fixed distance from a part of the body to be treated. Fourth, if a user does hold a panel unit such as panel 2701 a fixed distance from a treatment site for a typical treatment time of 5 to 10 minutes, it may be uncomfortable to look at the bright scattered light while maintaining the position.

In one aspect, the present invention provides a slip-on light guiding bellows 2708, which attaches by friction to the perimeter of red light therapy panel 2701. Cushioning lip 2706 is preferably placed in contact with the body, circumferentially around the area to undergo red light therapy treatment, and holds red light panel 2701 a known distance from the body, sufficient to allow uniform illumination by 660 nm wavelength LEDs 2702 and 850 nm wavelength LEDs 2703, while interior 2705 of bellows 2708 serves to reflect scattered light back to the treatment area. In a preferred embodiment to be used where LED panel 2701 is black, a white or red colored overlay is provided for the surface 2715, with holes cut through the overlay so that LEDs 2702 and 2703 shine through the overlay, and the overlay serves to reflect light back-scattered from the treatment area back to the treatment area to increase the percentage of red light absorbed by body tissue. In a preferred embodiment, lip 2707 serves the dual purpose of stiffening bellows 2708 radially where it hugs red light panel 2701, and providing a finger-graspable feature to aid ins sliding bellows 2708 into place on red light panel 2701.

In another aspect, the present invention provides a snap-on attachable frame 2710 which includes integral perimeter members 2711, integral strap tension counterbalancing members 2713, strap attachment anchors 2709, integral strap anchor attachment members 2712, integral strap anchor nut recesses 2714, and integral latching detents 2716. In a preferred embodiment, skirt members 2711 of strap adapter 2710 hug the perimeter of LED panel 2701, and latching detents 2716 engage vent slots 2704 to latch adapter 2710 to LED panel 2701, and tension members 2711 prevent strap anchors 2709 and strap anchor attaching members 2712 from twisting due to the torque applied to them by an attachment strap being fastened to strap anchors 2709 and used to secure surface 2715 or lip 2706 to the body part undergoing red light therapy treatment.

Possible claim language describing aspects of the present invention shown in FIG. 27, including two dependent claims listed as the last two elements, might be: An adapter for adapting a battery-powered red light therapy panel with vent holes, a perimeter, a back, and a optical output surface, such that said red light therapy panel can be conveniently strapped to a human body for strap-on red light therapy use, said adapter comprising: an integral plastic adapter frame which functionally snaps onto said red light therapy panel, said frame comprising integral perimeter members which function to hug the perimeter of said red light therapy panel, integral tension members which traverse the back of said red light therapy panel, two strap anchors which align with said tension members, a plurality of snap detents which engage said vent holes and function to snap said frame in place on said red light therapy panel; wherein said strap anchors are plastic and are an integral part of said frame; wherein said strap anchors are fastened to said frame with screws.

Figure 28:
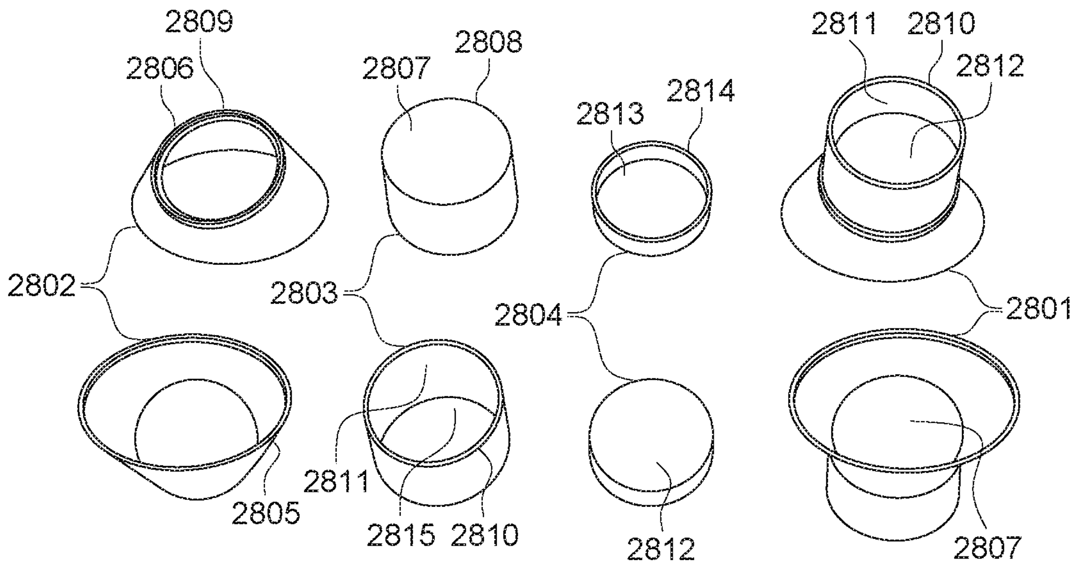
FIG. 28 depicts an aspect of the present invention for adapting hand held joint treatment red light therapy flashlights known in the art so that they may be used to safely provide vision-enhancement red light therapy treatments.
Figure 28:
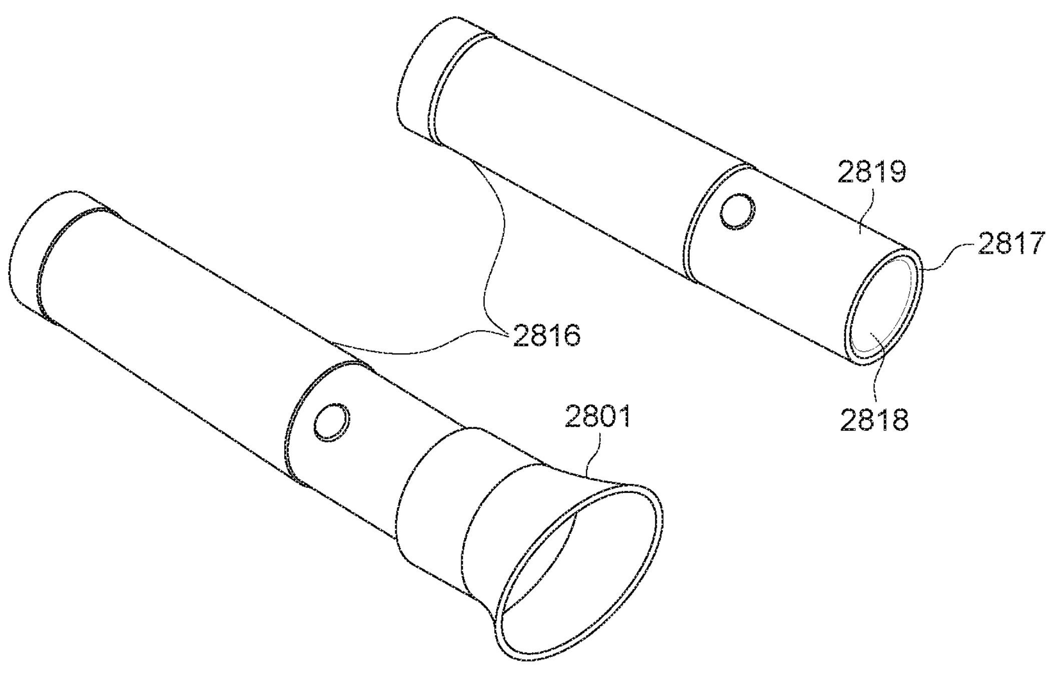

FIG. 28 depicts an aspect of the present invention for adapting hand-held joint treatment red light therapy flashlights known in the art, such as hand-held red light therapy flashlight 2816, so that they may be used to safely provide vision enhancement red light therapy treatments. In a preferred embodiment, eye treatment adapter 2801 is made up of three components bonded together: first diffuser 2804, second diffuser 2803, and positioning cone 2802. During assembly, outer circumference 2808 of surface 2807 fits within circular edge 2806 and is bonded to inner lip 2809 of positioning cone 2802. Likewise, circular edge 2814 fits within inner cylindrical surface 2811 and is bonded to the outer edge of circular surface 2815.

In use, optical output end 2817 of red light therapy flashlight 2816 is inserted into circular opening 2810 so that outer cylindrical surface 2819 of red light therapy flashlight 2816 fits within and is preferably hugged by cylindrical surface 2811, and optical output end 2817 rests against surface 2812. Positioning edge 2805 is then rested against tissue surrounding the eye which is to undergo red light therapy. In a preferred embodiment, surface 2811 mates in a friction fit with surface 2819, by one of the methods described above for the friction fit of cap 2501.

Light shining out of optical output 2818 of red light therapy flashlights known in the art may be significantly non-uniform in intensity, perhaps being as much as 100 times brighter exiting some parts of lens 2818 compared with other parts of lens 2818. The thickness between surfaces 2812 and 2813 of first diffuser 2804 and the thickness between surfaces 2815 and 2807 of second diffuser 2803, along with the after-assembly distance between first diffuser surface 3813 and second diffuser surface 2815 together determine the extent to which adapter 2801 serves to even out the uneven light intensity distribution exiting the lens 2811, which is inserted into opening 2810, and also together serve to determine the overall attenuation in total optical power between the optical power exiting lens 2818 and the optical power entering the eye under treatment. In a preferred embodiment, the thickness between surfaces 2812 and 2813 is 0.025 inches, as is the thickness between surfaces 2807 and 2815, and the assembled distance between surfaces 2813 and 2815 is 0.23 inches.

Figure 29:
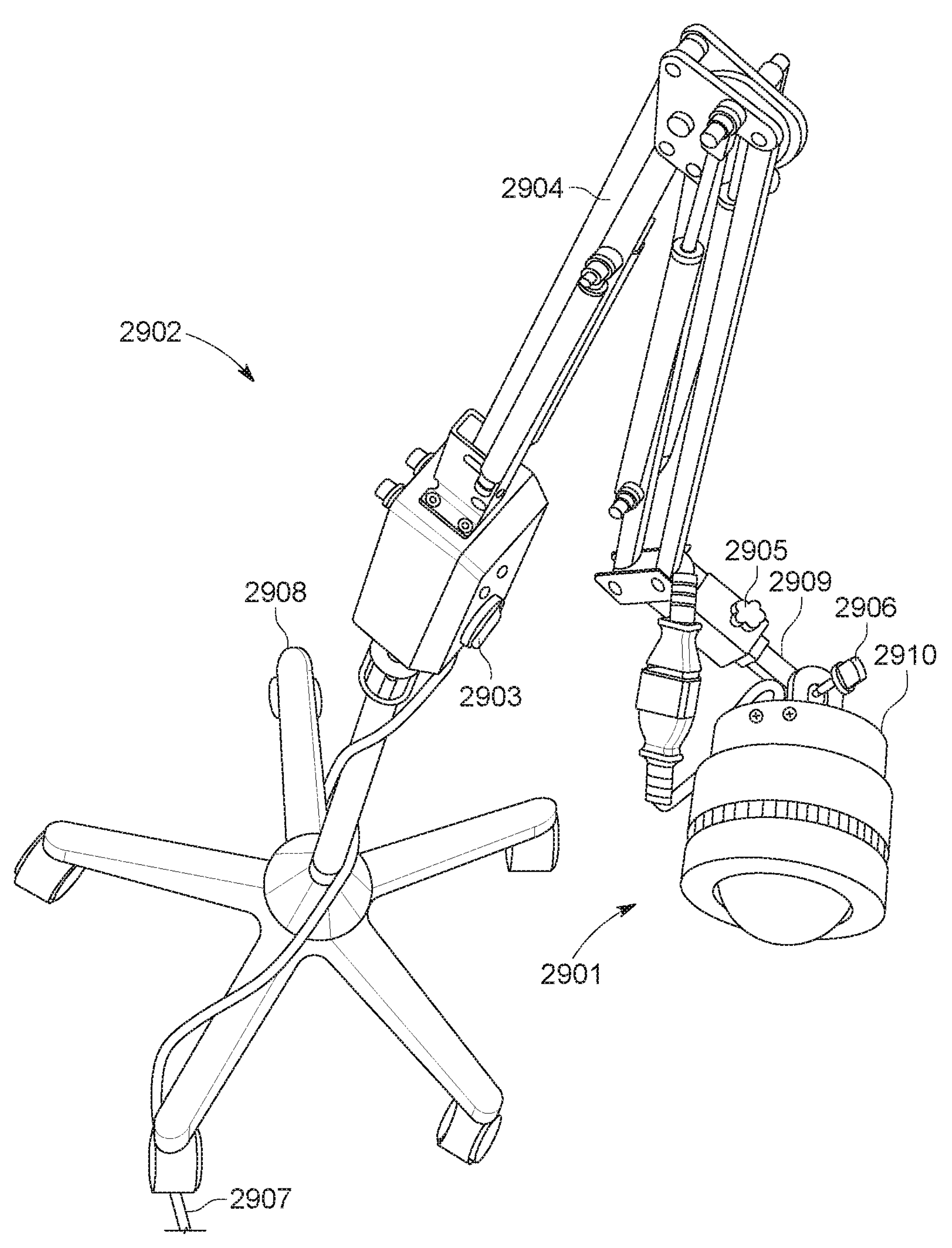
FIG. 29 depicts a red light therapy unit configured for medical office treatment use according to a preferred embodiment of the present invention.

FIG. 29 depicts a red light therapy unit configured for medical office treatment use according to a preferred embodiment of the present invention. Red light therapy head 2901 is mounted on a rolling treatment stand 2902 as is known in the art. Stand 2902 includes rolling base 2908, utility power cord 2907, electromechanical treatment timer 2903, articulated arm 2904, mutually perpendicular rotational axis clamps 2905 and 2906, and lamp attachment member 2909. In a preferred embodiment, adapter 2910 serves to mechanically affix red light therapy head 2901 to attachment member 2909, at an angle which may be adjusted during use around the axis of hand-tightenable fastener 2906. Adapter 2910 further serves to significantly improve the thermal cooling efficiency of red light therapy head 2901 by transforming air flow within red light therapy head 2901 from inefficient non-ducted flow, to efficient ducted flow.

Figure 30:
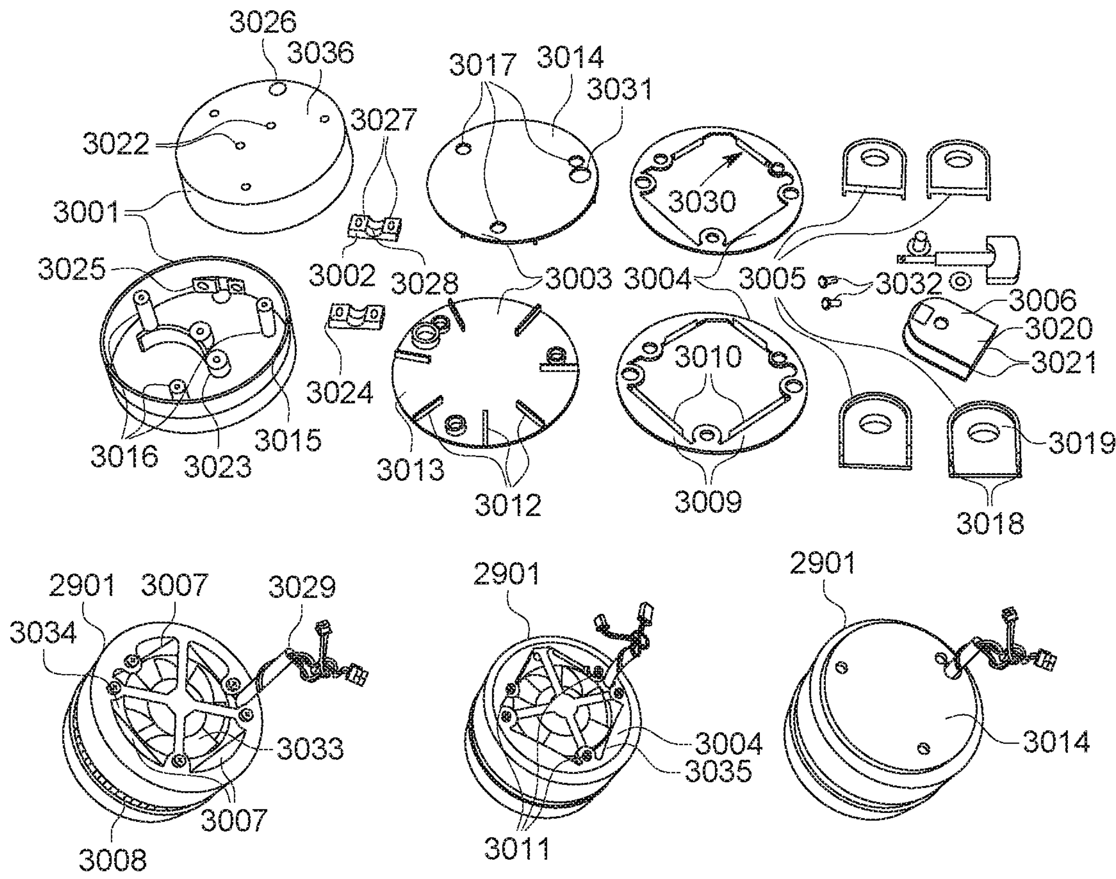
FIG. 30 depicts an exploded view of red light therapy head adapter 2910, and depicts key aspects of assembly.

In a preferred embodiment, adapter 2910, shown in red in FIG. 29 for clarity, is composed of six plastic parts, one sheet metal part, and assembly fasteners. FIG. 30 depicts an exploded view of red light therapy head adapter 2910, and depicts key aspects of assembly. Each plastic part is shown one way in silver, and flipped over in gold. Prior to attachment of adapter 2910 red light therapy head 2901 contains a fan which produces chaotic air circulation, because much of the air drawn into fan intake 3033 recirculates back around the fan through open air gaps 3007, rather than passing out through heatsink exit ports 3008.

In a preferred embodiment, adapter 2910 attaches to led light therapy head 2901 in a layered fashion. The first layer is duct-forming part 3004. Duct-forming part 3004 includes disc-section areas 3009 and lips 3010 which together serve to prevent air from recirculating through gaps 3007. Threaded bosses 3011 protrude through holes in recirculation blocking duct part 3004 and hold the part in alignment. Lips 3010 contact fan frame surface 3034. Duct-forming finned disc 3003 is installed as the next layer, such that fins 3012 contact surface 3035. Bosses 3011 go part way through holes 3017, and act to align finned disc 3003.

A utility power cable (visible in FIG. 29 but not shown in FIG. 30) enters hollow plastic housing 3001 through hole 3026, and is clamped in place by clamp member 3002, which incorporates detent rib 3028, which prevents the utility cable from moving once clamp member 3002 is fastened in place with screws that pass through holes 3027 such that surface 3025 mates with surface 3024. Once the utility power cable and power supply are assembled into housing 3001, housing 3001 is layered onto finned disc 3003 such that rim 3015 mates with the outer perimeter of surface 3014, and features at the ends of integral standoffs 3016 mate with holes 3017, aligning housing 3001 with the rest of the assembly. Power cables 3029 of red light therapy head 2901 pass through notch 3030 and hole 3031. The 3-layer assembly of housing 3001, recirculation-blocking baffle 3004, and duct-forming finned disc 3003 are clamped together and affixed to red light therapy head 2901 by screws that pass through integral standoffs 3016 and thread into bosses 3011.

U-shaped sheet metal member 3006 attaches to surface 3036 by screws 3032, which pass through holes 3021 into holes 3022, and form threads in integral bosses 3023, which are part of housing 3001. Decorative plastic parts 3005 attach to U-shaped sheet metal member 3006 via hook features 3018, and adhesive attachment of surfaces 3019 to surfaces 3020. After assembly, surface 3013, fins 3012, and surface 3035 form an intake duct that defines the path air takes from the environment to fan intake 3033.

Claim language describing adapter 2910 might be: An adapter for adapting a red light therapy head to a wheeled stand, wherein said wheeled stand includes an articulated arm with an attachment member, and said red light therapy head has an optical output end and an air intake end and an internal fan for drawing air in said air intake end, at least two threaded bosses affixed to said air intake end, and recirculation gaps surrounding said fan, said adapter comprising: a first plastic layer configured to contact said air intake end and block said air recirculation gaps, said first plastic layer comprising an opening through with air may flow to said air intake end, said first plastic layer further comprising holes through which said at least two threaded bosses pass, said holes serving to align said first plastic layer through mechanical communication with said threaded bosses; a second plastic layer comprising a circular disc of a first diameter with a first disc surface and a second disc surface, said first disc surface comprising radial fins and a first set of at least two hollow standoffs, wherein said standoffs have equal height to said fins, said fins and said standoffs configured to sandwich said first plastic layer between said second plastic layer and said air intake end, and said hollow standoffs are sized to allow said threaded bosses to penetrate part way through said forst set of hollow circular standoffs, wherein said fins and said first disc surface form an intake duct which guides environmental air to said fan; a third plastic layer comprising a hollow cylindrical section with an outer diameter and an inner diameter, said inner diameter equal to or smaller than said first diameter, wherein said cylindrical section has a closed end and an open end, said closed end comprising a circular inner surface and a circular outer surface, said third plastic layer further comprising a second set of least two hollow standoffs, affixed to said circular inner surface, and configured to align during assembly with said threaded bosses; said circular outer surface comprising a first set of holes in communication with the hollow interiors of said second set of hollow standoffs, such that screws passed through said holes, through said second set of standoffs, may thread into said threaded bosses, such that the tightening of said screws sandwiches said second plastic layer between said third plastic layer and said first plastic layer, and sandwiches said first plastic layer between said second plastic layer and said air intake end.

Alternate claim language describing adapter 2910 might be: An adapter for adapting a red light therapy head to a wheeled stand, wherein said wheeled stand includes an articulated arm with an attachment member, and said red light therapy head has an optical output end and an air intake end and an internal fan for drawing air in said air intake end, at least two threaded bosses affixed to said air intake end, and recirculation gaps surrounding said fan, said adapter comprising: a hollow plastic housing with a closed end and an open end, said closed end comprising a planar section with an inner surface and an outer surface, said housing further comprising a set of least two hollow standoffs, affixed to said inner surface, and configured to align during assembly with said threaded bosses; said outer surface comprising a first set of holes in communication with the hollow interiors of said of hollow standoffs, such that screws passed through said holes, through said standoffs, may thread into said threaded bosses, such that the tightening of said screws affixes said housing to said air intake end; said inner surface further comprising at least one integral plastic boss, said outer surface further comprising at least one hole passing through said outer surface and through said at least one boss, said hole being suitable for forming threads around a thread-forming screw; further comprising a U-shaped metal bracket with a bottom and two side flanges, with at least one hole through said bottom and at least one hole through each side flange, wherein said U-shaped bracket is fastened to said outside surface by at least one screw put through said at least one hole in said bottom and threaded into said at least one boss, fastening said U-bracket to said outside surface, where said holes through said side flanges function to fasten said U-bracket to said attachment member; said adapter further providing an air path for environmental air to flow through to reach said fan.

Figure 31:
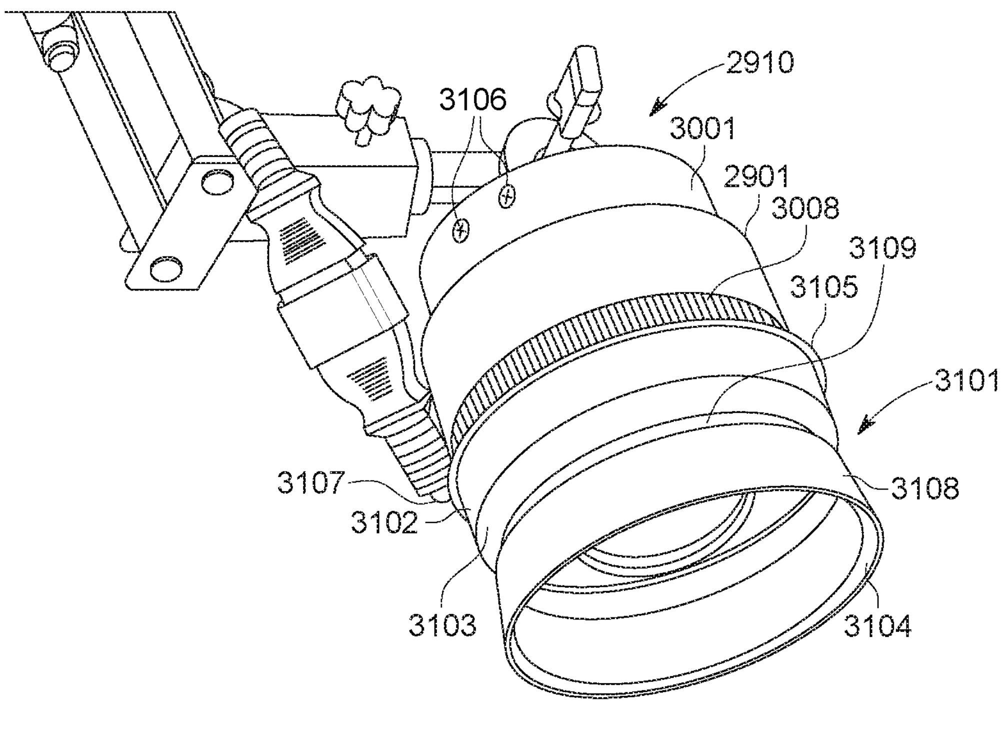
FIG. 31 depicts a red light therapy head configured for medical office treatment use according to a preferred embodiment of the present invention, including a flexible light guide for reducing scattered light and increasing the percentage of light absorbed by tissue being treated.

FIG. 31 depicts a red light therapy head configured for medical office treatment use according to a preferred embodiment of the present invention, including a flexible light guide 3101 for reducing scattered light and increasing the percentage of light absorbed by tissue being treated. Flexible light guide 3101 includes cylindrical section 3102 which hugs the outer cylindrical surface of red light therapy head 2901. Manually graspable lip 3105 facilitates a user pulling cylindrical section 3102 onto red light therapy head 2901. Inward-angled section 3103 acts in part to provide flexibility of light guide 3010, and serves in part as a detent to prevent light guide 3101 from sliding too far onto red light therapy head 2901 such that vent area 3008 will not be blocked. Outward-angles lip 3104 is provided for increased comfort where flexible light guide 3101 contacts the perimeter of the area of the human or animal body being treated.

Recessed screws 3106 pass through holes in housing 3001 to form threads in holes 3027 (see FIG. 30), and facilitate clamping of utility power cable 3107. In an alternate embodiment, cylindrical section 3108 may be eliminated, and outward-angled conical section 3109 may serve to contact the body and surround the area of skin being treated as lip 3104 is designed to do in the embodiment shown in FIG. 31.

In claim language, the flexible light guide embodiment shown in FIG. 31 may be described as: A flexible light guide for improving the treatment efficacy of a circular red light therapy head, said red light therapy head having a light output end and a cylindrical outer surface adjoining said light output end, said flexible light guide comprising: a first cylindrical flexible section with an inner surface configured to slide over and hug said cylindrical outer surface, said cylindrical section having first and second ends, said first end adjoined to a radially protruding circular lip; said second end adjoined to an inward angled conical flexible section serving to prevent said light guide from sliding onto said cylindrical outer surface beyond a predetermined distance; further comprising an outward angled flexible conical section adjoined to said inward angled conical section; further comprising an second outward angled flexible conical section configured to contact a portion of a human body to undergo red light therapy treatment, wherein said second outward angled flexible conical section is directly connected to said first outward angled flexible conical section, or indirectly connected thereto by one or more flexible conical or cylindrical sections; wherein said flexible light guide is made of a material providing specular and/or non-specular reflection of the majority of red light impinging on said material.

Figure 32:
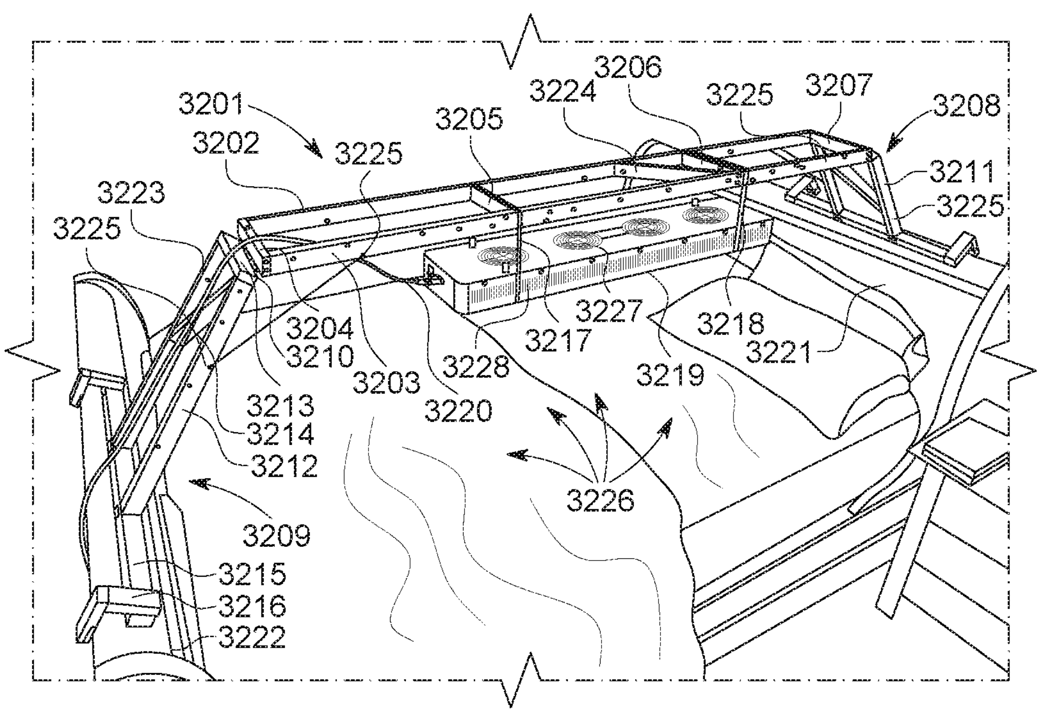
FIG. 32 depicts a red light therapy bed adapter according to a preferred embodiment of the present invention allowing a stand-up red light therapy panel to be used in bed.

FIG. 32 depicts a red light therapy bed adapter 3226 according to a preferred embodiment of the present invention, allowing a stand-up red light therapy panel to be used in bed. The embodiment shown is for use on a "sleigh-style" bed, which includes head hardware consisting of headboard 3221 and foot hardware consisting of footboard 3222. Folding bed adapter 3226 includes a central support frame 3201 made up of support rails 2302 and 3203, connected by transverse members 2304, 3205, 3206, 3207, and torsion brace 3224.

Figure 39:
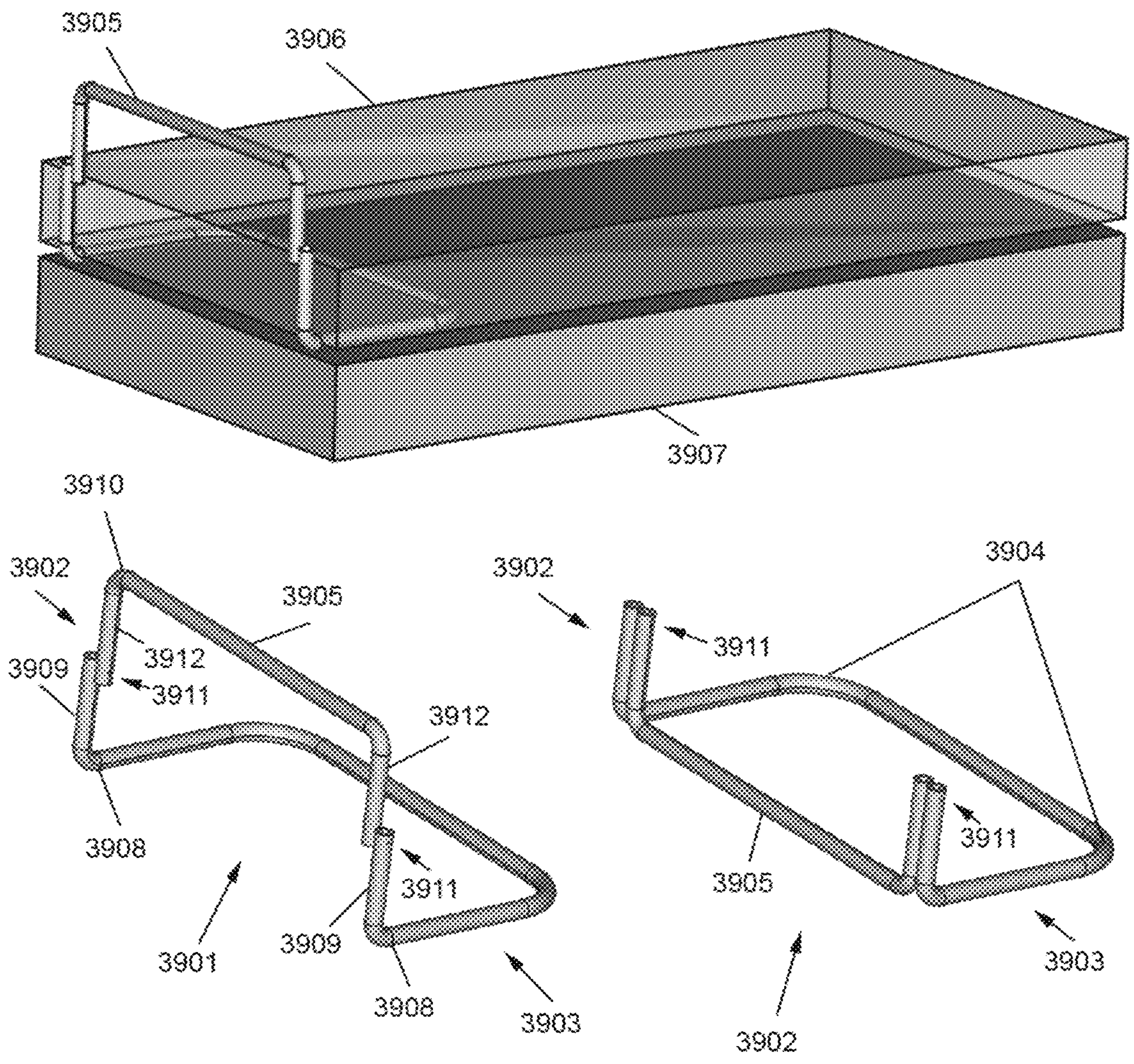
FIG. 39 depicts tubular bed head/foot hardware that transforms perpendicular to its use/storage plane, according to a preferred embodiment of the present invention.
Figure 40:
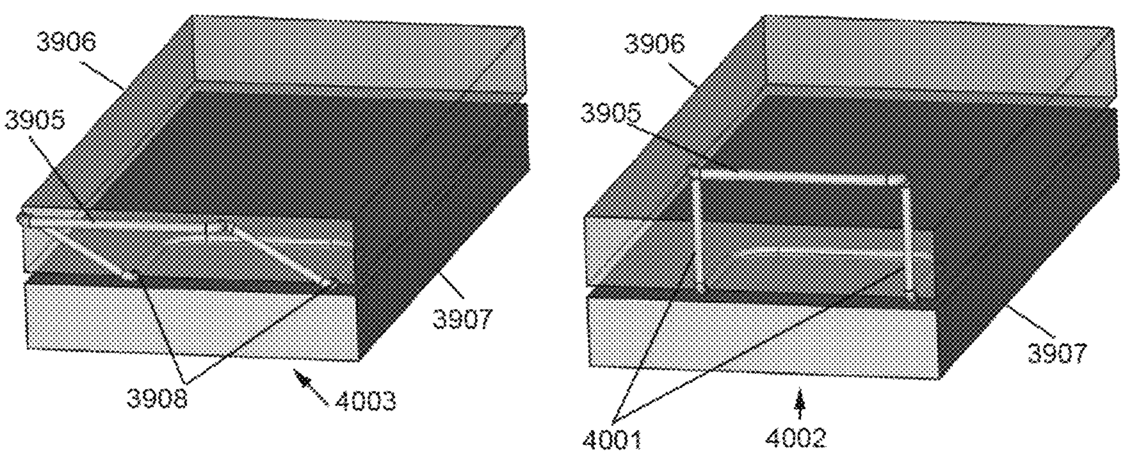
FIG. 40 depicts tubular bed head/foot hardware including a vertical section that transforms within its use/storage plane, according to a preferred embodiment of the present invention.
Figure 41:
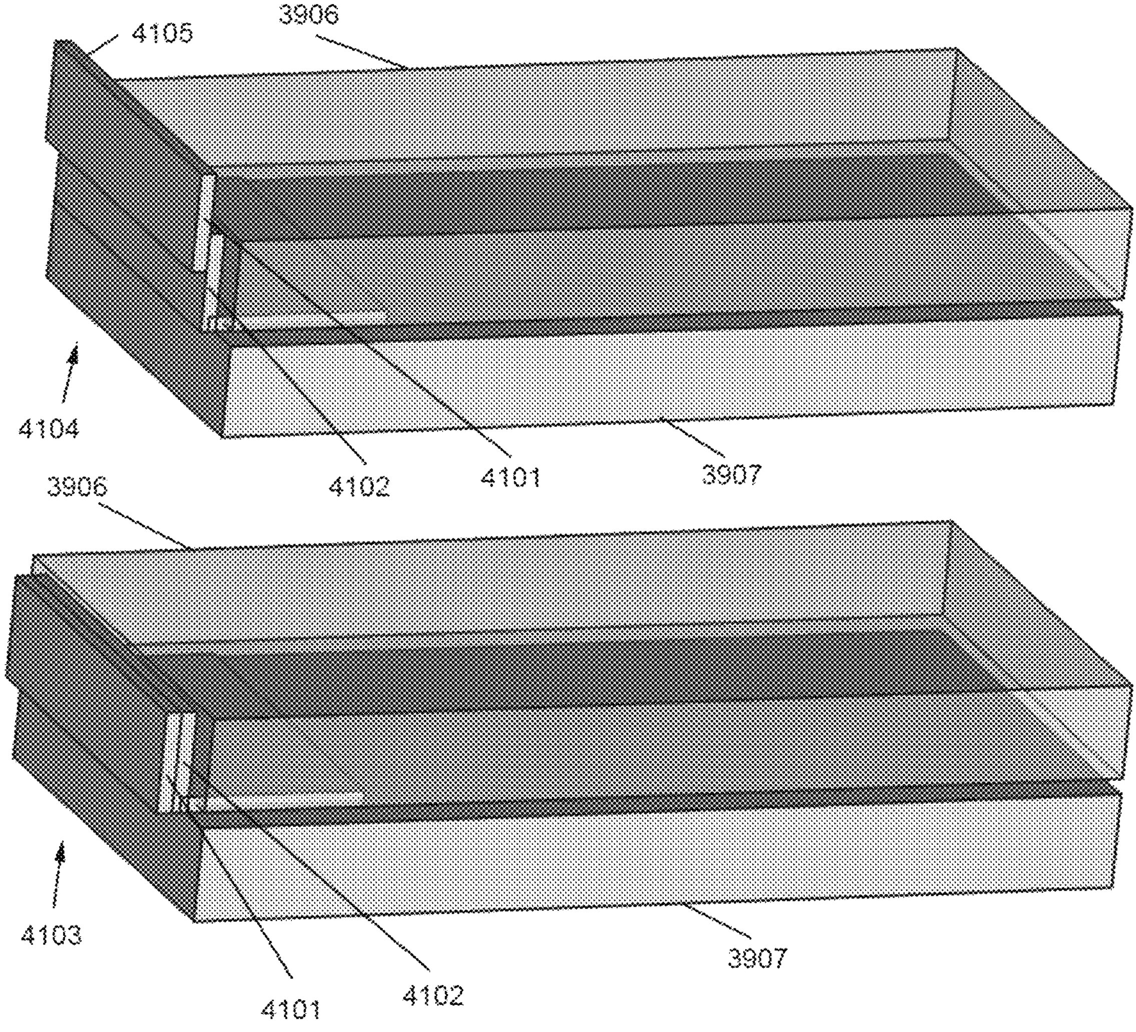
FIG. 41 depicts bed head/foot hardware made from multiple plank sections, that transforms within its use/storage plane, according to a preferred embodiment of the present invention.

Within this document, the term "head hardware" or "head-end hardware" will be construed to mean hardware stably affixed to the head of a bed. Examples of integrally attached head-end hardware include a headboard, or a metal or wooden bed frame that rises above the level of the mattress at the head of the bed. Likewise, examples of integrally attached foot-end hardware include a footboard, or a metal or wooden bed frame that rises above the level of the mattress at the foot of the bed. In embodiments of the present invention for use on beds not equipped with integral foot-end hardware and/or integral head-end hardware, the present invention provides for easily installable foot-end hardware and easily installable head-end hardware, as depicted in FIGS. 39-41.

Toward the head of the bed, central support frame (also herein referred to as central subassembly) 3201 in FIG. 32 attaches via hinge 3211 to folding head-end subassembly 3208. Toward the foot of the bed, central support frame 3201 attaches via hinge 3210 to folding subassembly 3209. Each folding sub-frame 3208 & 3209 is made up of two support rails 3212 & 3223, hinge-attaching transverse member 3213, torsion brace 3214, elongated stabilizing transverse member 3215, and two rotating L-brackets 3216. Red light therapy panel 2319 is powered by utility cord 3220 and is suspended from cord loops 3217 and 3218.

The portions of cords 3217 and 3218 which hang below central subsection 3201 in FIG. 32 and serve to support red light therapy lamp 3219 shall be referred to in this document as hanging cord sections. In alternate embodiments, such hanging cord sections attach separately at each end to subsection 3201, rather than being part of a cord loop that goes around subsection 3201. In an alternate embodiment, such cord sections are portions of loop cords which pass through holes in subsection 3201. Removably attaching/removing of red light therapy lamp 3219 to/from central subsection 3201, so that the assembly of central and end subsections 3201, 3209, and 3208 is light and easy to install/remove from bed head and foot hardware.

In an alternate embodiment, red light therapy lamp 3219 is installed between central subsection side rails 3202 and 3203. In such am embodiment, and may drop in by gravity, supported by stops, or may be permanently affixed between rails 3202 and 3203. In such an embodiment, flexible light guide 3801 should not cross the top of central subsection 3201, but rather should be implemented as separate light guides that mate with members 3202 and 3203 at the top end, and at the lower end come close to or rest on the bed over which assembly 3226 is mounted.

Transverse members 3205 & 3206 are positioned near the intended positions of cord loops 3217 and 3218 to counter-balance support rails 3202 and 3203 from being pushed toward one another by the forces the weight of red light therapy panel 3219 applies via cords 3217 and 3218. Transverse members 3204 and 3213 additionally act as support for utility power cable 3220, so that utility power cable 3220 does not hang down onto the bed and get in the way of the user. Travel limit cables anchored at points 3225 serve to prevent sub-frames 3208 and 3209 from unfolding too far to provide proper support, and L-brackets 3216 serve to limit travel of sub frames 3208 lnd 3209 once red light therapy bed adapter frame 3226 is positioned for use. In a preferred embodiment, extended transverse members 2215 and rotatable L-brackets 2216 have a polymer foam interface 3603 attached to prevent scratching the finish of headboard 3221 and footboard 3222.

Figures 33, 34:
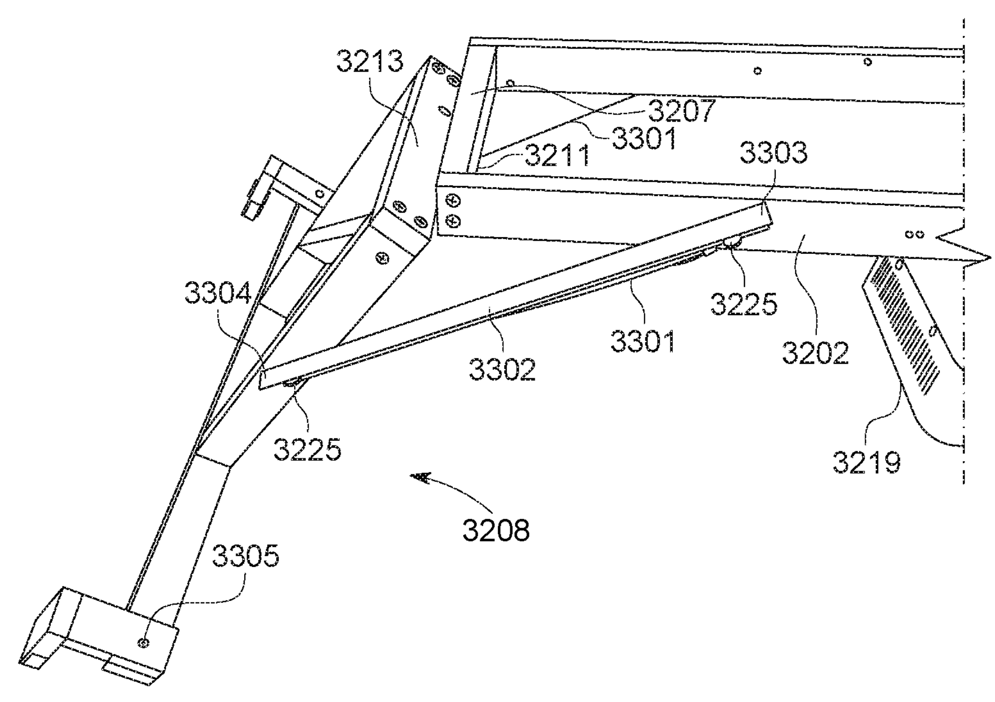
FIG. 33 depicts a preferred embodiment of a combination snap-in-place rigid member and a travel-limiting cable used to fix the angle between a folding subassembly and a central support subassembly in a preferred embodiment of the present invention shown in FIG. 32.
FIG. 34 depicts details of the joint between the folding subassembly at the foot of the bed and the central support subassembly of the red light therapy bed adapter shown in FIG. 32.

FIG. 33 depicts a preferred embodiment of a combination snap-in-place rigid member 3302 and travel-limiting cable 3301 used to fix the angle between folding subassembly 3208 and central support subassembly 3201 of a preferred embodiment of the present invention shown in FIG. 32. In the preferred embodiment shown, removable rigid brace 3302 snaps onto the same support anchors 3225 used to anchor the ends of travel limiting cable 3301. In an alternate embodiment, end 3303 of rigid support member 3302 may be pivotably attached to an anchor structure affixed to support member 3202, and end 3304 of rigid support member 3302 may be latchably attachable to an anchor structure on member 3202 during storage, and to an anchor structure affixed to foldable support structure 3208 during use. In such alternate embodiment, an additional anchor structure may be affixed to member 3202, to which end 3304 of rigid member 3302 may be affixed when folding structures 3208 and 3209 are folded against central support structure 3201 of red light therapy adapter 3226 for storage, as would be the case when red light therapy adapter 3226 is to be stored under a bed. In such alternate embodiment, the method of removable attachment of end 3304 to such additional anchor structure may be magnetic. In an alternate embodiment without cable 3301, rigid brace 3302 may be pivotably attached at end 3204, and lachably slidably attached at end 3303, such that when latched in the "use" position, sub-frame 3208 is held with respect to central span 3201 as shown in FIG. 33, and when latched in the "storage" position, sub-frame 3208 is held with respect to central sub-frame 3201 as shown in FIG. 35.

FIG. 34 depicts details of the joint between folding subassembly 3209 at the foot of the bed and central support subassembly 3201 of the red light therapy bed adapter shown in FIG. 32. In a preferred embodiment, hinge 3210 is a piano-style hinge, such that surface 3401 may fold flat against surface 3402 when red light therapy adapter 3226 is to be stored.

Figure 35:
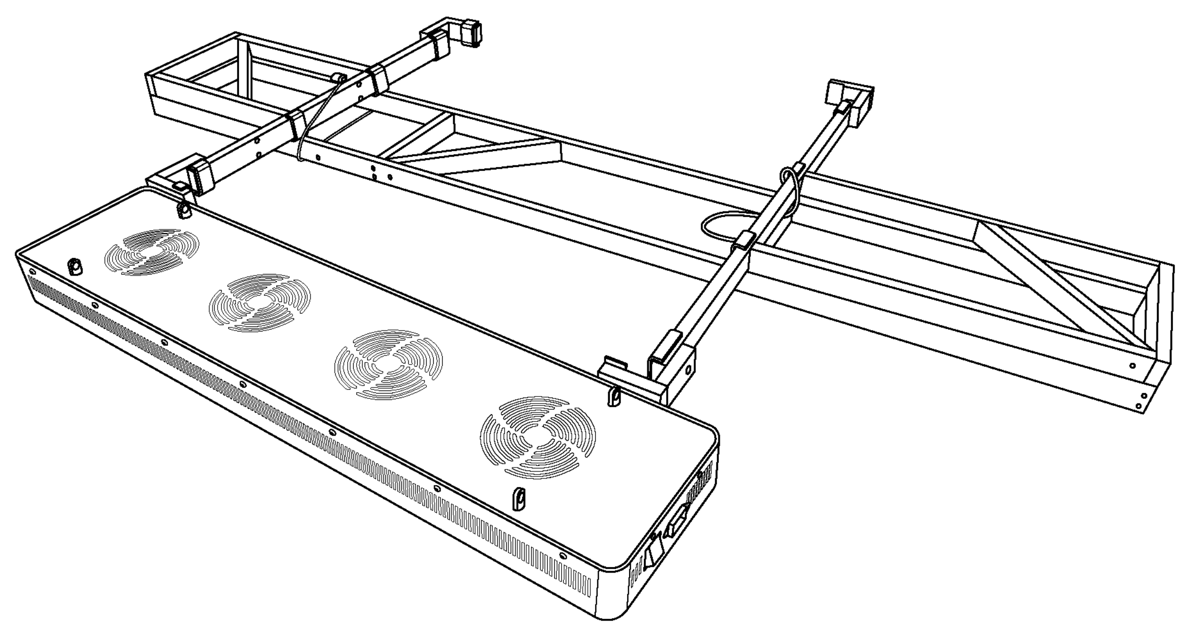
FIG. 35 depicts the red light therapy adapter of FIG. 32, folded flat for storage under a bed.

FIG. 35 depicts the red light therapy adapter of FIG. 32, folded flat for storage under a bed.

Figure 36:
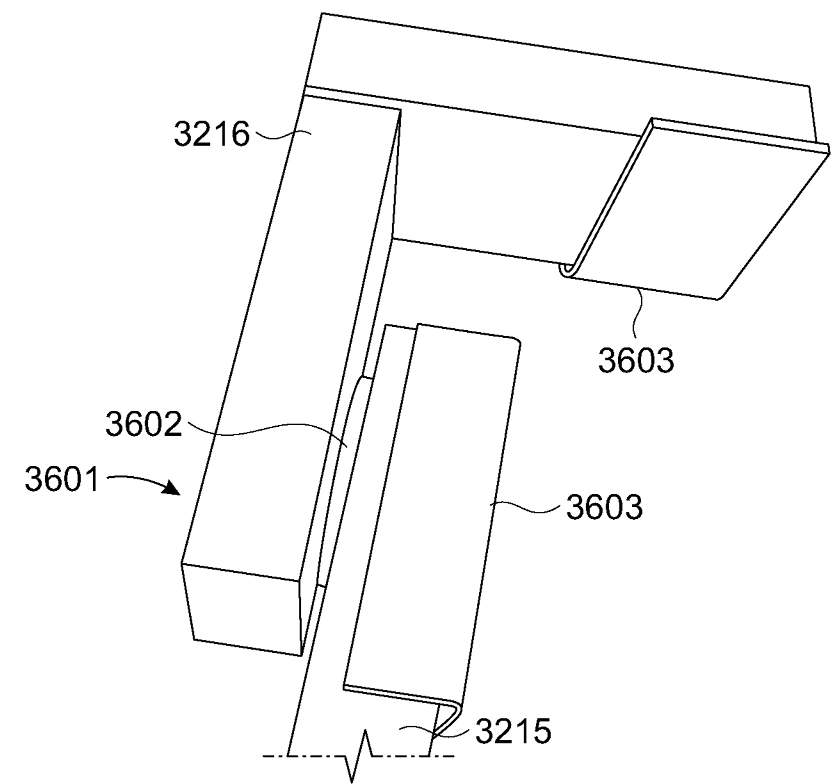
FIG. 36 depicts detail of a rotary L-bracket joint according to a preferred embodiment of the present invention.

FIG. 36 depicts detail of a rotary L-bracket joint according to a preferred embodiment of the present invention. Screw 3305 passes through the axis of rotary joint 3601, and provides assembly pressure to sandwich rotary detent wafer 3602 between L-bracket 3216 and elongated transverse member 3215. Polymer foam 3603 provides a soft surface for contacting bed headboard 3221 or footboard 3222.

Figure 37:
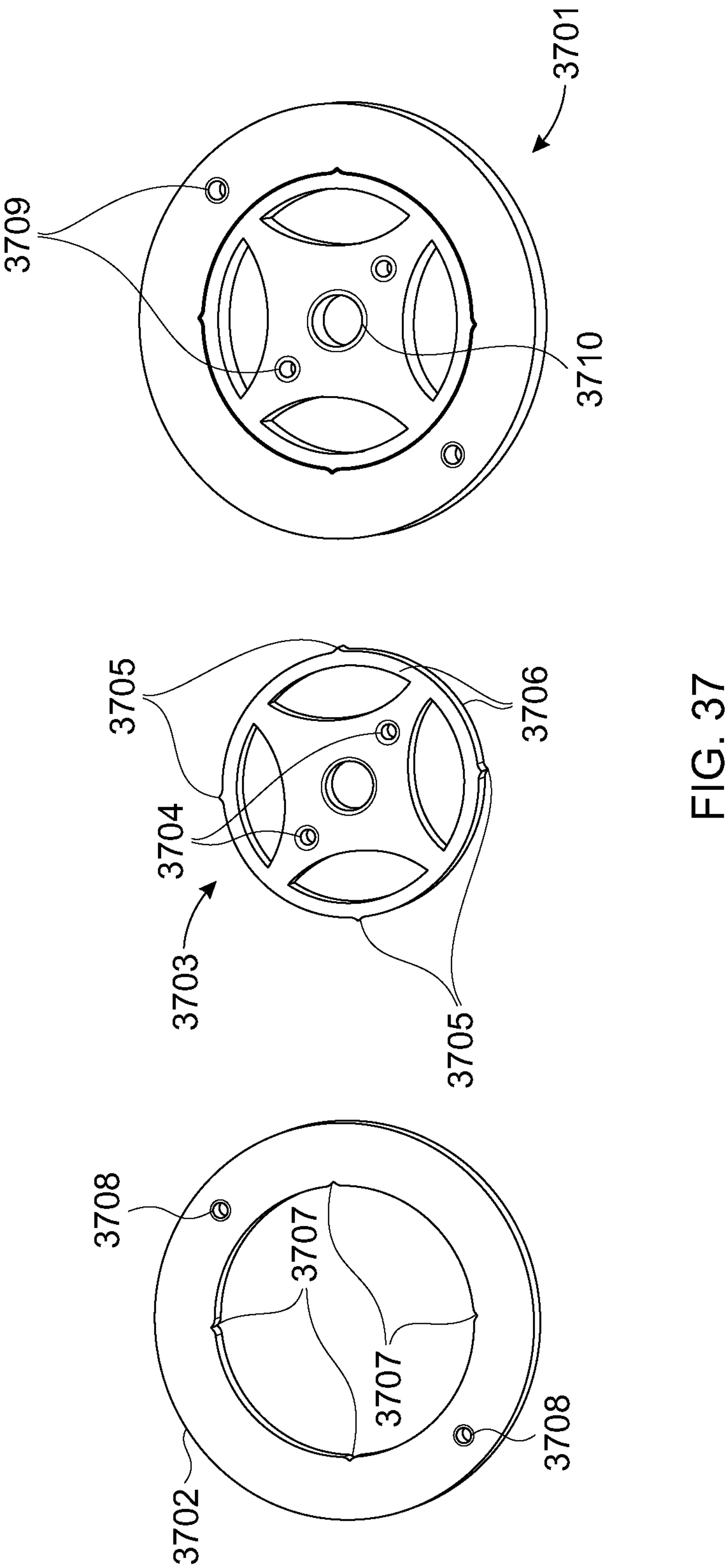
FIG. 37 depicts a rotary detent wafer according to a preferred embodiment of the present invention.

FIG. 37 depicts a rotary detent wafer 3701 according to a preferred embodiment of the present invention. Rotary detent wafer 3701 is made up of outer ring 3702 and central section 3703. Ring 3702 includes concave detents 3707, and attachment holes 3708, through which small nails may pass to attach ring 3702 to elongated member 3215 or rotatable L-bracket 3216. Central section 3703 includes convex detents 3705, and attachment holes 3704, through which small nails may pass to attach central section 3703 to elongated member 3215 or rotatable L-bracket 3216. Four integral circular arc members 3706 provide spring pressure to engage convex detents 3705 into concave detents 3707 when L-brackets 3216 are in either "use mode" (as shown in FIG. 32), or "storage mode", as shown in FIGS. 35 and 36. Circular recesses 3709 allow the heads of attachment nails to be recessed below the surface of rotary detent wafer 3701 for smooth operation. Central hole 3710 allows screw 3305 to pass through rotary detent wafer 3701 and act as an axis of rotation for rotary L-bracket 3216.

Figure 38:
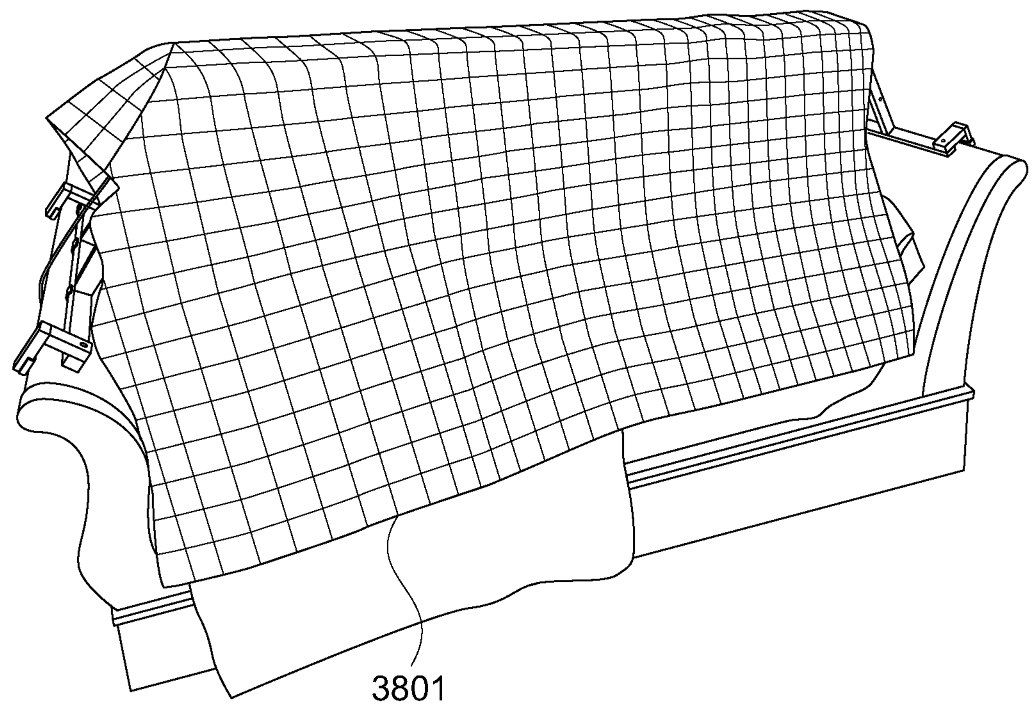
FIG. 38 depicts the red light therapy bed adapter of FIG. 32, with a flexible light guide added to increase efficacy and comfort of red light therapy, and allow reduced treatment time.
Figure 38:
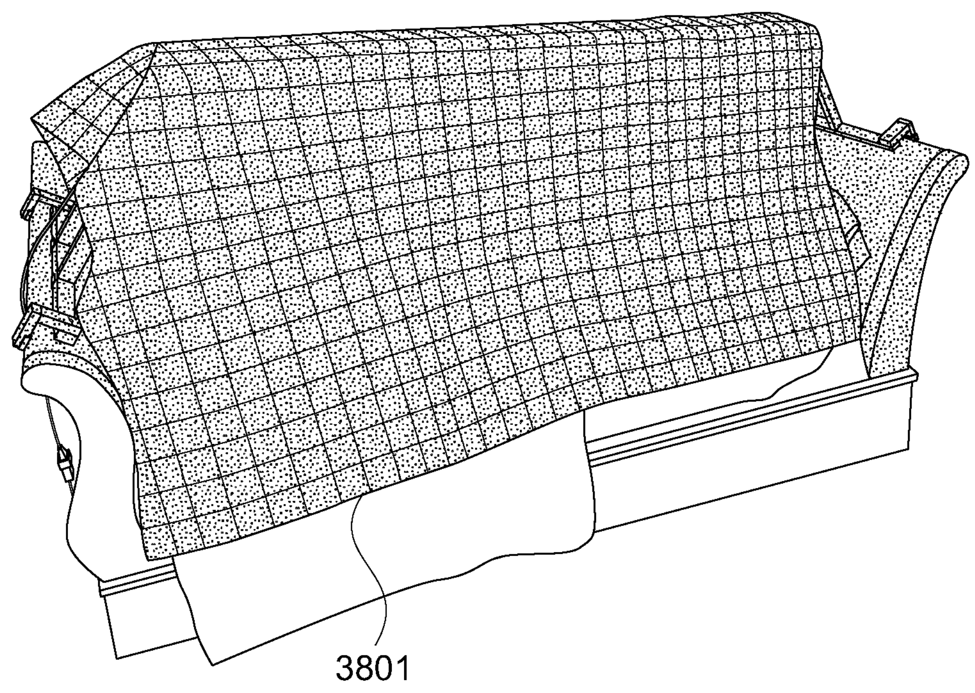

FIG. 38 depicts the red light therapy bed adapter of FIG. 32, with a flexible light guide 3801 added to increase efficacy and comfort of red light therapy, and allow reduced treatment time. The flexible light guide in FIG. 37 is aluminized mylar draped over red light support section 3201, such that the flexible light guide contacts the bed on each side of the area where a user would lie for red light therapy. As can be seen in the photo where the red light therapy panel is turned on, about 97% of scattered light is reflected back to the treatment area, while about 3% of the scattered light penetrates the flexible light guide, this significantly increases treatment strength, providing deeper penetration of red light into the body, and offering reduced treatment time. Furthermore, the flexible light guide reduces drafts, and the heated air coming from the fan vents of red light therapy panel 3219 warms the treatment area, making treatment far more enjoyable, providing extra motivation for users to regularly engage in and reap the benefits of full-body red light therapy.

Flexible light guide 3801 may be implemented as one or more aluminized Mylar or white fabric sheets draped over central support members 3202 and 3203, as shown in FIG. 38, or could be implemented spring-retractable roll-up sheets as shown in FIG. 49, which mount to members 3202 and 3203 and may be unrolled to produce a similar light guide geometry to that shown in FIG. 38. Either way, the guide is flexible and may easily be flexed to allow a person to get in or out of the treatment area.

In embodiments where light guide 3801 is a continuous light-reflective sheet that goes over the top of central subsection 3201, the vertical distance between fan intake vents 3227 and light guide 3801 must allow sufficient air flow through fan vents 3227 to allow proper cooling of internal circuitry of red light therapy panel 3219. Similarly, the distance between exhaust vents 3228 and flexible light guide 3801 must allow sufficient air flow through exhaust vents 3228 to allow proper cooling of internal circuitry of red light therapy panel 3219.

In embodiments where red light therapy lamp 3219 is mounted between rails 3202 and 3203, it is preferable to use spring-retractable roll-up sheet light guides such as the light guide shown in FIG. 49, where one such light guide mounts along the length of rail 3202, and one such light guide mounts along the length of rail 3203, on opposite sides of the treatment area. In such an embodiment, a pathway must be provided for air to flow out vents 3228 without being blocked by rails 3202 and 3203.

In a preferred embodiment, a spring-retracted roll-up flexible light guide such as shown in FIG. 49 is mounted on each side of central subsection 3201 of the red light therapy adapter shown in FIG. 49. For example, brackets 4901 mount to rail 3203, such that a user preparing for red light therapy may lie in bed and reach up and grasp curled over edge 4903 of flexible light guide 4904, which is stiffened along the edge by insert 4902. Pulling down on edge 4903, the user unrolls light guide 4904 from roller 4906, with light-reflecting surface 4905 functioning to reflect back into the treatment area the majority of red light scattered or projected out of the treatment area. As flexible light guide 4904 is slowly unrolled by the user pulling edge 4903 down, gravity/centrifugal ratchet 4907 (as commonly known in the art of spring retractable window shades) repeatedly re-engages in gravity mode, preventing flexible light guide 4904 from being rolled back onto roller 4906 by spring tension in the spring (not shown) inside roller 4906. When the user wishes to roll flexible light guide 4904 back onto roller 4906 subsequent to a red light therapy session, the user gives a quick downward tug on edge 4903, putting gravity/centrifugal ratchet 4907 into centrifugal mode so that the ratchet does not reengage until the angular velocity of roller 4906 is low enough for gravity/centrifugal ratchet 4907 to transition back to gravity mode.

An additional advantage of using flexible light guides as described above with the red light therapy adapter shown in FIG. 32 is that air in the treatment area is typically warmed by several degrees by the air recirculating through red light therapy unit 3219, because the air is partially contained by the flexible light guides. Indoor spaces are typically maintained at a temperature comfortable for clothed people, and full-body red light therapy is done in an un-clothed state, so the increased temperature of the air partly contained by the flexible light guides suspended by central subsection 3201 makes red light therapy sessions done within flexible light guides more comfortable and enjoyable, in addition to more efficacious.

FIG. 39 depicts tubular bed head/foot hardware 3901 that transforms perpendicular to its use/storage plane, according to a preferred embodiment of the present invention. U-shaped horizontal planar section 3903 is designed to fit between mattress 3906 and box spring 3907 as shown. Transformable U-shaped vertical section 3902 attaches to horizontal U-frame 3903 at joints 3908. Rounded corners 3904 of horizontal U-frame 3903 ate designed to facilitate sliding into place between mattress 3906 and box spring 3907 without catching on or tearing fabric surfaces of mattress 3906 or box spring 3907.

Vertical members 3912 and horizontal member 3905 form a transformable sub-assembly 3910 which may be rotated from storage mode 3903 to use mode 3901, by rotating the rotatable subassembly 3910 around latchable rotation joints 3911. In use-mode configuration 3901, horizontal member 3905 is raised above the top surface of mattress 3906, and configured to engage members 3215 and 3216 (see FIG. 32). In storage-mode configuration3902, horizontal member 3905 sits below the plane of the top surface of mattress 3906, such that it will not be in the way of someone wishing to sit at the foot of the bed.

FIG. 40 depicts tubular bed head/foot hardware including a vertical section that transforms within its use/storage plane, according to a preferred embodiment of the present invention. In such an embodiment, vertical members 4001 rotate about latchable rotatable joints 3908 to transform between use mode 4002 and storage mode 4003.

In an alternate embodiment, vertical members 4001 are made up of multiple coaxial latching or clampable telescoping sections, facilitating transforming horizontal member 3905 from above-mattress-top use mode to below-mattress-top storage mode. In such an embodiment, the telescoping range of members 4001 may be made sufficient to bring member 3905 up to the level of adapter center section 3201. In such an embodiment, transformable sections 3208 and 3209 may be implemented as telescoping from, and co-planar with, central support span 3201, rather than attached by hinges 3210 and 3211. Such an embodiment may be implemented with sections telescoping from both ends 3204 and 3207 of central support section 3201, or a telescoping section which telescopes from only one of ends 3204 or 3207, where the opposite end of central support frame 3201 is configured to attach directly to member 3905.

FIG. 41 depicts bed head/foot hardware made from multiple plank sections, where the vertical planer subassembly transforms within its use/storage plane, according to a preferred embodiment of the present invention. In such an embodiment, plank section 4101 is slidably attached to plank section 4102, and may be slid from a stored configuration 4103 to a use configuration 4104, in which configuration it may be latched or clamped, and in such configuration, top surface 4105 acts as an engagement surface to support members 3205 and 3216.

A red light therapy adapter as shown in FIG. 32 may be described in claim language as follows: A red light therapy adapter for adapting red light therapy panels used in the art for standing red light therapy, such that through said adapter, said red light therapy panels may comfortably and effectively provide red light therapy to a person lying on a bed, said bed having a foot and a head, said adapter comprising: a central support subassembly with a head end and a foot end, comprising two parallel support members and two transverse members, a foot-end subassembly attached to said the foot end of said central subassembly by a foot-end hinge, a head-end subassembly attached to said head end of said central support subassembly by a head-end hinge, said head-end hinge configured to allow said head-end subassembly to transition from a folded angle substantially parallel to said central support assembly, to a head-end unfolded angle, said foot-end hinge configured to allow said foot-end subassembly to transition from a folded angle substantially parallel to said central support subassembly, to a foot-end unfolded angle; further comprising a foot-end travel-limit mechanism acting to limit angular travel of said foot-end subassembly with respect to said central support subassembly to said foot-end unfolded angle; further comprising a head-end travel-limit mechanism acting to limit angular travel of said head-end subassembly with respect to said central support subassembly to said head-end unfolded angle; wherein said foot-end assembly has a hinge-end and a bed hardware interface end, said bed hardware interface end being configured to stably support said adapter on bed foot hardware located at the foot of said bed; wherein said head-end assembly has a hinge-end and a bed hardware interface end, said bed hardware interface end being configured to stably support said adapter on bed head hardware located at the head of said bed.

FIG. 50 depicts a tubular metal embodiment of a red light therapy adapter for adapting a red light therapy lamp to provide red light therapy in bed. Bed adapter 500 adapts red light therapy lamp 508 for use by a person lying on bed 505. Two mattress interface modules 501 are sandwiched between mattress 503 and box spring 504. Each mattress interface module 501 consists of a planar arrangement of two head/foot motion stabilizing members 516 configured to be sandwiched between mattress 503 and box spring 504, one side-to-side stabilizing member 517, and one vertical socket member 514. In a preferred embodiment, vertical socket member 514 is welded to side-to-side stabilizing member 517 at joint 515. In some embodiments, head/foot stabilizing members 516 and side-to-side member 517 are formed from a single bent tube, while in embodiments intended for minimal packaging size, members 516 may attach to members 517 using transverse through-tube screws (not shown) or the like at joints 518.

In a preferred embodiment, lamp support member 521 is made up of tubular member 506, and sliding member 507, which slides within and protrudes from one end of tubular member 506. When assembled, tubular member 506 and sliding member 507 share a common axis, and the axes of holes 519 through member 506, and hole 520 through member 507 are mutually parallel, and perpendicular to the axis of members 506 and 507.

In a preferred embodiment, tubular member 506 has a non-circular interior cross-section, and member 507 has a mating non-circular exterior cross-section, such that when member 507 is slid into member 506, the axis of hole 519 through member 506, and the axis of hole 520 through member 507 are automatically aligned parallel to one another, and perpendicular to the common axis of members 506 and 507.

In a preferred embodiment, it is desirable to suspend red light therapy lamp 508 from tubular member 506 using attachment means that do not penetrate the interior surface of tubular member 506, so that such attachment means do not interfere with member 507 being able to slide freely in and out of tubular member 506. In one preferred embodiment, red light therapy lamp 508 is suspended from combined support member 521 by supports bonded to or clamped around the exterior of tubular member 506. In an alternate preferred embodiment, red light therapy lamp 508 is suspended from cord loops that go around both combined support member 521, and red light therapy lamp 508, as cords 3217 and 3218 go around central subsection 3201 and red light therapy lamp 3219 in FIG. 32. In an alternate preferred embodiment, a combination of bonded and/or clamped attachment hardware may be used along with cords or hooks to suspend red light therapy lamp 508 from combined support member 521.

In a preferred embodiment, vertical tubular members 502 include reduced-diameter ends 511, which mate with holes 519 and 520 at the top end and mate with socket members 514 at the lower end, such that vertical tube members 502 remain stably mated with mattress interface modules 501 by gravitational force. After assembly, diameter reduction ridges 512 sit against end surfaces 513 at the lower ends, and sit against the lower surfaces of sliding tubes 506 and 507 at the upper ends. Thus combined support member 521 is held stably in place by vertical members 502 and by gravity, with no latching or fastening necessary.

The embodiment of the present invention shown in FIG. 50 may be described in claim language as: An adapter for attaching a LED panel red light therapy lamp over a bed, wherein said bed comprises a mattress and a box spring, said adapter comprising: at least two mattress interface modules configured to be sandwiched between said mattress and said box spring; at least two vertical support members, each of said members including an attachment feature at one end configured to attach to one of said mattress interface modules; said vertical support members further each comprising a second attachment feature configured to attach to an upper support member which functions to support said red light therapy lamp.

Red light therapy lamp 508 is suspended from the combination of outer sliding tube 506 (which spans distance 509) and inner sliding member 507 (which spans distance 510). The total length of the combination of sliding tube 506 and sliding member 507 may be adjusted to a range of lengths that includes all common head-to-foot lengths of standard bed sizes.

Figure 42:
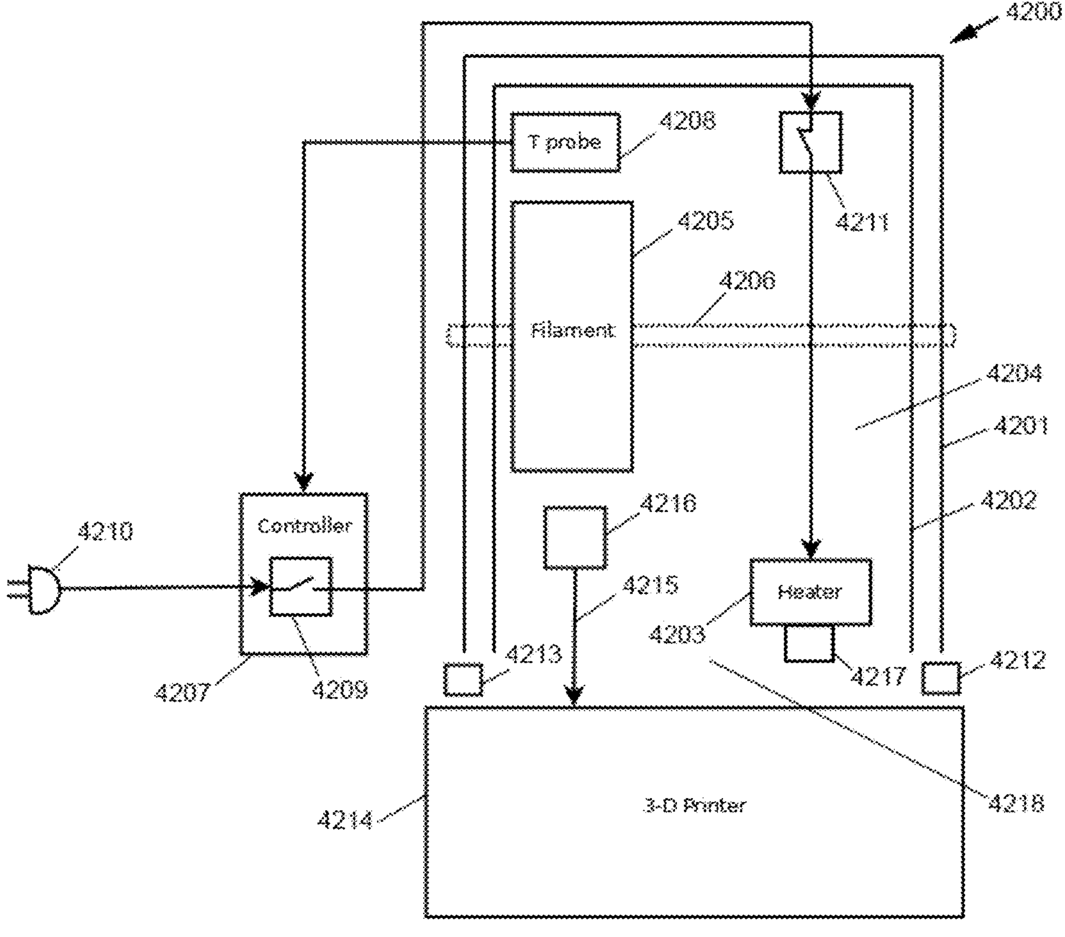
FIG. 42 is a block diagram of a hot box for improved fabrication of flexible light guides according to a preferred embodiment of the present invention.

FIG. 42 is a block diagram of a hotbox for improved fabrication of flexible light guides according to a preferred embodiment of the present invention. Hotbox 4200 includes rigid outer shell 4201, and inner thermal insulating shell 4202. Heater 4203 heats interior 4204. Volume 4204 contains plastic filament roll 4205, which is rotatably mounted on axel 4206. Heater 4203 and filament roll 4205 are surrounded on five sides by thermal insulating layer 4202. Stated another way, when hotbox 4200 is configured for use, thermally insulating hollow shell 4202 surrounds filament roll 4205 and heater 4203 in all horizontal directions extending from all points on roll 4205 and heater 4203, and all upward directions extending from all points on roll 4205 and heater 4203.

The temperature of air within interior 4204 is controlled by controller 4207, which senses air temperature through thermal probe 4208. When interior air temperature is below a pre-determined setpoint, relay 4209 within controller 4207 turns on power to heater 4203. Power is supplied to controller 4207 and relay 4209 through utility plug 4210.

In a preferred embodiment, heater 4203 is an incandescent light bulb which mounts on bracket 4217, which is attached to the frame of 3-D printer 4214. Normally-closed overheat thermostat 4211 disrupts power to heater 4203 if thermal probe 4208 fails, or controller 4207 fails with relay 4209 turned on, causing the temperature of air in interior 4204 to rise above a predetermined overheat temperature.

In a preferred embodiment, hotbox 4200 is supported on support brackets 4212 and 4213, which are mounted to the frame of 3-D printer 4214. Moisture-impermeable filament tube 4215 extends from 3-D printer 4214 up into heated interior 4204, where it is it fixed to bracket 4216, which is mechanically supported by the frame of 3-D printer 4214.

In a preferred embodiment, plastic filament on roll 4205 is heated within interior 4204 to a temperature which may be set using controller 4207. In a preferred embodiment, filament is heated to approximately 70° C. This evaporates moisture contained within the plastic filament on spool 4205 prior to the filament entering moisture-impermeable tube 4215 on its way to 3-D printer 4214. Because tube 4215 is moisture-impermeable, moisture cannot re-enter filament as the filament slowly moves between hotbox 4200 and 3-D printer 4214.

Because bottom opening 4218 of hotbox 4200 is large, it allows moisture driven off from filament spool 4205 to rapidly escape from hotbox 4200, leaving a very low partial pressure of water vapor around filament spool 4205, allowing filament to release almost all of its absorbed moisture before entering moisture-impermeable tube 4215. This offers substantially better performance than hotbox designs known in the art which are substantially closed, and therefore can build up a substantial partial pressure of gaseous water around the heated filament spool, resulting in more moisture still being in the filament when the filament enters the heated extruder of the 3-D printer. The current invention delivering filament containing less moisture to the heated extruder of the 3-D printer allows the elimination of the formation of steam bubbles in the melted filament during the extrusion process, and thus results in a stronger and more uniform 3-D print.

Figure 43:
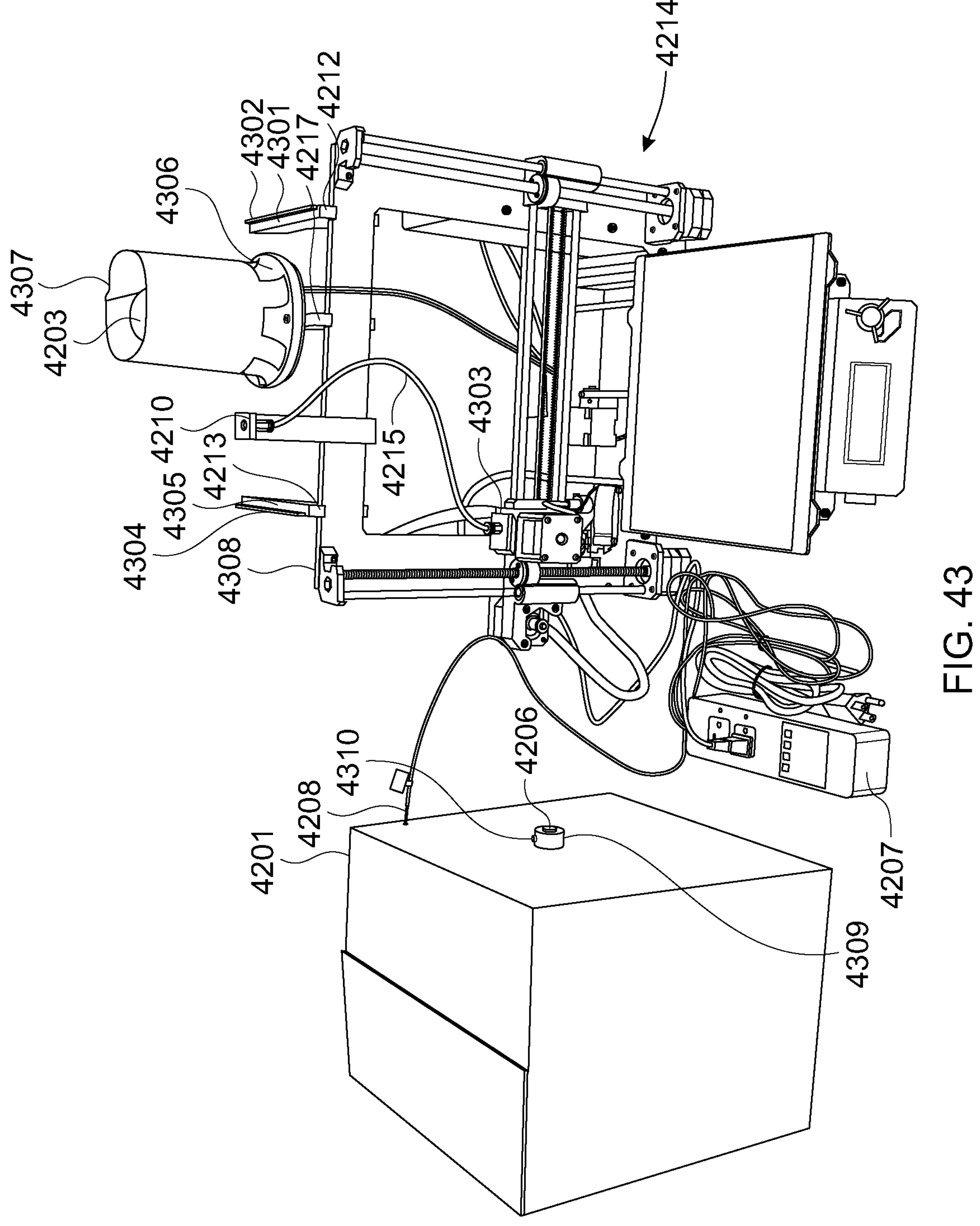
FIG. 43 is a photograph showing a hot box aspect of the present invention, and how it is mounted on a 3-D printer.

FIG. 43 is a photograph showing a hot box aspect of the present invention, and how it is mounted on a 3-D printer. Hotbox support brackets 4212 & 4213 are shown attached to frame 4308 of 3-D printer 4214. Flat support surfaces 4301 and 4305 serve to support right and left lower edges of hot box outer shell 4201, while ribs 4302 and 4304 extend upward from surfaces 4301 and 4305, respectively, to constrain sideways movement of hotbox outer shell 4201 when it is resting on supports 4212 and 4213.

Bracket 4210 attaches to frame 4308 and supports the input end of moisture-impermeable filament feed tube 4215. Adapter 4303 replaces the cover of the direct drive extruder of 3-D printer 4214, attaching to the top of the direct drive extruder with the same screw originally used to attach the extruder top cover. Bracket 4303 serves to attach the output end of moisture-impermeable filament feed tube 4215 to the direct drive extruder of 3-D printer 4214.

In alternate preferred embodiments, any of brackets 4210, 4212, 4213, or 4217 may be integral parts of shell 4201 or 4202, or may be combined to be part of one another. Likewise, rigid shell 4201 and thermally insulating shell 4202 may serve as rigid shell 4201 of vice versa.

Heater support bracket 4217 attaches to frame 4308, and supports a heater assembly made up of heater light bulb 4203, associated light bulb base/socket 4306, and light shield 4307. Light/heat shield 4307 surrounds heater light bulb 4307 to prevent intense light from heater light bulb 4203 from melting a nearby portion of hotbox inner insulation shell 4202 at times when heater light bulb 4302 is energized by controller 4207. In a preferred embodiment, heat/light shield 4307 is made of black-anodized aluminum affixed bulb base 4306, and does not directly contact heater bulb 4203.

Collets 4309 attach with set screws 4310 to opposite ends of axel 4206, adjacent to the sides of hotbox outer shell 4201. In the embodiment shown, axel 4306 passes through and is supported by right and left sides of rigid shell 4201 and thermal insulating shell 4202, traversing completely across interior 4204. In alternate embodiments, axel 4206 may be mounted on a bracket attached to rigid frame 4308, in which case axel 4206 only traverses a portion of interior 4204. In an alternate embodiment, axel 4206 may be supported by one or more inner surfaces of thermally insulating shell 4202, and may not penetrate thermally insulating shell 4202.

Figure 44:
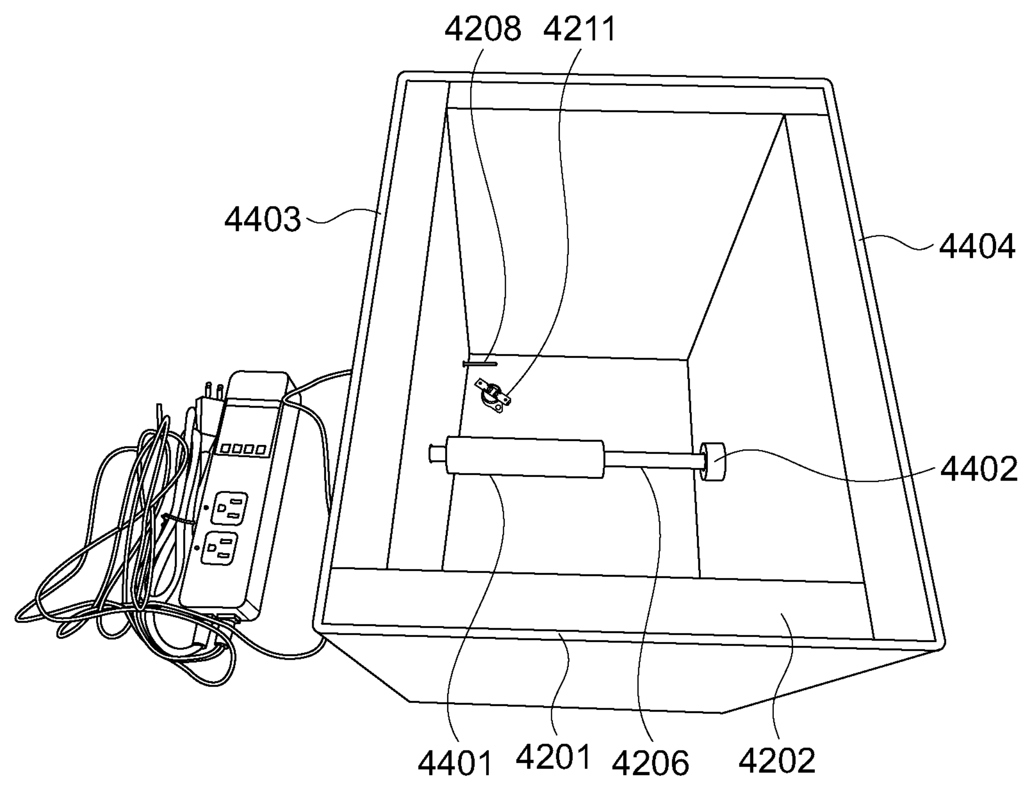
FIG. 44 is two bottom view photos showing the thermal containment shell and mechanical shell of a hotbox according to a preferred embodiment of the present invention, with and without a roll of plastic filament installed.
Figure 44:
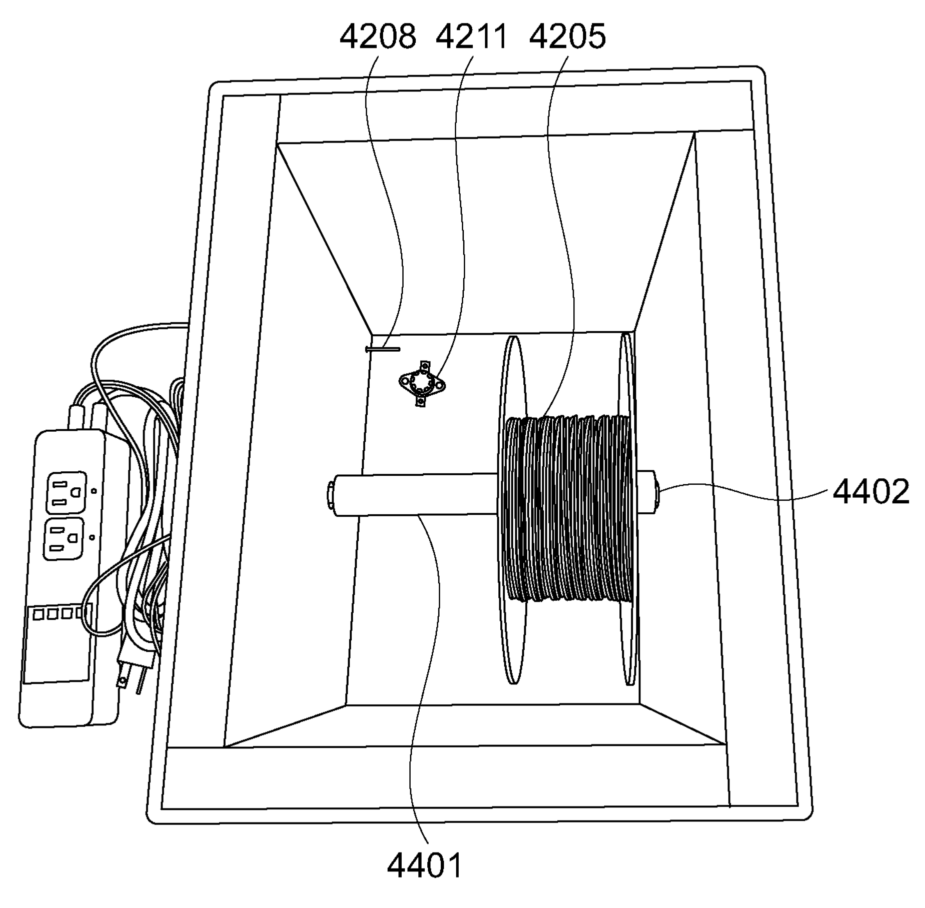

FIG. 44 is two bottom view photos showing the thermal containment shell and mechanical shell of a hotbox according to a preferred embodiment of the present invention, with and without a plastic filament roll 4205 installed. Spacer 4402 is slidably mounted on axel 4206, and serves to prevent filament roll 4205 from contacting thermal containment shell 4202. Spacer 4401 serves to keep filament roll 4205 a safe distance from light & heat shield 4307.

During use, the components shown in FIG. 44 are inverted, and outer shell edges 4403 and 4404 are supported on bracket flat surfaces 4301 and 4305, respectively. When heating bulb 4203 is energized, air heated between 4203 and light/heat shield 4307 rises rapidly, stirring and mixing air throughout interior 4204 of thermal shell 4202. Very little heat escapes through bottom opening 4210 of thermally insulating shell 4202, since warmer air is less dense and therefore rises with respect to cooler air. In a preferred embodiment, thermal shell 4202 is composed of expanded polystyrene foam, though a different polymer form or a different insulating material such as fiberglass may be used. In a preferred embodiment, normally closed overheat thermostat 4211 trips at a temperature below the softening temperature of the material used to make insulating shell 4202, and below the softening temperature of plastic components 4401, 4402, and brackets 4212, 4213, 4215, and 4217.

Figure 45:
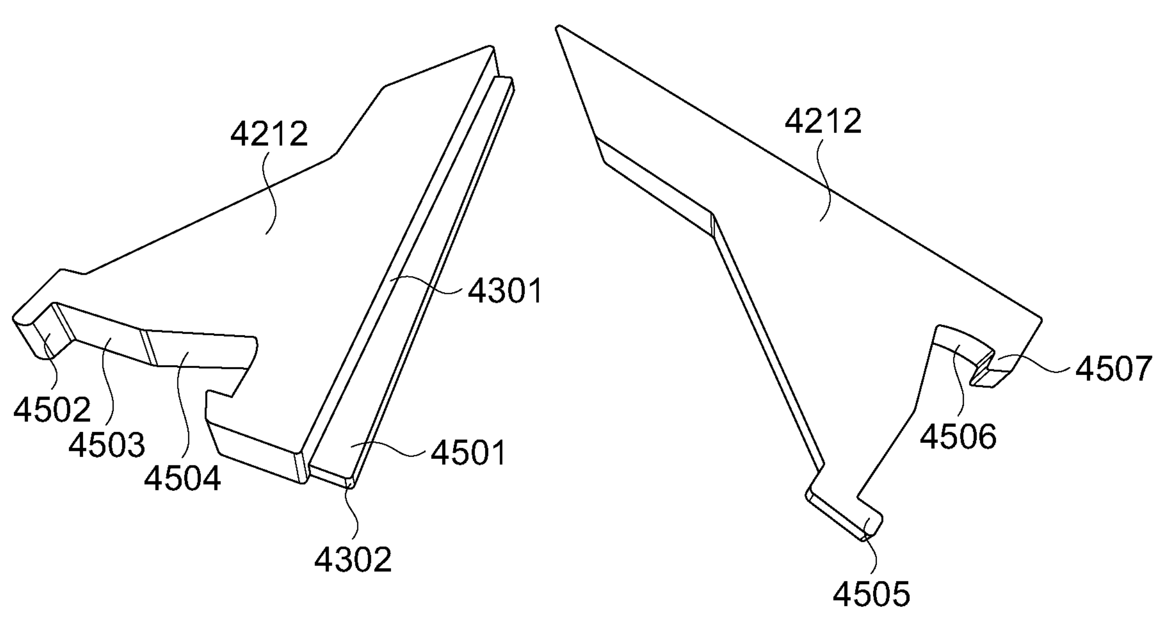
FIG. 45 is two views of a support bracket for a hot box according to aspects of a preferred embodiment of the present invention.
Figure 46:
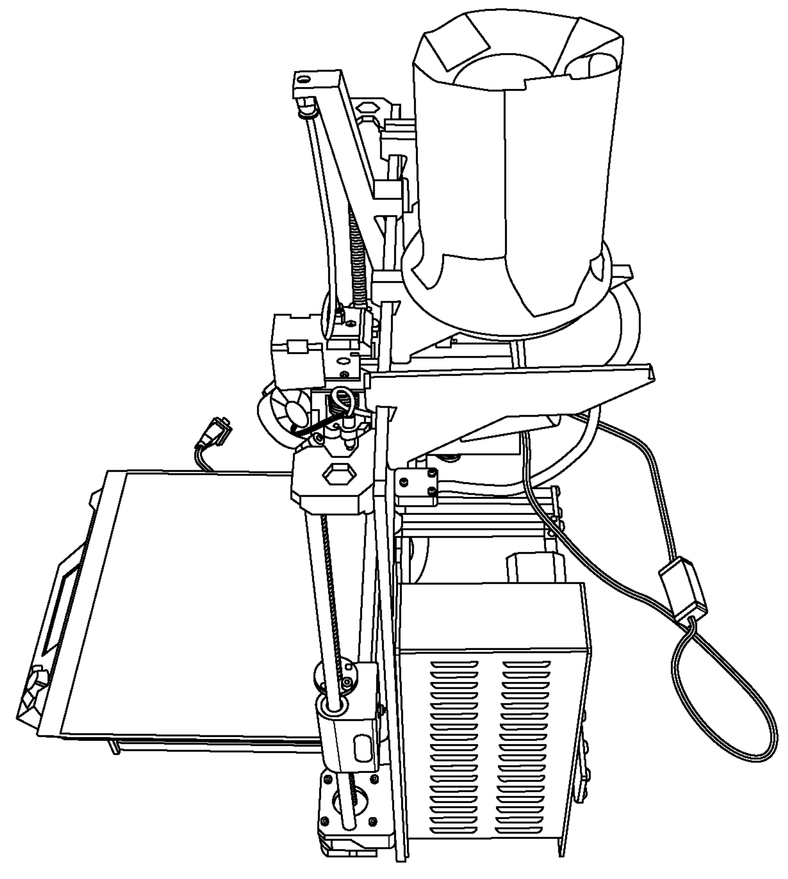
FIG. 46 is a side elevated photo of the 3-D-printer-mounted brackets, heater, and moisture-impermeable filament feed tube of a hotbox according to aspects of a preferred embodiment of the present invention.

FIG. 45 is two views of support bracket 4212. Support bracket 4212 attaches to frame 4308 of 3-D printer 4214 by sliding surface 4504 down along the back surface of the top rail of frame 4308, until surface 4506 contacts the top of frame 4308, then pushing down on surface 4301 until surface 4502 frictionally engages the bottom of the top rail of frame 4308, and surface 4503 mates with the back surface of the top rail of frame 4308, at which point the top of frame 4308 is frictionally held between surface 4502, and surface 4506. In a preferred embodiment, the attachment of brackets 4213, 4215, and 4217 is accomplished in a like manner to the attachment of bracket 4212.

Thus once installed, upward vertical travel of bracket 4212 is blocked by nub 4505, downward vertical travel of bracket 4212 is blocked by surface 4506, and surface 4506 is blocked from sliding off the top of the top rail of frame 4308 by nub 4507, as weight is applied to support surface 4301. Surface 4501 of integral side rail 4302 mates with the right side of hot box shell 4201, preventing sideways travel of hot box shell 4201. In a preferred embodiment, once hotbox shell 4201 is installed on support surfaces 4301 and 4305, forward/backward travel of hotbox shell 4201 is prevented by joining the sides of hotbox shell 4201 to the sides of brackets 4212 and 4213 using plastic tape.

In claim language, the hotbox feature of the present invention might be described as: A hotbox for evaporating moisture from a roll of plastic filament, and delivering dried filament with an external diameter to a direct-drive extruder of a 3-D printer with a rigid frame, said hotbox comprising: a thermally insulating hollow shell with a closed top, an open bottom, an interior, an interior surface, an exterior, and an axel traversing a portion of said interior of said hollow shell, said shell interior sized to contain a temperature-sensing probe, an electrically powered heater, and a roll of plastic filament, said axel of length sufficient to support said roll of plastic filament; said axel acting to support said roll of plastic filament such that said roll of plastic filament can rotate on said axel; further comprising first and second spacers co-axial with said axel, said first spacer acting to prevent said roll of plastic filament from contacting said interior surface of said thermally insulating hollow shell, said second spacer acting to prevent said roll of plastic filament from contacting said heater; said thermally insulating hollow shell configured such that when said roll of plastic filament is mounted on said axel, and said shell is positioned for use, the interior of said thermally insulating hollow shell surrounds said roll of plastic filament and said heater in all horizontal directions extending from all points on said roll of plastic filament and said heater, and all upward directions extending from all points on said roll of plastic filament and said heater; further comprising at least one support bracket configured to attach to said rigid frame, and to support said thermally insulating hollow shell; further comprising at least one support bracket configured to attach to said rigid frame, and to support said heater; further comprising a temperature controller with a temperature-sensing probe, wherein said temperature-sensing probe is placed within the interior of said thermally insulating hollow shell, said temperature controller acting to turn on said electrically powered heater when the temperature sensed by said temperature-sensing probe is below a first pre-determined temperature, said temperature controller acting to turn off said electrically powered heater when the temperature sensed by said temperature-sensing probe is above a second pre-determined temperature; further comprising a normally-closed electrical thermostat wired in series with said heater, wherein said normally closed electrical thermostat acts to disconnect said heater when the temperature sensed by said normally-closed electrical thermostat exceeds a third pre-determined temperature, wherein said third pre-determined temperature is greater than said first and second pre-determined temperatures; further comprising a moisture-impermeable tube with an inner diameter greater than said filament external diameter, said moisture-impermeable tube having an upper end and a lower end, said upper end affixed to a bracket configured to affix to said rigid frame, said lower end affixed to a bracket configured to affix to said direct-drive extruder, said moisture-impermeable tube acting to guide plastic filament from said roll of plastic filament to said direct-drive extruder.

Figure 47:
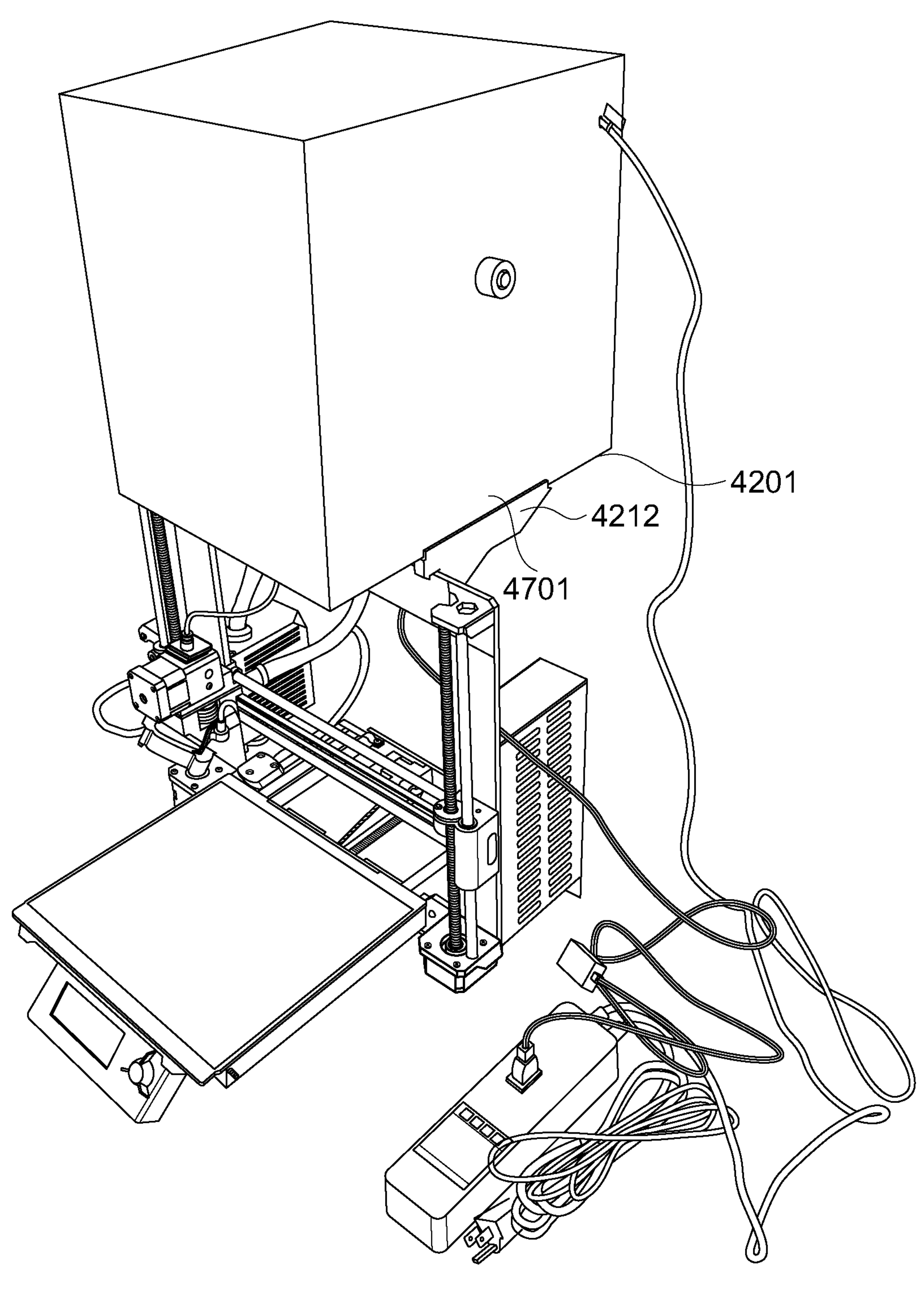
FIG. 47 is a perspective-view photo of a hotbox according to a preferred embodiment of the present invention, assembled onto a 3-D printer.
Figure 48:
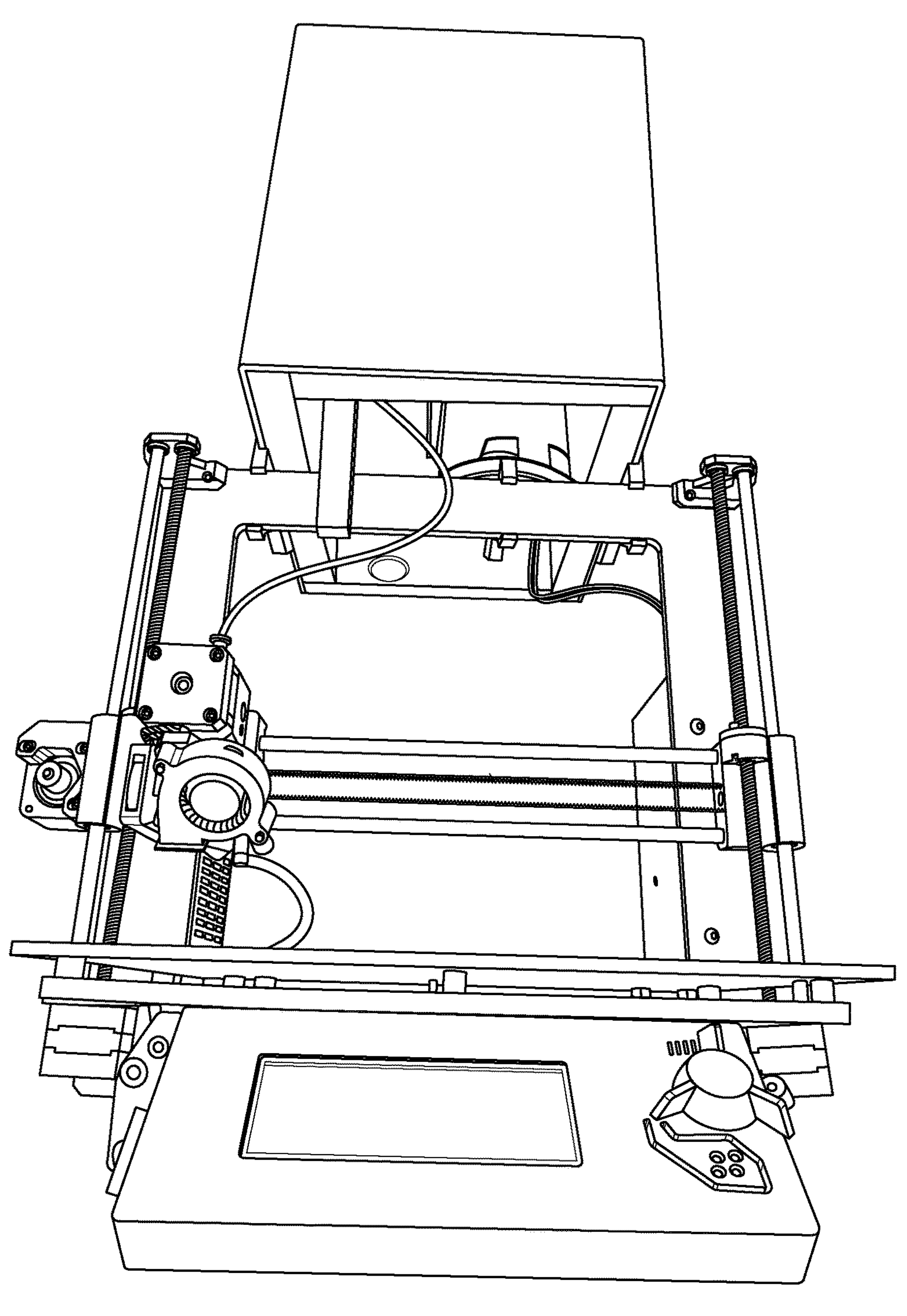
FIG. 48 is an upward-looking perspective view of the underside of a hotbox according to a preferred embodiment of the present invention, assembled onto a 3-D printer.

FIG. 47 is a perspective-view photo of a hotbox according to a preferred embodiment of the present invention, assembled onto a 3-D printer, with transparent tape at location 4701 securing hotbox shell 4201 to bracket 4212. FIG. 48 is an upward-looking perspective view of the underside of a hotbox according to a preferred embodiment of the present invention, assembled onto a 3-D printer.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable non-transitory mediums, such as CD-ROMs or other types of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software. Digital results of any automated process herein may be stored in a non-transitory storage medium such as ROM, RAM, FLASH memory, magnetic disc, etc.; may be printed on paper; may be displayed visually (for instance on a computer monitor, cell phone, or other visible display); may be displayed in audio (for instance synthesized speech); or may be displayed by printing.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments were described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc.. When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the application code or code segments to perform the necessary tasks may be stored in a non-transitory machine readable medium such as a storage medium. One or more processors may perform the necessary tasks. A code segment may represent a procedure, a function, a subprogram, an application, a routine, a subroutine, a module, a software package, a class, or any combination of instructions, data structures, or application statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

What is claimed is:

1. A red light therapy device comprising:

a housing with an interior and an exterior, containing within its interior an array of red-light-emitting LEDs and a power supply;

said housing comprising a bottom surface suitable for stably resting on the surface of a table or floor, and a top surface opposite said bottom surface;

wherein said top surface comprises a top surface perimeter, and an optical opening with an area greater than three square inches;

further comprising a red-light-transparent lens with an optical axis and inner and outer surfaces, said outer surface partially protruding out of said optical opening in a direction parallel to the optical axis of said lens and perpendicular to said top surface, where the portion of said lens protruding through said optical opening comprises a convex surface;

wherein LEDs in said array of LEDs are placed such that said power supply functions to energize said array of LEDs to shine red light through said lens, producing a good-uniformity optical aperture of area at least three square inches coincident with the outer surface of said lens;

wherein said housing further comprises a first set of at least two removable-stand-attachment features;

further comprising a detachable stand, said stand comprising a second set of at least two removable-stand-attachment features;

wherein said first set of removable-stand-attachment features is configured to mate with said second set of removable-stand-attachment features, to removably attach said stand to said housing;

wherein said first set of removable-stand-attachment features comprises one or more pair of ventilation holes, each said pair of ventilation holes being symmetrically disposed about a plane half way between two parallel side surfaces of said housing.

* * * * *